(12) United States Patent
Quintana et al.

(10) Patent No.: US 9,927,437 B2
(45) Date of Patent: Mar. 27, 2018

(54) TREATING NEURODEGENERATIVE DISEASE

(71) Applicant: THE BRIGHAM AND WOMEN'S HOSPITAL, INC., Boston, MA (US)

(72) Inventors: Francisco J. Quintana, Jamaica Plain, MA (US); Lior Mayo, Fivataim (IL); Howard Weiner, Brookline, MA (US); Reza Halse, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/103,632

(22) PCT Filed: Dec. 12, 2014

(86) PCT No.: PCT/US2014/070099
§ 371 (c)(1),
(2) Date: Jun. 10, 2016

(87) PCT Pub. No.: WO2015/089443
PCT Pub. Date: Jun. 18, 2015

(65) Prior Publication Data
US 2016/0313324 A1    Oct. 27, 2016

Related U.S. Application Data

(60) Provisional application No. 61/963,738, filed on Dec. 12, 2013, provisional application No. 62/049,813, filed on Sep. 12, 2014.

(51) Int. Cl.
| | |
|---|---|
| *G01N 33/564* | (2006.01) |
| *C12N 15/113* | (2010.01) |
| *A61K 31/445* | (2006.01) |
| *A61K 31/5375* | (2006.01) |
| *A61K 31/713* | (2006.01) |

(52) U.S. Cl.
CPC ......... *G01N 33/564* (2013.01); *A61K 31/445* (2013.01); *A61K 31/5375* (2013.01); *A61K 31/713* (2013.01); *C12N 15/1137* (2013.01); *C12N 2310/14* (2013.01); *C12N 2320/30* (2013.01); *G01N 2400/00* (2013.01); *G01N 2405/00* (2013.01); *G01N 2800/285* (2013.01); *G01N 2800/50* (2013.01)

(58) Field of Classification Search
CPC .......................... G01N 33/564; C12N 15/1137
See application file for complete search history.

(56) References Cited

U.S. PATENT DOCUMENTS

| | | | |
|---|---|---|---|
| 8,263,576 | B2 | 9/2012 | Pagano et al. |
| 2011/0092383 | A1 | 4/2011 | Dotan et al. |
| 2011/0245188 | A1 | 10/2011 | Singh |
| 2012/0077686 | A1 | 3/2012 | Weiner et al. |
| 2012/0157976 | A1 | 6/2012 | Davies et al. |

FOREIGN PATENT DOCUMENTS

| | | |
|---|---|---|
| EP | 1825853 | 8/2007 |
| WO | WO 2005/123055 | 12/2005 |

OTHER PUBLICATIONS

Meivar-Levy et al. "Up-regulation of Neutral Glycosphingolipid Synthesis upon Long Term Inhibition of Ceramide Synthesis by Fumonisin B1" Journal of Biological Chemistry, 1999, vol. 274, pp. 4607-4612.*
Radin "Chemotherarpy by Slowing Glucosphingolipid Synthesis" Biochemical Pharmacology, 1999, vol. 57, pp. 589-595.*
Pannu et al. "A Novel Role of Lactosylceramide in the Regulation of Tumor Necrosis Factor α-mediated Proliferation of Rat Primary Astrocytes Implications for Astrogliosis Following Neurotrauma" Journal of Biological Chemistry, 2005, vol. 280, pp. 13742-13751.*
Ajami, "Infiltrating monocytes trigger EAE progression, but do not contribute to the resident microglia pool." Nat Neurosci, Sep. 2011, 14: 1142-1149.
Basso et al., "Reversal of axonal loss and disability in a mouse model of progressive multiple sclerosis," J Clin Invest, Apr. 2008, 118: 1532-1543.
Bi et al., "Reactive astrocytes secrete lcn2 to promote neuron death," PNAS, Mar. 2013, 110: 4069-4074.
Bush et al., "Leukocyte infiltration, neuronal degeneration, and neurite outgrowth after ablation of scar-forming, reactive astrocytes in adult transgenic mice," Neuron, 1999, 23: 297-308.
Cahoy et al., "A transcriptome database for astrocytes, neurons, and oligodendrocytes: a new resource for understanding brain development and Function," J Neurosci, 2008, 28: 264-278.
Cao et al., "Leukemia inhibitory factor inhibits T helper 17 cell differentiation and confers treatment effects of neural progenitor cell therapy in autoimmune disease," Immunity, 2011, 35: 273-284.
Cardona et al., "Isolation of murine microglial cells for RNA analysis or flow cytometry," Nat Protoc, 2006, 1: 1947-1951.
Chatterjee and Alsaeedi, "Lactosylceramide synthase as a therapeutic target to mitigate multiple human diseases in animal models," Adv Exp Med Biol Apr. 2012, 749: 153-469.
Clarke and Barres, "Emerging roles of astrocytes in neural circuit development," Nat Rev Neurosci, May 2013, 14: 311-321.
Codarri et al., "RORγt drives production of the cytokine GM-CSF in helper T cells, which is essential for the effector phase of autoimmune neuroinflammation," Nat Immunol, Jun. 2011, 12: 560-567.

(Continued)

*Primary Examiner* — Joseph R Kosack
(74) *Attorney, Agent, or Firm* — Fish & Richardson P.C.

(57) ABSTRACT

As described herein, lactosylceramide (LacCer) levels are up-regulated in the CNS during chronic experimental autoimmune encephalomyelitis (EAE), an experimental model of multiple sclerosis (MS). LacCer acts in an autocrine manner to trigger transcriptional programs that promote the recruitment and activation of CNS infiltrating monocytes and microglia, and neurodegeneration. In addition, increased B4GALT6 expression and LacCer levels were detected in CNS MS lesions in human patients. Finally, the inhibition of LacCer synthesis suppressed local CNS innate immunity and neurodegeneration in EAE, and interfered with the activation of human astrocytes in vitro. Thus, B4GALT6 is a therapeutic target for MS and other neuroinflammatory disorders.

16 Claims, 43 Drawing Sheets

(56) References Cited

OTHER PUBLICATIONS

Colombo et al., "Stimulation of the neurotrophin receptor TrkB on astrocytes drives nitric oxide production and neurodegeneration," J Exp Med, 2012, 209: 521-535.
Compston and Coles, "Multiple sclerosis," Lancet, Oct. 2008, 372: 1502-1517.
David and Kroner, "Repertoire of microglial and macrophage responses after spinal cord injury," Nat Rev Neurosci., 2011, 12: 388-399.
Dohi et al., "An IgG3 Monoclonal Antibody Established after Immunization with GM3 Lactone: Immunochemical Specificity and Inhibition of Melanoma Cell Growth in Vitro and in Vivo," Cancer Res., Oct. 1988, 48:5680-5685.
El-Behi et al., "The encephalitogenicity of T(H)17 cells is dependent on IL-1- and IL-23-induced production of the cytokine GM-CSF," Nat Immunol, Jun. 2011, 12: 568-575.
Farez et al., "Toll-like receptor 2 and poly(ADP-ribose) polymerase 1 promote central nervous system neuroinflammation in progressive EAE," Nat Immunol, Sep. 2009, 10: 958-964.
Freeman, "Specification and morphogenesis of astrocytes," Science, Nov. 2010, 330: 774-778.
Fujibayashi and Wenger, "Studies on a sphingolipid activator protein (SAP-2) in fibroblasts from patients with lysosomal storage diseases, including Niemann-Pick disease Type C," Clin. Chim. Acta., Mar. 1985, 146(2-3):147-56.
Hamamura et al., "Ganglioside GD3 promotes cell growth and invasion through p130Cas and paxillin in malignant melanoma cells," PNAS, Aug. 2005, 102 (31):11041-11046.
Heppner et al., "Experimental autoimmune encephalomyelitis repressed by microglial paralysis," Nat Med, Feb. 2005, 11: 146-152.
Hochstim et al., "The spinal cord contains positionally distinct astrocyte subtypes whose identities are specified by a homeodomain transcriptional code," Cell, May 2008, 133: 510-522.
Huang et al., "Absence of monocyte chemoattractant protein 1 in mice leads to decreased local macrophage recruitment and antigen-specific T helper cell type 1 immune response in experimental autoimmune encephalomyelitis," J Exp Med, Mar. 2001, 193: 713-726.
Hurwitz et al., "The diagnosis of multiple sclerosis and the clinical subtypes," Ann Indian Acad Neurol., Oct. 2009, 12(4): 226-230.
Izikson et al., "Resistance to experimental autoimmune encephalomyelitis in mice lacking the CC chemokine receptor (CCR)2," J Exp Med, 2000, 192: 1075-1080.
Jack et al., "TLR signaling tailors innate immune responses in human microglia and astrocytes," J Immunol, 2005, 175: 4320-4330.
Jahng et al., "Prevention of autoimmunity by targeting a distinct, noninvariant CD Id-reactive T cell population reactive to sulfatide," J Exp Med, 2004,199: 947-957.
Jeyakumar et al., "Storage Solutions: Treating Lysosomal Disorders of the Brain," Nature Reviews, Sep. 2005,6: 713-725.
Jiang et al., "Down-regulation of β1,4-galactosyltransferase V is a critical part of etoposide-induced apoptotic process and could be mediated by decreasing Sp1 levels in human glioma cells," Glycobiology, 2006, 16: 1045-1051.
Joseph et al., "IL-17 silencing does not protect nonobese diabetic mice from autoimmune diabetes," J Immunol, 2012, 188: 216-221.
Kanter et al., "Lipid microarrays identify key mediators of autoimmune brain inflammation," Nat Med, Jan. 2006, 12: 138-143.
Krausgruber et al., "IRF5 promotes inflammatory macrophage polarization and TH1-THI 7 responses," Nat Immunol, Mar. 2011, 12: 231-238.
Kunis et al., "IFN-γ-dependent activation of the brain's choroid plexus for CNS immune surveillance and repair," Brain, 2013, 136: 3427-3440.
Lawrence and Natoli, "Transcriptional regulation of macrophage polarization: enabling diversity with identity," Nat Rev Immunol. Nov. 2011,11(11):750-61.

Lee et al., "Lactosylceramide Mediates the Expression of Adhesion Molecules in TNF-α and IFNγ-stimulated Primary Cultured Astrocytes," Korean J Physiol Pharmacol., Oct. 2011, 15: 251-258.
Lopez-Diego and Weiner, "Novel therapeutic strategies for multiple sclerosis—a multifaceted adversary," Nat Rev Drug Discov., Nov. 2008, 7: 909-925.
Maragakis and Rothstein, "Mechanisms of Disease: astrocytes in neurodegenerative disease," Nature Clinical Practice Neurology, Sep. 2006, 2: 679-689.
Martinez et al., "Macrophage activation and polarization," Frontiers in Bioscience, Jan. 2008,13: 453-461.
Matyash and Kettenmann, "Heterogeneity in astrocyte morphology and physiology," Brain Res Rev, May 2010, 63: 2-10.
Mayo et al., "The innate immune system in demyelinating disease," Immunol Rev, 2012, 248: 170-187.
McDonald et al., "Recommended Diagnostic Criteria for Multiple Sclerosis: Guidelines from the International Panel on the Diagnosis of Multiple Sclerosis," Ann. Neurol., 2001, 50:121-127.
Menheniott et al., "Derivation of primary choroid plexus epithelial cells from the mouse," Methods in Molecular Biology, 2010, 633: 207-220.
Mildner et al., "CCR2+Ly-6Chi monocytes are crucial for the effector phase of autoimmunity in the central nervous system," Brain, Jun. 2009,132: 2487-2500.
Miron et al., "M2 microglia and macrophages drive oligodendrocyte differentiation during CNS remyelination," Nat Neurosci, 2013, 16: 1211-1218.
Molofsky et al., "Astrocytes and disease: a neurodevelopmental perspective," Genes and Development, 2012, 26: 891-907.
Murray and Wynn, "Protective and pathogenic functions of macrophage subsets," Nat Rev Immunol., 2011, 11(11):723-37.
Myer et al., "Essential protective roles of reactive astrocytes in traumatic brain injury," Brain, 2006, 129: 2761-2772.
Nair et al., "Astrocytes in multiple sclerosis: a product of their environment" Cellular and Molecular Life Sciences, Sep. 2008, 65: 2702-2720.
Nishie et al, "Beta4-galactosyltransferase-5 is a lactosylceramide synthase essential for mouse extra-embryonic development," Glycobiology, 2010, 20: 1311-1322.
Nolte et al., "GFAP promoter-controlled EGFP-expressing transgenic mice: a tool to visualize astrocytes and astrogliosis in living brain tissue," Glia, 2001, 33: 72-86.
Nylander and Hafler, "Multiple Sclerosis," J Clin Invest, Apr. 2012, 1180-1188.
Pannu et al., "A novel role of lactosylceramide in the regulation of lipopolysaccharide/interferon-gamma-mediated inducible nitric oxide synthase gene expression: implications for neuroinflammatory diseases," J Neurosci, Jun. 2004, 24: 5942-5954.
Platt et al., "Prevention of lysosomal storage in Tay-Sachs mice treated with N-butyldeoxynojirimycin," Science, Apr. 1997, 276: 428-431.
Pluchino et al., "Injection of adult neurospheres induces recovery m a chronic model of multiple sclerosis," Nature, 2003, 422: 688-694.
Polman et al., "Diagnostic Criteria for Multiple Sclerosis: 2005 Revisions to the McDonald Criteria," Ann Neurol, 2005, 58:840-846.
Ponomarev et al., "GM-CSF production by autoreactive T cells is required for the activation of microglial cells and the onset of experimental autoimmune encephalomyelitis," J Immunol, 2007, 178: 39-48.
Prinz et al., "Heterogeneity of CNS myeloid cells and their roles in neurodegeneration," Nat Neurosci, 2011, 14: 1227-1235.
Quintana et al., "Lipids and lipid-reactive antibodies as biomarkers for multiple sclerosis," J Neuroimmunol, 2012, 248: 53-57.
Rouach et al., "Astroglial metabolic networks sustain hippocampal synaptic transmission," Science, 2008, 322: 1551-1555.
Rovaris et al., "Secondary progressive multiple sclerosis: current knowledge and future challenges," Lancet Neurol 2006, 5: 343-354.
Saura et al., "High-yield isolation of murine microglia by mild trypsinization," Glia, 2003, 44: 183-189.
Schwab et al., "Resolvin E1 and protectin D1 activate inflammation-resolution programmes,". Nature, Jun. 2007, 447: 869-874.

(56) References Cited

OTHER PUBLICATIONS

Seifert et al., "Astrocyte dysfunction in neurological disorders: a molecular perspective," Nat Rev Neurosci, Mar. 2006, 7: 194-206.
Sica and Mantovani, "Macrophage plasticity and polarization: m vivo veritas," J Clin Invest, 2012, 122: 787-795.
Sofroniew, "Molecular dissection of reactive astrogliosis and glial scar formation," Trends in Neurosciences, 2009, 32: 638-647.
Symington et al., "Monoclonal Antibody Specific for Lactosylceramide," J Biol Chem, 1984, 259:6008-6012.
Toft-Hansen et al., "Inhibition of reactive astrocytosis in established experimental autoimmune encephalomyelitis favors infiltration by myeloid cells over T cells and enhances severity of disease," Glia, 2011, 59: 166-176.
Tokuda et al., "β4GalT6 is involved in the synthesis of lactosylceramide with less intensity than βGalT5," Glycobiology, 2013, 23: 1175-1183.
Tsai et al., "Regional astrocyte allocation regulates CNS synaptogenesis and repair," Science, Jul. 2012, 337: 358-362.
Ulitsky et al., "Expander: from expression micro arrays to networks and functions," Nat Protoc, 2010, 5: 303-322.
Venier and Igdoura, "Miglustat as a therapeutic agent: prospects and caveats," J Med Genet, Nov. 2012, 49: 591-597.
Voskuhl et al., "Reactive astrocytes form scar-like perivascular barriers to leukocytes during adaptive immune inflammation of the CNS," J Neurosci, Sep. 2009, 29: 11511-11522.
Watkins et al., "Distinct stages of myelination regulated by gamma-secretase and astrocytes in a rapidly myelinating CNS coculture system," Neuron, 2008, 60: 555-569.
Weiler et al., "Identification of the binding and activating sites of the sphingolipid activator protein, saposin C, with glucocerebrosidase," Protein Sci., Apr. 1995, 4(4):756-64.
Weiler et al., "Synthesis and characterization of a bioactive 82-residue sphingolipid activator protein, saposin C," J Mol Neurosci., 1993, 4(3):161-72.
Weiner, "The challenge of multiple sclerosis: how do we cure a chronic heterogeneous disease?," Ann Neurol, 2009, 65: 239-248.
Yan et al., "CNS-specific therapy for ongoing EAE by silencing IL-17 pathway in astrocytes," Molecular Therapy, Jul. 2012, 20: 1338-1348.
Yoneshige et al., "A mutation in the saposin C domain of the sphingolipid activator protein (Prosaposin) gene causes neurodegenerative disease in mice," J Neurosci Res., Aug. 2010, 88(10):2118-34.
Zamanian et al., "Genomic analysis of reactive astrogliosis," J Neurosci, 2012, 32: 6391-6410.
Zhang and Barres, "Astrocyte heterogeneity: an underappreciated topic in neurobiology," Curr Opin Neurobiol, 2010, 20: 588-594.
Zschoche et al., "Hydrolysis of lactosylceramide by human galactosylceramidase and GM1-beta-galactosidase in a detergent-free system and its stimulation by sphingolipid activator proteins, sap-B and sap-C. Activator proteins stimulate lactosylceramide hydrolysis," Eur J Biochem., May 1994, 222(1):83-90.
International Search Report and Written Opinion dated Apr. 10, 2015 in International Application No. PCT/US2014/070099, 19 pgs.
Nomura et al. "Purification, cDNA Cloning, and Expression of UDP-Gal: Glucosylceramide β-1,4-Galactosyltransferase from Rat Brain," J. Biol. Chem, May 1998, 273:13570-13577.
Extended European Search Report in Application No. 14868919.3, dated Jun. 7, 2017, 4 pages.

\* cited by examiner

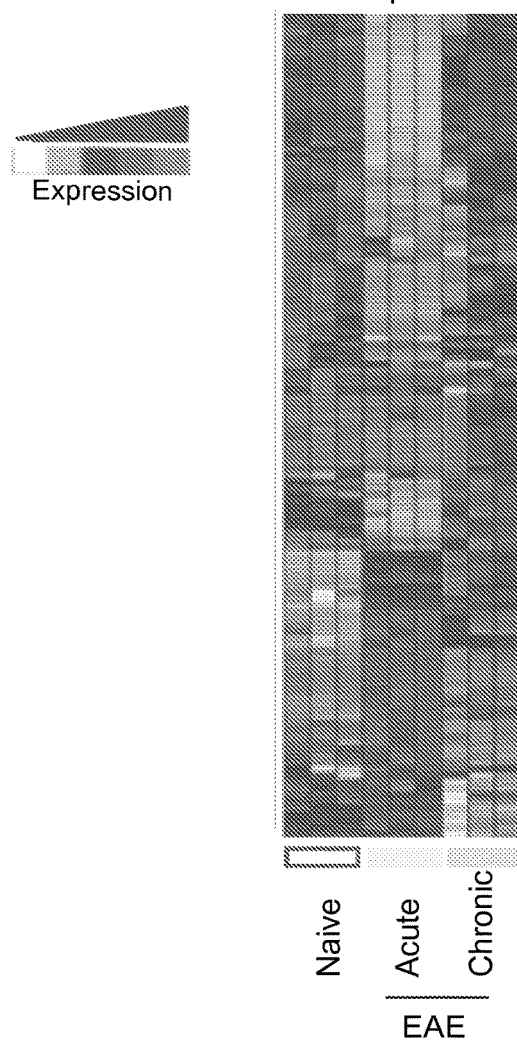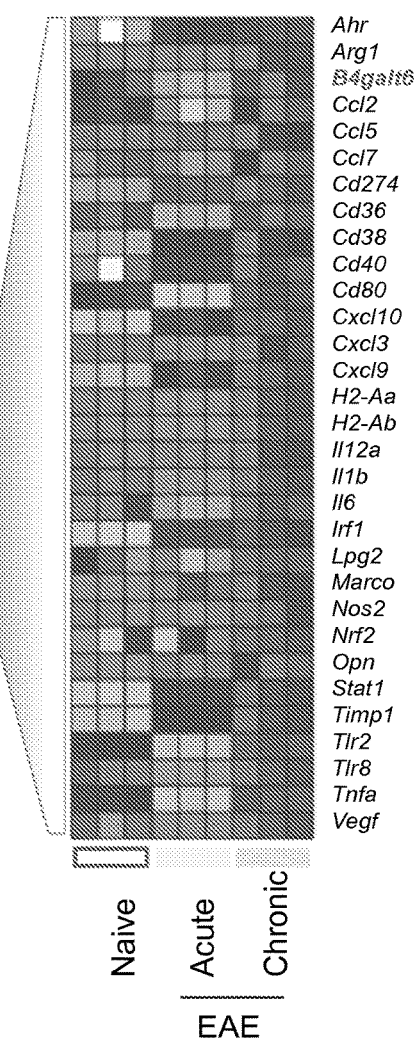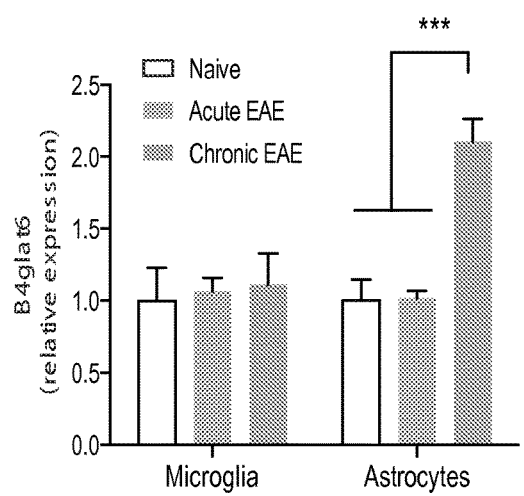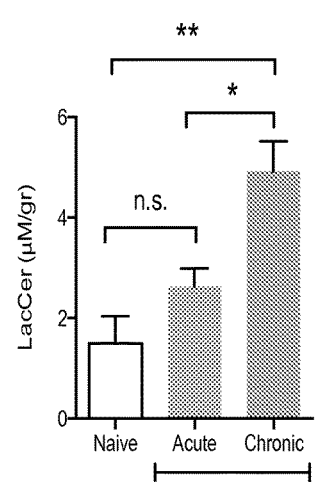
FIG. 1C Astrocytes inflammatory transcriptome
FIG. 1D "Chronic phase" cluster
FIG. 1E
FIG. 1F

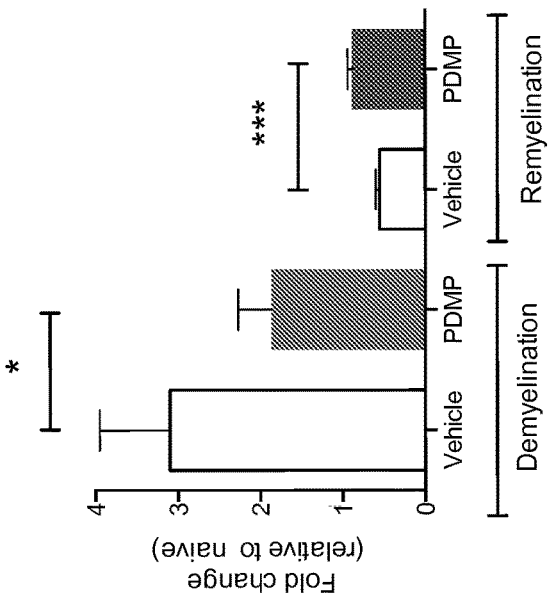
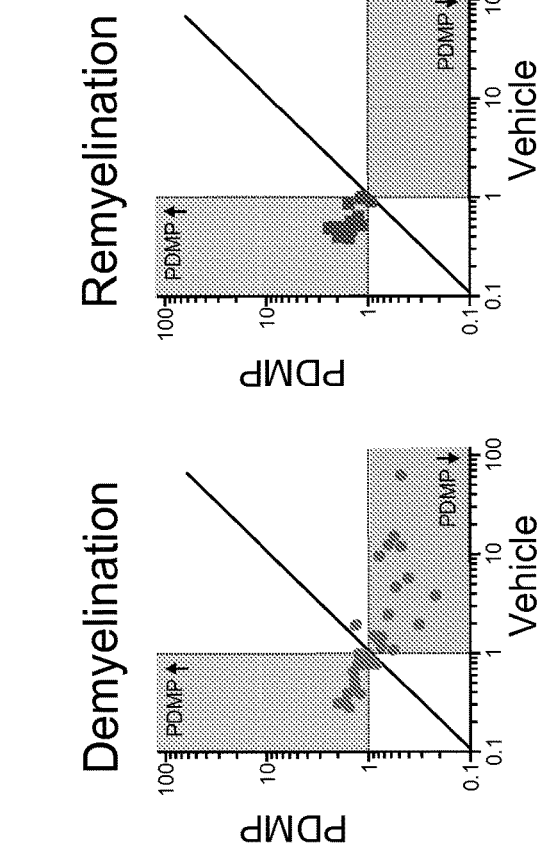
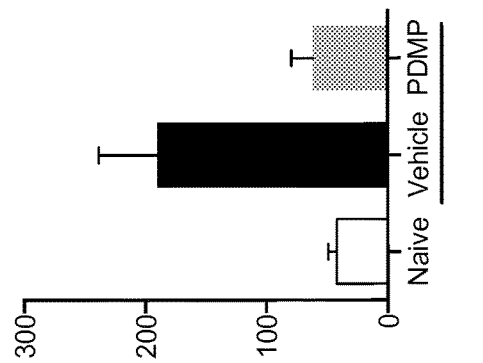
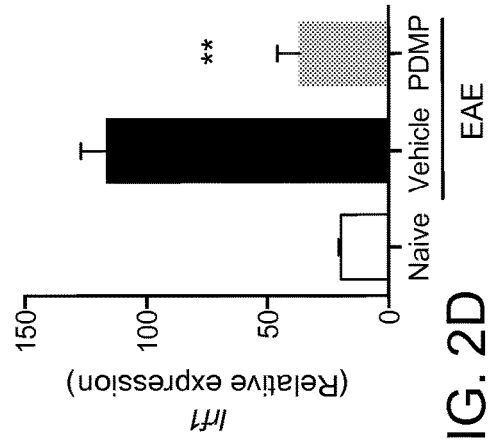

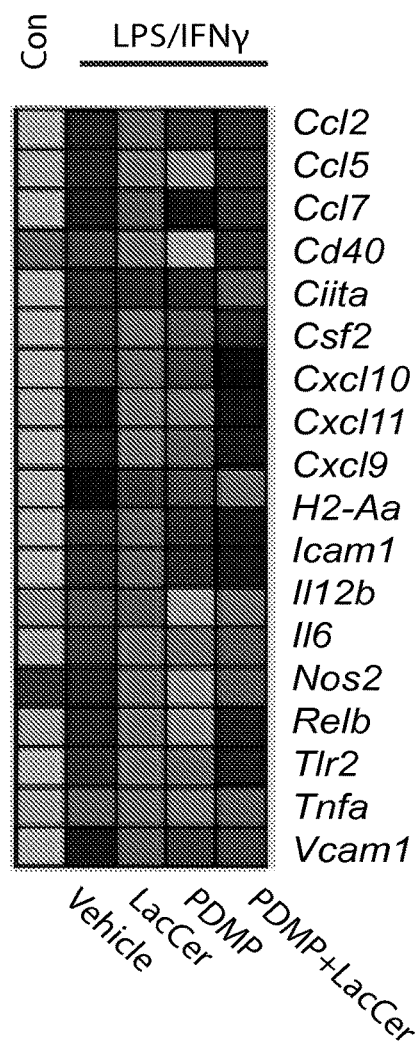
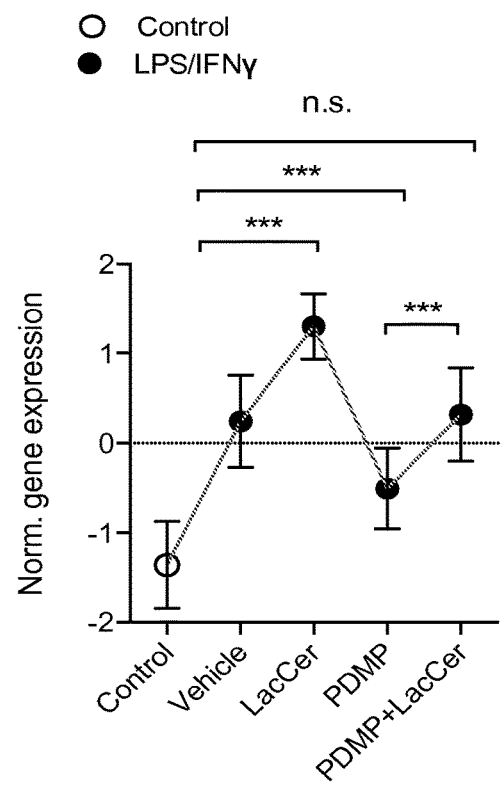
FIG. 3A
FIG. 3B

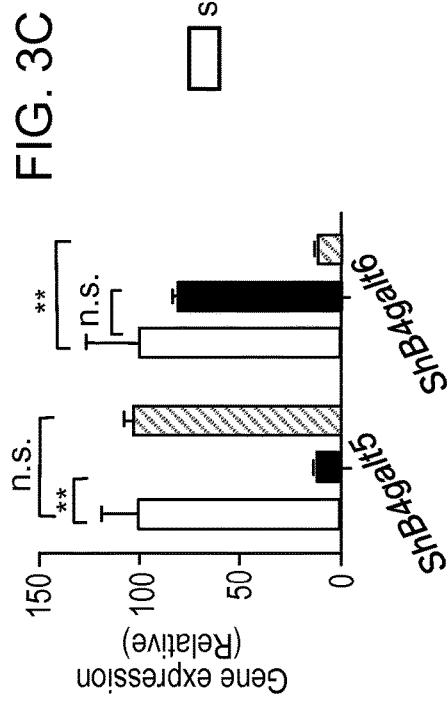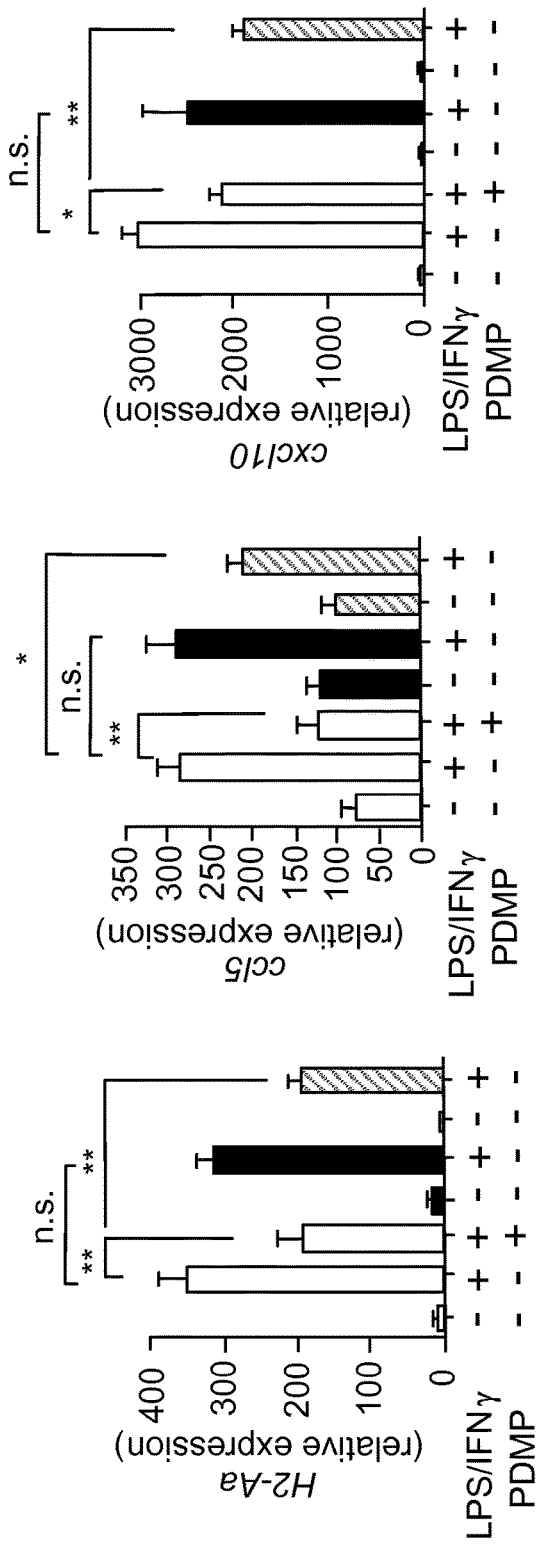
FIG. 3C, FIG. 3D, FIG. 3E, FIG. 3F

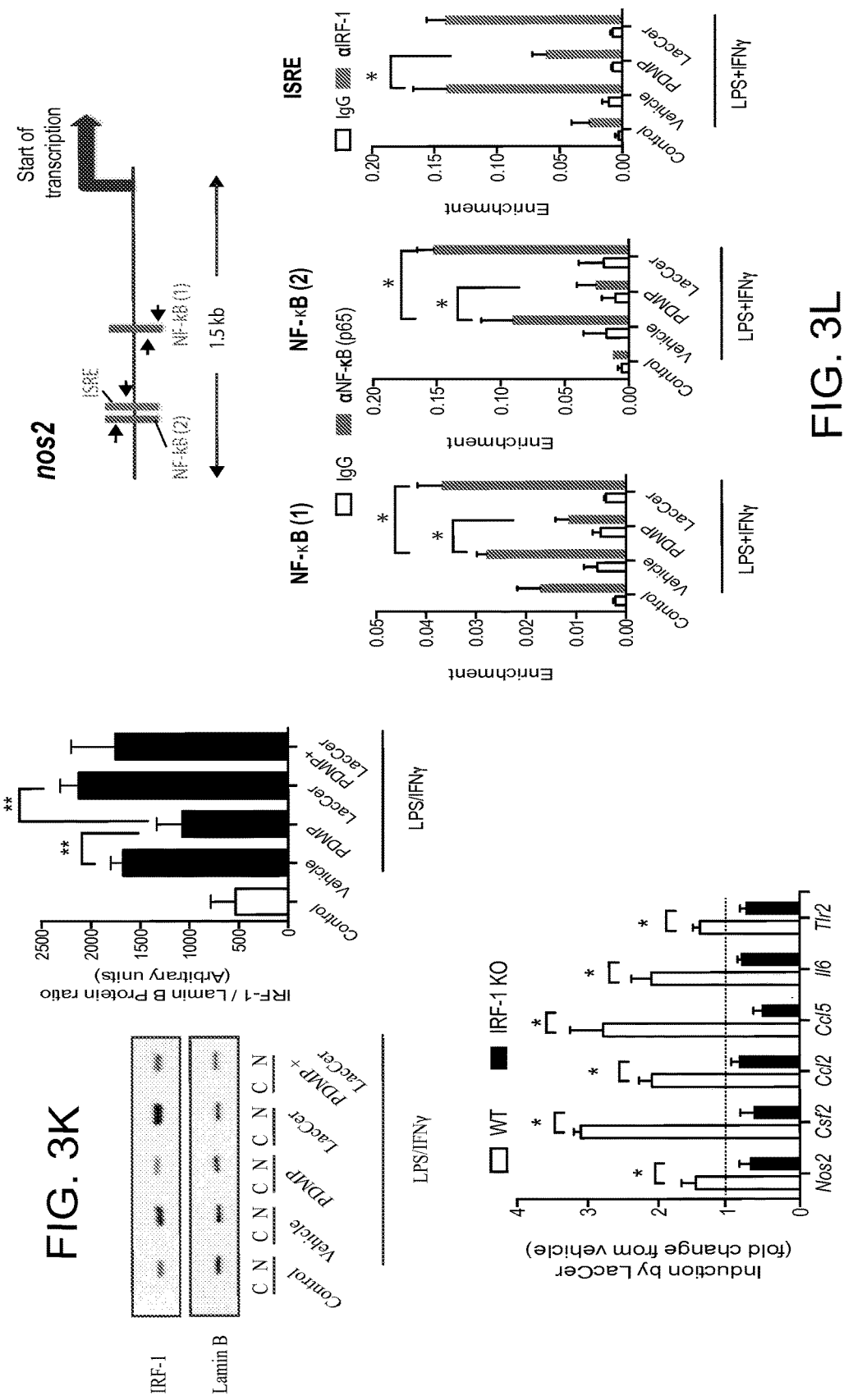

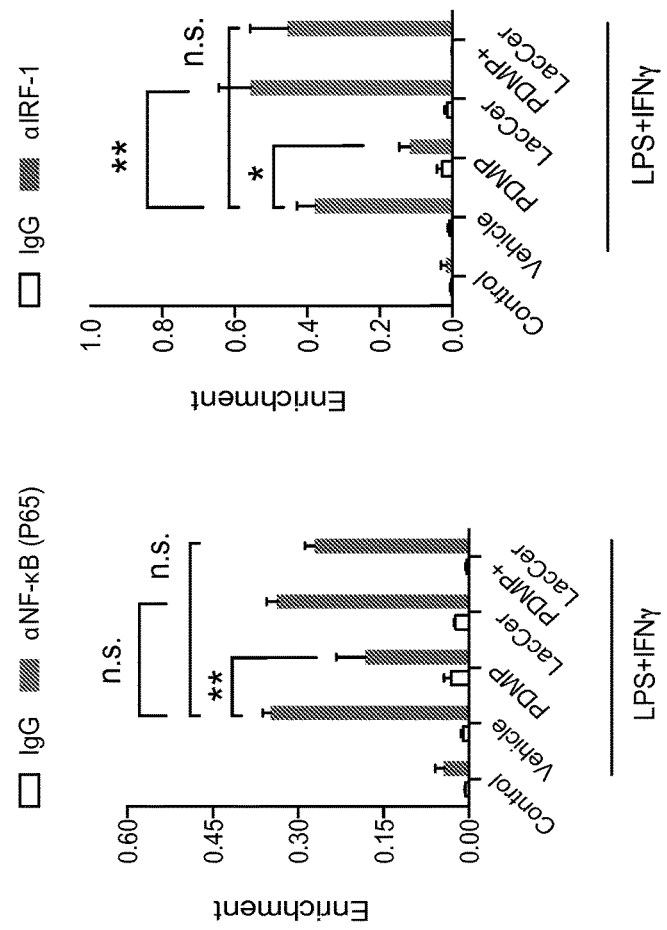
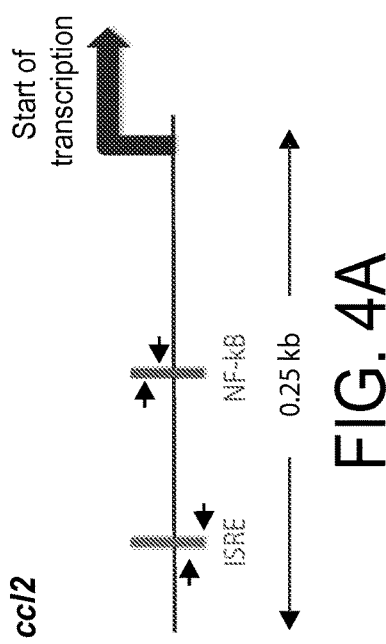
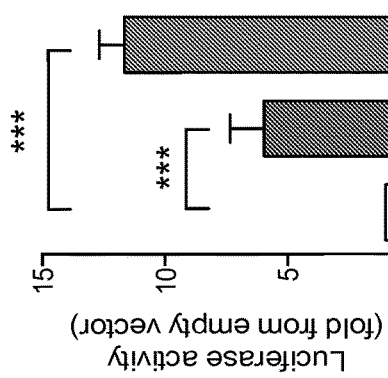

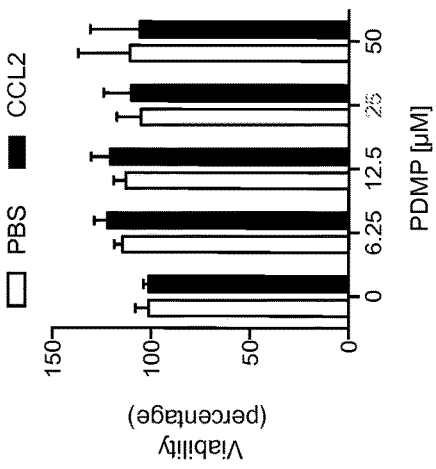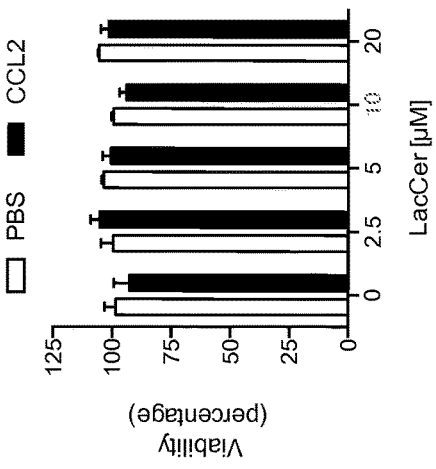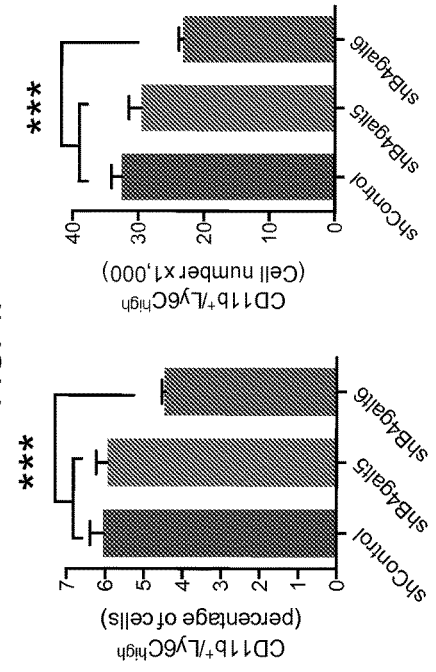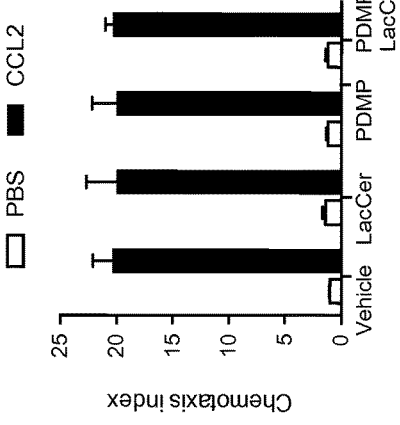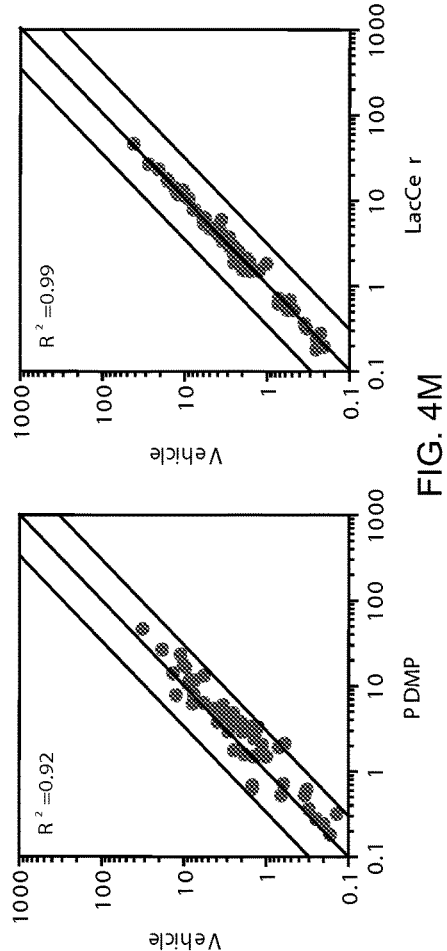

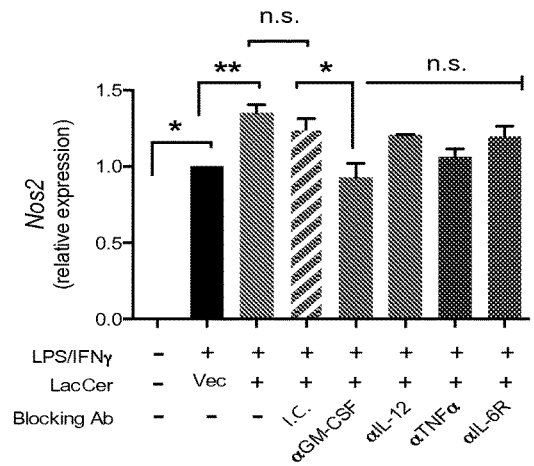
FIG. 5J
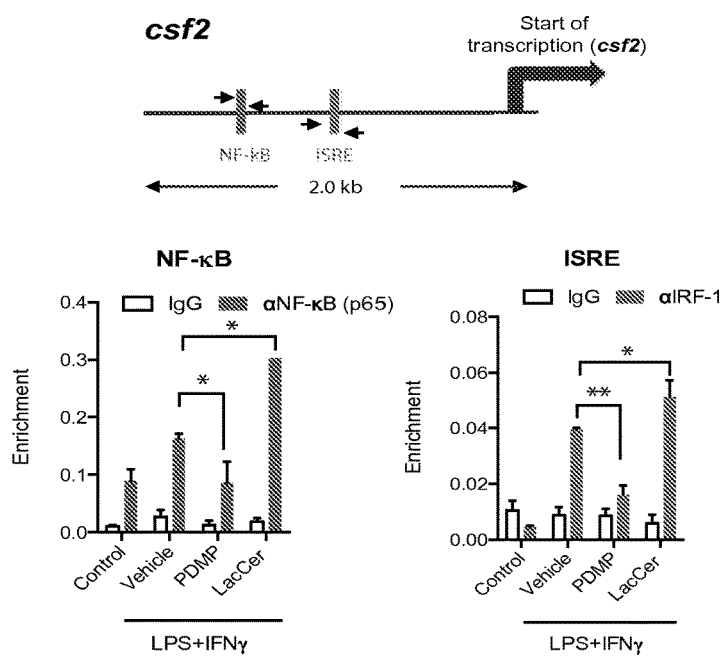
FIG. 5K
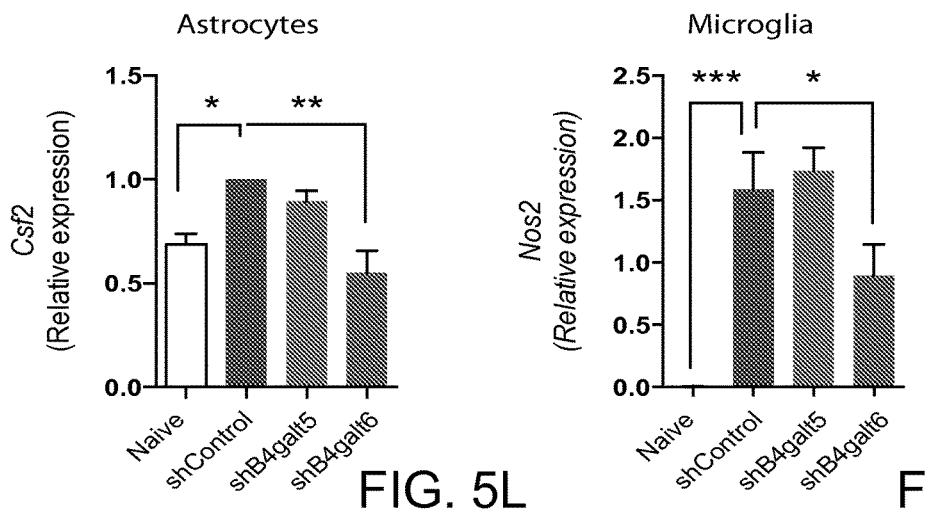
FIG. 5L
FIG. 5M

Axonal density
(Bielschowsky's silver staining)

Naive

EAE

Myelin content
(Luxol fast blue staining)

Naive

EAE

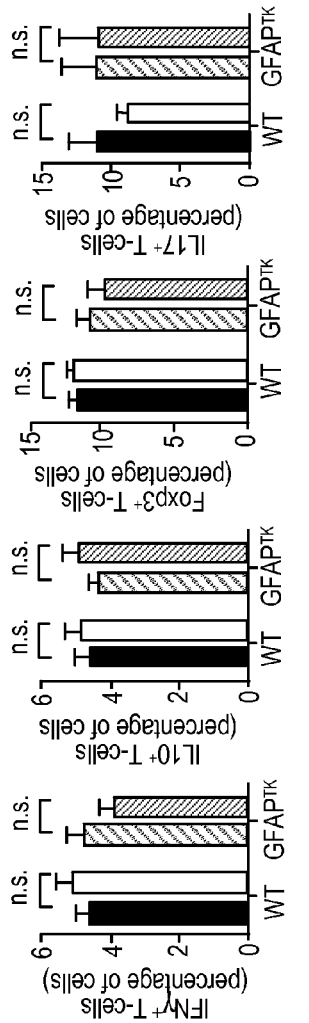
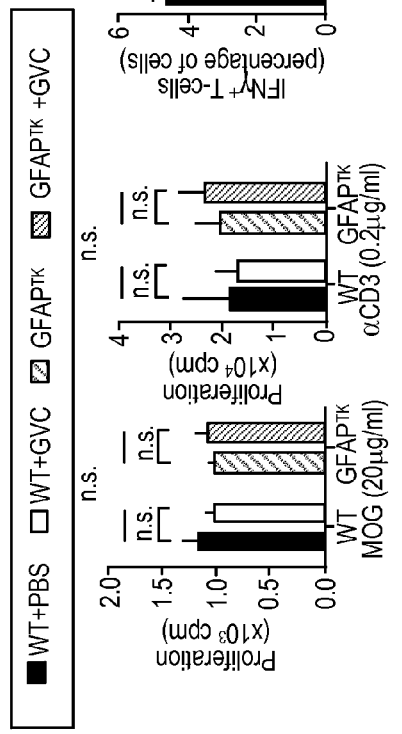
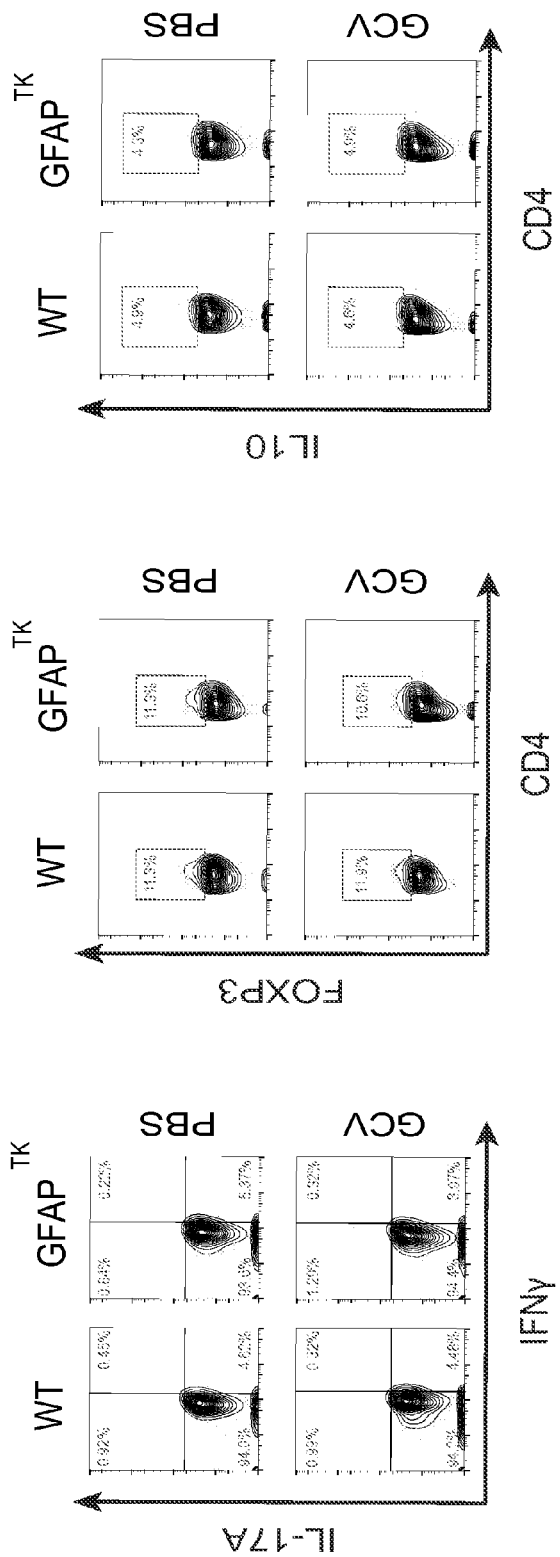
FIG. 9C
FIG. 9D

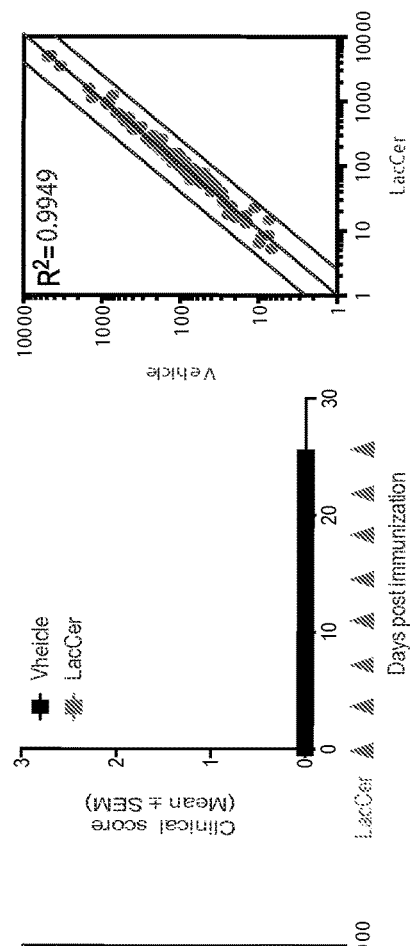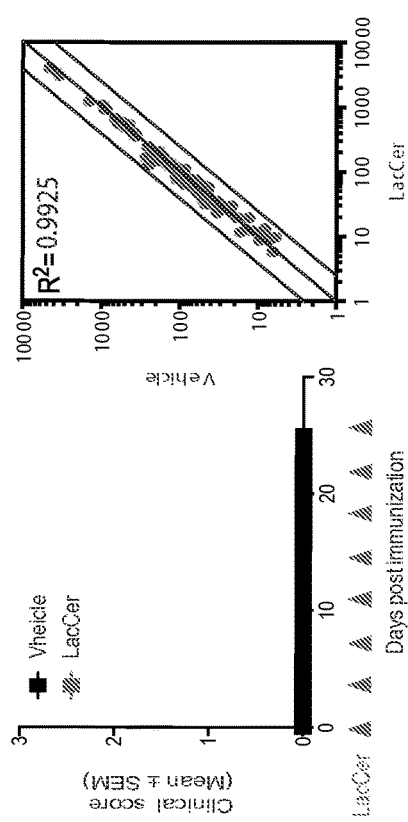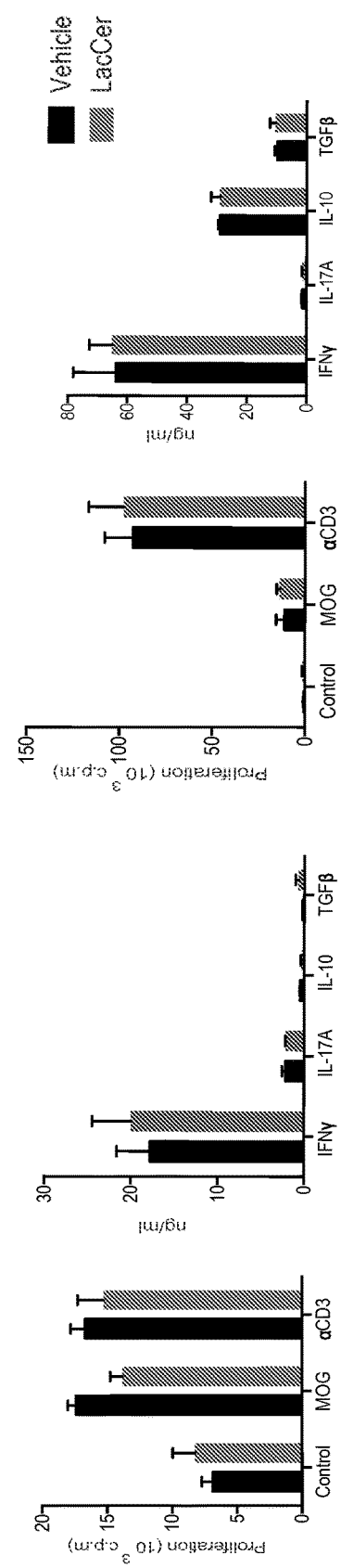
FIG. 12A FIG. 12B FIG. 12C FIG. 12D FIG. 12E

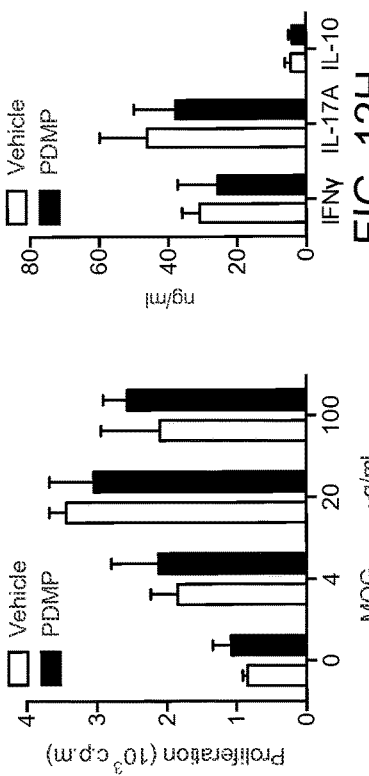
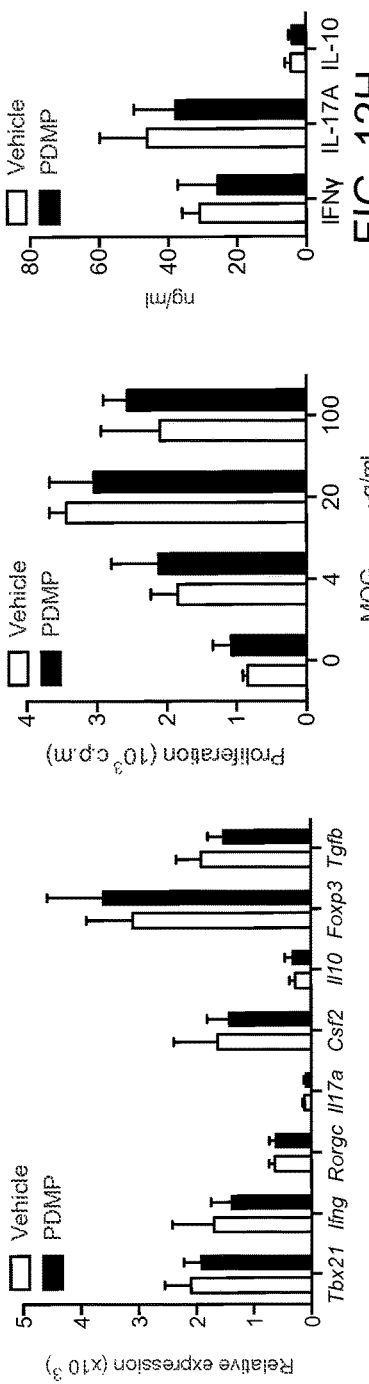
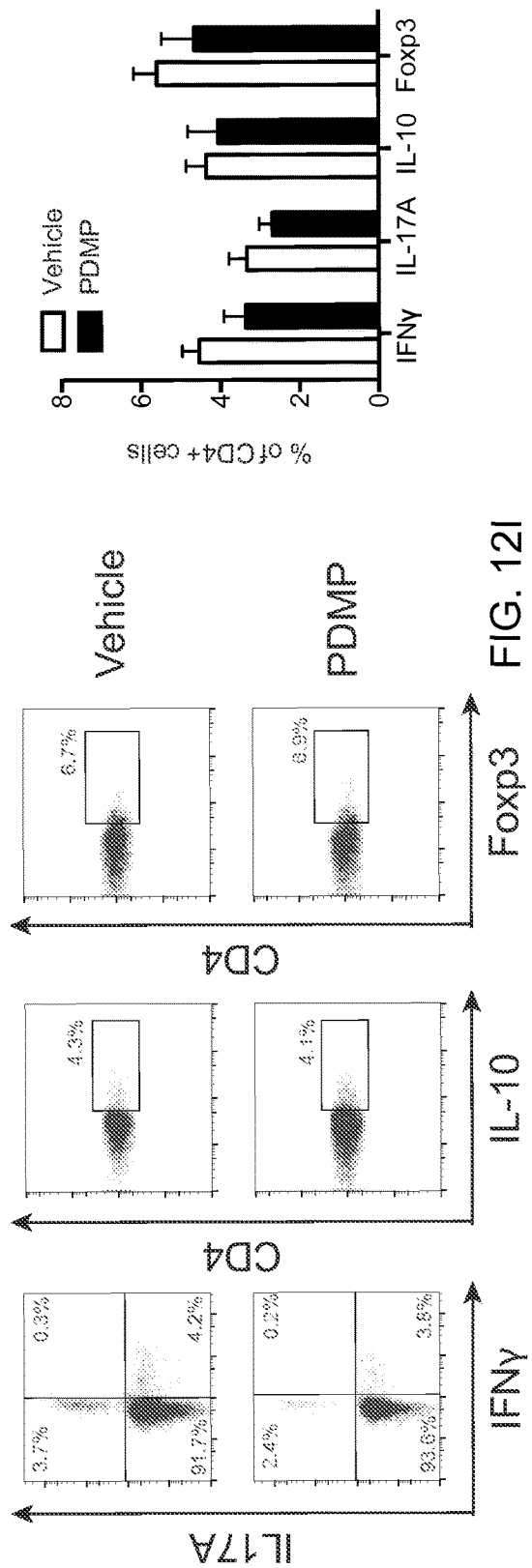

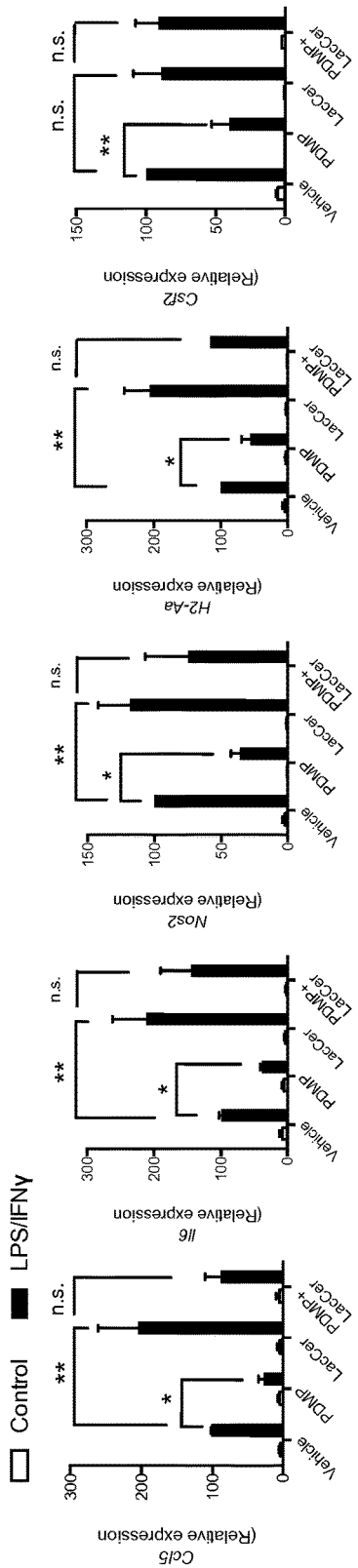
FIG. 14A
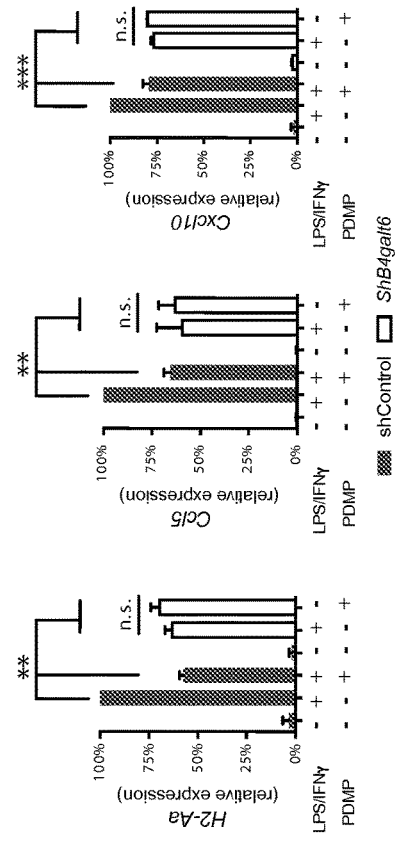
FIG. 14C
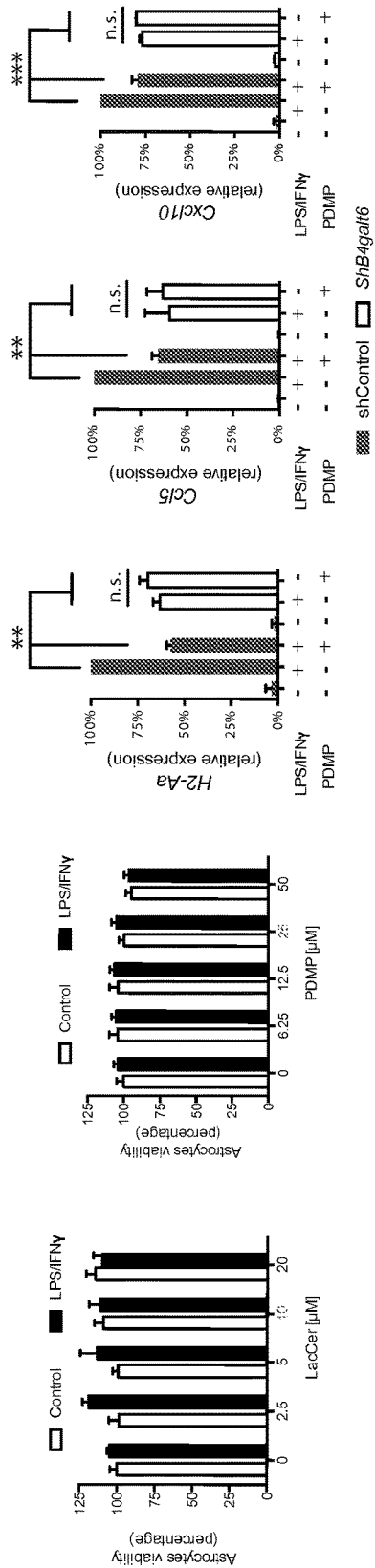
FIG. 14D
FIG. 14B

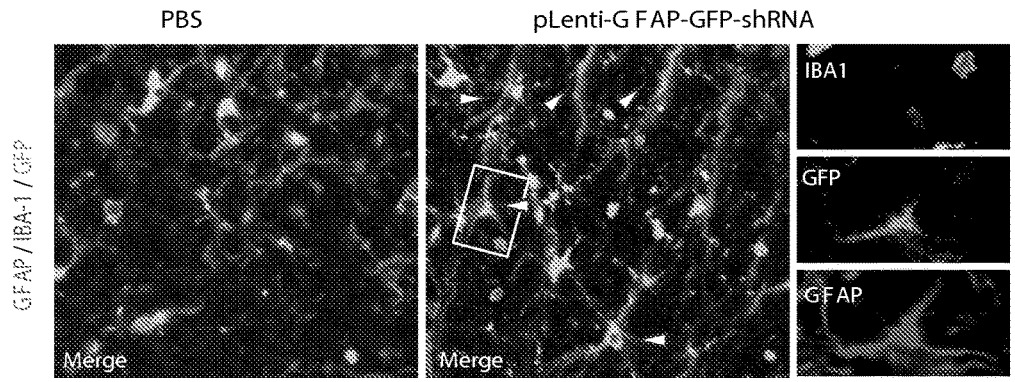
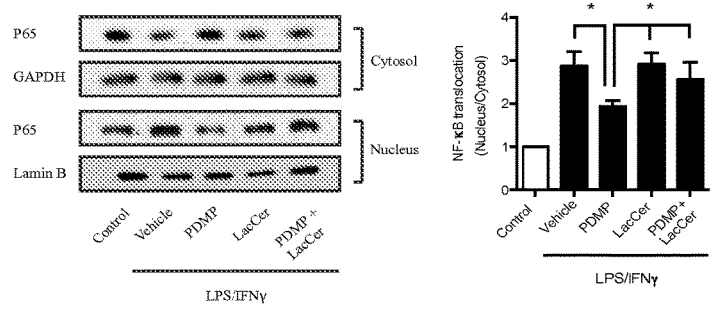
FIG. 14E
FIG. 14F
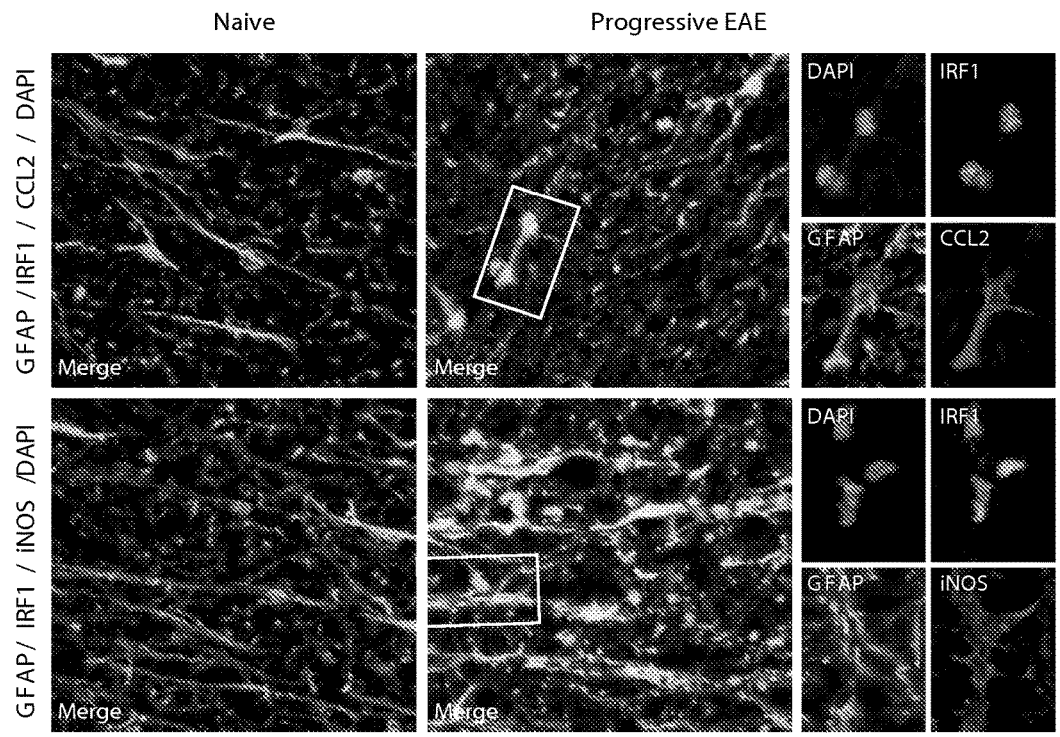
FIG. 14G

TREATING NEURODEGENERATIVE DISEASE

CLAIM OF PRIORITY

This application is a 371 application of PCT/US2014/070099, filed Dec. 12, 2014, which claims the benefit of U.S. Provisional Patent Application Ser. No. 61/963,738, filed on Dec. 12, 2013, and 62/049,813, filed on Sep. 12, 2014. The entire contents of the foregoing are hereby incorporated by reference.

FEDERALLY SPONSORED RESEARCH OR DEVELOPMENT

This invention was made with Government support under Grant Nos. AI075285, and AI093903 awarded by the National Institutes of Health. The Government has certain rights in the invention.

TECHNICAL FIELD

The invention relates to methods of diagnosing or determining risk of developing progressive multiple sclerosis (MS), e.g., primary progressive multiple sclerosis (PPMS) or secondary progressive multiple sclerosis (SPMS) in a subject, based on detecting a level of lactosylceramide (LacCer), and methods of treating progressive MS, based on administration of an inhibitor of LacCer synthesis.

BACKGROUND

Astrocytes are the most abundant cells in the central nervous system (CNS). Under normal conditions astrocytes modulate synaptic activity, and provide nutrients and support needed for neuronal survival[1-4]. In the context of neuroinflammation, astrocytes control CNS infiltration by peripheral pro-inflammatory leukocytes[5-8] and regulate the activity of microglia, oligodendrocytes and cells of the adaptive immune system[9]. Thus, it is important to characterize the mechanisms regulating astrocyte activation during CNS inflammation, as well as potential targets for the therapeutic modulation of astrocyte activity.

Multiple sclerosis (MS) is a chronic demyelinating autoimmune disease of the CNS. In most patients, MS initially presents a relapsing-remitting clinical course (relapsing-remitting MS, RRMS) that is followed by a progressive phase (secondary progressive MS, SPMS) characterized by a continued and irreversible accumulation of disability in which available treatments show limited efficacy[10]. Recent findings suggest that the local CNS innate immune response drives disease progression in SPMS[9,11,12].

SUMMARY

As described herein, lactosylceramide (LacCer) levels are up-regulated in the CNS during chronic experimental autoimmune encephalomyelitis (EAE), an experimental model of multiple sclerosis (MS). LacCer synthesized by β-1,4-galactosyltransferase 6 (B4GALT6) in astrocytes acts in an autocrine manner to trigger transcriptional programs that promote the recruitment and activation of CNS-infiltrating monocytes and microglia, and neurodegeneration. In addition, increased B4GALT6 expression and LacCer levels were detected in CNS MS lesions in human patients. Finally, the inhibition of LacCer synthesis suppressed local CNS innate immunity and neurodegeneration in EAE, and interfered with the activation of human astrocytes in vitro. Thus, B4GALT6 is a therapeutic target for MS and other neuroinflammatory disorders.

Thus, in a first aspect, the invention provides methods for diagnosing or determining risk of developing secondary progressive multiple sclerosis (SPMS) in a subject. The methods include detecting a level of lactosylceramide (LacCer) in a sample from a subject; comparing the level of LacCer in the sample to a reference level of LacCer that represents a level of LacCer in a control subject who has or is at risk of developing SPMS, and diagnosing SPMS in a subject or identifying a subject as at risk of developing SPMS when the level of LacCer in the sample is above the reference level. In some embodiments, the methods include administering a treatment for MS, e.g., as known in the art or described herein, to a subject who has been identified as having or at risk of developing SPMS.

In some embodiments, the subject has relapsing remitting multiple sclerosis, and the level indicates that the subject is at risk of developing SPMS. In some embodiments, wherein the subject has an increased risk of developing SPMS within 1, 3, 6, 9, 12 months, 2 years, 3 years, 4 years, or 5 years.

In another aspect, the invention provides methods for treating progressive MS, e.g., primary progressive multiple sclerosis (PPMS) or secondary progressive multiple sclerosis (SPMS) in a subject, by administering to the subject a therapeutically effective amount of an inhibitor of LacCer synthesis. Also provided is the use of inhibitors or LacCer synthesis in treating progressive MS, e.g., primary progressive multiple sclerosis (PPMS) or secondary progressive multiple sclerosis (SPMS) in a subject in need thereof, or in the manufacture of a medicament for the treatment progressive MS, e.g., primary progressive multiple sclerosis (PPMS) or secondary progressive multiple sclerosis (SPMS).

In an additional aspect, the invention provides methods for treating progressive multiple sclerosis (MS) in a subject. The methods include detecting a level of lactosylceramide (LacCer) in a sample from a subject who has or is suspected of having progressive MS; comparing the level of LacCer in the sample to a reference level of LacCer, e.g., a reference level that represents a level of LacCer in a control subject who has or is at risk of developing progressive MS, and administering a treatment comprising administering to the subject a therapeutically effective amount of an inhibitor of LacCer synthesis to a subject who has a level of LacCer above the reference level. In some embodiments, the methods include administering another treatment for MS, e.g., as known in the art or described herein, e.g., a standard treatment for MS.

In a further aspect, the invention features methods for selecting a treatment for a subject who has or is suspected of having MS, e.g. progressive MS. The methods include detecting a level of lactosylceramide (LacCer) in a sample from a subject who has or is suspected of having progressive MS; comparing the level of LacCer in the sample to a reference level of LacCer, e.g., a reference level that represents a level of LacCer in a control subject who has or is at risk of developing progressive MS, and selecting a treatment comprising administering to the subject a therapeutically effective amount of an inhibitor of LacCer synthesis to a subject who has a level of LacCer above the reference level. In some embodiments, the methods include administering the treatment for MS, and optionally administering another treatment for MS, e.g., as known in the art or described herein, to a subject who has been identified as having or at risk of developing SPMS.

In some embodiments, the inhibitor of LacCer synthesis is an inhibitor of glucosylceramide (GlcCer) synthesis. In some embodiments, the inhibitor of GlcCer synthesis is selected from the group consisting of 1-(3',4'-ethylenedioxy) phenyl-2-nonanoylamino-3-pyrrolidino-1-propanol; 1-(3', 4'-ethylenedioxy)phenyl-2-octanoylamino-3-pyrrolidino-1-propanol; D-threo-(1R,2R)-phenyl-2-decanoylamino-3-morpholino-1-propanol (PDMP) and analogs thereof including D-PDMP; PPMP (DL-threo-1-Phenyl-2-palmitoylamino-3-morpholino-1-propanol), D-threo-EtDO-P4; ((1R, 2R)-nonanoic acid[2-(2',3'-dihydro-benzo [1,4] dioxin-6'-yl)-2-hydroxy-1-pyrrolidin-1-ylmethyl-ethyl]-amide-L-tartaric acid salt; CCG0203586 (1-hydroxy-3-(pyrrolidin-1-yl)acetamide); Genz-112638 (eliglustat); Genz-529468; deoxynojiromycin-based GlcCer inhibitors; GZ-161; Genz-682452; EXEL-0346; OGT2378; and Genz-123346. In some embodiments, the deoxynojiromycin-based GlcCer inhibitor is N-(5'-adamantane-1'-yl-methoxy)-pentyl-1-deoxynojirimycin (AMP-DNM), N-butyl-deoxynojirimycin (miglustat) or a long-chain N-alkyl derivative of 1,5-dideoxy-1,5-imino-D-glucitol having from nine to about 20 carbon atoms in the alkyl chain. In some embodiments, the N-alkyl substituent is selected from the group consisting of nonyl, decyl, undecyl, dodecyl, tetradecyl, hexadecyl, cis-11-hexadecenyl, octadecyl, cis-13-octadecenyl, and eicosyl.

In some embodiments, the inhibitor of LacCer synthesis is an inhibitor of B4GALT6 selected from the group consisting of a small molecule, an inhibitory nucleic acid targeting B4GALT6, or an inhibitory antibody that binds specifically to B4GALT6 and inhibits LacCer synthesis.

In some embodiments, the inhibitory nucleic acid targeting B4GALT6 is selected from the group consisting of antisense, siRNA, shRNA, and miRNA.

In some embodiments, the methods include administering an inhibitor of B4GALT6 and an inhibitor of GlcCer synthesis.

In some embodiments, the methods include selecting the subject on the basis that the subject has progressive MS, e.g., PPMS or SPMS.

In some embodiments, the methods include administering an activator of glucocerebrosidase. In some embodiments, the activator of glucocerebrosidase is Saposin C or an active fragment thereof; NCGC00182186 (5-cyclopropylidene-7-(difluoromethyl)-N-(2-phenylsulfanylphenyl)-1H-pyrazolo [1,5-a]pyrimidine-3-carboxamide); NCGC00182510 ([2-(tert-butylamino)-2-oxoethyl] 2-[2-(4-bromoanilino)-2-oxoethoxy]benzoate) or phosphatidylserine.

In some embodiments, the methods include administering a treatment, e.g., a compound, orally, nasally, intravenously, or intrathecally.

In some embodiments, the subject has SPMS and/or is selected on the basis that they have SPMS.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1a-l. B4GALT6 activity controls CNS inflammation and neurodegeneration. (a, b) EAE scores in wild type (WT) and GFAP-TK transgenic (GFAP$^{TK}$) F1 hybrid mice (mean and s.e.m.). Right panel, linear-regression curve; dashed lines indicate 95% confidence interval of the regression line. Mice were treated daily with Ganciclovir (GCV, 25 mg/kg) or vehicle (PBS) as indicated (black bar). Representative data of three independent experiments with n≥7 mice/group. (a) Mice were pretreated 7 days before EAE induction and continuously until day 15, (b) or were treated only during the progressive phase (days 30-50). (c) Heatmap depicting the differential mRNA expression profiles in astrocytes isolated from the CNS of naïve NOD mice, or during the acute or the progressive phase of NOD EAE, as detected by Nanostring nCounter analysis; Representative data of three independent experiments. (d) Heatmap depicting a unique gene cluster specifically up-regulated during the progressive phase of EAE. In the original, most of the rightmost three columns were high-expression, while the middle and left-most were low expression. (e) qPCR analysis of b4galt6 expression in microglia or astrocytes from naïve or EAE NOD mice; expression normalized to gapdh and presented relative to that of cells from naïve mice. Representative data of three independent experiments, statistical analysis by Student's t-test. (f) Quantification of lactosylceramide (LacCer) in the CNS of naïve or EAE NOD mice, relative to net tissue weight. Representative data of three independent experiments with n≥15 samples per condition, statistical analysis by Student's t-test. (g, h) EAE clinical scores in C57BL/6 (g) and NOD (h) mice following administration of LacCer (10 µg per mouse) or vehicle as indicated by arrows or bar. Representative data of two independent experiments with n≥8 mice/group. Statistical analysis as in (a). (g) EAE scores following LacCer or vehicle administration together with the MOG$_{(35-55)}$ peptide to C57BL/6 mice during EAE induction, and also intraperitoneally (i.p.) every other 3 days henceforth (mean and s.e.m.). (h) EAE scores following LacCer or vehicle administration initiated at day 35 after EAE induction (progressive phase). (i) PDMP inhibits LacCer synthesis by B4GALT6. (j) Quantification of LacCer levels in the CNS of naïve or EAE NOD mice treated with PDMP or vehicle as shown in (k). (k) Clinical scores of EAE in NOD mice treated with PDMP or vehicle, administered daily (20 mg/kg given i.p. twice a day) from day 40 after EAE induction (progressive phase) for the duration of the experiment Representative data of three independent experiments with n≥8 mice/group). (l) Histopathology analysis of lumbar spinal cord sections from EAE NOD mice treated with PDMP or vehicle as in (k) and stained with Luxol fast blue or Bielschowsky's silver stain for analysis of demyelination or axonal loss, respectively. Representative data of two independent experiments with n≥6 mice/group (mean and s.e.m.). *P<0.05, P<0.01, *P<0.001, n.s. not significant.

FIGS. 2a-e. B4GALT6 inhibition suppresses astrocyte activation during EAE. (a) Heatmap depicting mRNA expression, as detected by Nanostring nCounter analysis, in astrocytes isolated from naïve or EAE NOD mice treated with PDMP or vehicle (vehicle). Upper panels, histogram presentation of normalized gene expression in each gene cluster. Representative data of three independent experiments, statistical analysis by Student's t-test. In the original of the left hand graph, the left column was mostly high expression, the center column was low expression, and the right column was mixed; in the original of the right hand graph, the left column was mostly low expression, the center column was mostly high expression, and the right column was mixed. (b) qPCR analysis of ccl2, ccl5, cxcl10, il1b, nos2, opn, H2-Aa, vim and tir2 expression in astrocytes isolated from naïve and EAE NOD mice treated with vehicle or PDMP; expression is presented relative gapdh. Representative data of three independent experiments, statistical analysis by Student's t-test. (c) Relative expression (to NOD naïve group) of genes associated with the control of myelination (Table 2) in astrocytes isolated from EAE NOD mice treated with vehicle or PDMP. Representative data of three independent experiments. Statistical analysis by Student's t-test. (d, e) qPCR analysis of Irf1 (d) and Relb (e) expression performed as in (b). All data presented as mean and s.e.m. *P<0.05, P<0.01, *P<0.001 and n.s. not significant.

FIGS. 3a-m. LacCer produced by B4GALT6 acts in an autocrine manner to boost astrocyte activation. Cultured astrocytes were pre-treated for 1 h with PDMP (25 µM), LacCer (10 µM), both (LacCer+PDMP), or vehicle (vehicle), followed by activation with lipopolysaccharide (100 ng/ml) and Interferon-γ (100 Units/ml) (LPS/IFNγ) or left un-treated (control). (a) Heatmap depicting mRNA expression, as detected by Nanostring nCounter analysis, in astrocytes stimulated with LPS/IFNγ. Representative data of three independent experiments. (b) Histogram presentation of the normalized gene expression presented in (a), statistical analysis by one-way ANOVA followed by Tukey post-hoc analysis. (c-i) The expression of B4galt5 (shB4galt5), B4galt6 (shB4galt6) or non-targeting shRNA (ShControl) in C8-D30 astrocytes was knocked-down using verified shRNA (n≥4). (c) qRT analysis of B4galt5 and B4galt6 mRNA expression. (d-f) astrocytes were activated as in (a) and mRNA expression for (d) H2-Aa, (e) Ccl5 and (f) Cxcl10 was determined; expression is presented relative to house keeping gene (Gapdh) (n≥4). (g) Schematic map of the astrocyte-specific shRNA lentiviral vector. (h-j) i.c.v. injection of astrocyte-specific shB4galt6 lentivirus ameliorates disease severity. NOD mice were injected i.c.v. with 1×10$^7$ IU of shControl, shB4galt5 or shB4galt6 lentivirus, at day 35 after EAE induction (progressive phase). n=10 mice per group (h, i) 10 days after i.c.v. injection experiment was terminated and (h) b4galt5 and b4galt6 expression levels were determined by qPCR in astrocytes isolated from naïve or EAE NOD mice; expression normalized to gapdh and presented relative to that of cells from naïve mice. Representative data of two independent experiments, Statistical analysis by one-way ANOVA, followed by Tukey post-hoc analysis. (i) LacCer levels were quantified of in the CNS of naïve or EAE NOD mice treated as shown in (j). Statistical analysis by one-way ANOVA, followed by Tukey post-hoc analysis. (j) EAE clinical scores. Representative data of two independent experiments. Statistical analysis as in (FIG. 1a). (k) Cultured primary astrocytes were pre-treated for 1 h with PDMP (25 µM), LacCer (10 µM), both (LacCer+PDMP), or vehicle control (vehicle), followed by activation with LPS/IFNγ for 45 min, or left un-treated (control, Con). IRF-1 and Lamin B expression in the nuclear fraction analyzed by western blot and the degree of IRF-1 translocation to the nucleus was assessed by the ratio between the expression of IRF-1 and Lamin-B in the nuclear fractions following densitometric quantification on four independent experiments (right panel). Statistical analysis by one-way ANOVA, followed by Tukey post-hoc analysis. (l) ChIP analysis of the interaction of NF-κB, and IRF-1 with the) nos2 promoter in primary cultured astrocytes. Experimental design and data analysis as in (FIG. 4c). Data from two independent experiments (m) qPCR analysis of the expression of nos2, csf2, ccl2, ccl5, il6, and tlr2 in astrocyte cultures established from WT or IRF-1 deficient (IRF-1 KO) mice, pre-treated with LacCer or vehicle, and activated with LPS/IFNγ. Mean gene induction in response to LacCer treatment in LPS/IFNγ-activated cells from 5 independent experiments. Statistical analysis by Student's t-test. All data presented as mean and s.e.m. *P<0.05, P<0.01, *P<0.01 and n.s. not significant.

FIGS. 4a-m. B4GALT6 regulates ccl2 transcriptional activity in astrocytes. (a) Murine ccl2 promoter. (b) Luciferase activity in 293T cells transfected with the ccl2 luciferase reporter plus one of the following constructs encoding IRF-1, p65 or an empty control vector (Empty). Results are relative to secreted alkaline phosphatase activity, presented as fold induction from empty vector. Data from three independent experiments, statistical analysis by Student's t-test. (c) ChIP analysis of the interaction of NF-κB, and IRF-1 with the ccl2 promoter in primary cultured astrocytes, pre-treated with PDMP and LacCer and activated with LPS/IFNγ (as in FIG. 3), 2 hours following LPS/IFNγ induction. (d-h) Recruitment of inflammatory monocytes (defined either as of CD11b$^+$ Ly6C$^{high}$ or CD11b$^+$CD45$^{high}$ cells) to the CNS of EAE NOD mice treated with PDMP or vehicle, as in (FIG. 1k), analyzed by flow cytometry and presented as cell frequency (e, g) and total cell numbers (f, h). Representative data of three independent experiments. Statistical analysis by Student's t-test. (i) The frequency and number of CD11b$^+$ Ly6C$^{high}$ monocytes as determined in the CNS 10 days after the i.c.v. injection of astrocytes-specific shRNA lentivirus as in (FIG. 3j). Representative data of two independent experiments. Statistical analysis by one-way ANOVA, followed by Tukey post-hoc analysis. (j) monocytes were pre-treated for 1 h with PDMP, LacCer, both (LacCer+PDMP), or vehicle, and monocytes chemotaxis was measured using a transwell chamber system. CCL2 or PBS were added to the lower compartment, and 3 h later cell viability (j, k) and the number of the migrating monocytes (l) and cell viability were determined. Migration data is presented as fold from control, and cell viability as percentage from control. Working concentrations are marked in red. Representative data of four independent experiments. (m) CD11b$^+$ Ly6C$^{high}$ monocytes were treated with PDMP, LacCer or vehicle, followed by activation with LPS/IFNγ for 6 h or left un-treated (control) as in (FIG. 3a). mRNA expression was determined by nCounter Nanostring analysis. Statistical analysis by two ANOVA showed no significance effect of the LacCer or PDMP treatments on the monocytes migration. For all data, data presented as mean and s.e.m. *P<0.05, P<0.01, *P<0.001 and n.s. not significant.

FIGS. 5a-m. B4GALT6 in astrocytes regulates the activation of microglia and CNS-infiltrating monocytes. (a) Heatmap depicting mRNA expression, as determined by nCounter Nanostring analysis, in microglia from naïve or EAE NOD mice treated with PDMP or vehicle. Representative data of three independent experiments. Statistical analysis by Student's t-test. (b) qPCR analysis of ccl5, il1b, opn, nos2, cd40, and H2-Aa gene expression relative to Gapdh. (c, d) Mean normalized expression of genes associated with M1- or M2-phenotype in microglia (Table 3) (c) and Ly6C$^{high}$ monocytes (d). Statistical analysis by Student's t-test. (e-h) primary microglia were pre-treated with PDMP, LacCer, or vehicle, followed by activation with LPS/IFNγ for 6 h or left un-treated (control) as in (FIG. 3a). mRNA expression was determined by nCounter Nanostring analysis (e, g), and microglial viability was determined (f, h). Representative data of five independent experiments. (i)

Mixed glia cultures were treated with mild trypsin/EDTA (T/E) to remove the astrocyte monolayer leaving only the microglia attached to the plate, or left un-treated. Cultures were pre-treated with PDMP, LacCer or vehicle, and activated with LPS/IFNγ for 6 h. Following activation, both cultures were washed, and incubated with mild T/E to remove the astrocytes; thus, leaving only the microglia (MG) attached to the plates. RNA was harvested from microglia treated in the absence [MG (pure)] or presence [MG (mixed)] of astrocytes and gene expression was analyzed by qPCR for the expression ccl2, ccl5 and nos2 relative to gapdh. Data present the relative effect of PDMP (left panel) or LacCer (right panel) pre-treatment on LPS/IFNγ-triggered gene induction, from five independent experiments. Statistical analysis by Student's t-test. (j) Mixed glia were pre-treated with indicated blocking antibodies or appropriate isotype controls (25 µg/ml) and LacCer (1004) or vehicle control, and then activated with LPS/IFNγ for 6 h. Microglia were isolated as in (i), and microglial-nos2 expression was determined by qRT relative to gapdh and presented as in (i). Representative data of three independent experiments. (k) ChIP analysis of the interaction of NF-κB, and IRF-1 with the csf2 promoter in primary cultured astrocytes. (l, m) Expression csf2 in astrocytes (l) and nos2 in microglial cells (m) isolated form the CNS of chronic EAE NOD mice, 10 days after the i.c.v. injection of astrocytes-specific shRNA lentivirus as in (FIG. 3j). Data from two independent experiments. For all data, means and s.e.m. are shown. *$P<0.05$, $P<0.01$, *$P<0.001$ and n.s. not significant.

FIG. 6a-d. B4GALT5 and B4GALT6 and LacCer levels are up-regulated in MS lesions. Autopsy samples were obtained from lesions (n=10) or NAWM (n=5) from MS, non-MS CNS inflammatory diseases (NMSCID, including viral encephalitis, Rasmussen's encephalitis and ADEM, n=5) patients and healthy controls (n=6). (a) qPCR analysis of B4GALT5 and B4GALT6 mRNA expression in CNS samples relative to ACTB. (b) IF analysis of B4GALT6, CCL2 and iNOS in GFAP+ astrocytes in NAWM and Lesion of MS patients. (c) LacCer levels determined in CNS samples, relative to protein content. Statistical analysis by one-way ANOVA, followed by Tukey post-hoc analysis. (d) Primary human astrocytes were pre-treated with PDMP (25 µM) or vehicle, and activated with IL-1β (10 ng/ml) or Poly (I:C) (10 µg/ml) or left untreated (control). RNA was harvested 6 h later and the expression of CCL2, CCL5, COX2, IL6, NOS2, and TLR2 was analyzed by qPCR relative to ACTB in 3 independent experiments. Statistical analysis by Student's t-test. Data presented are mean and s.e.m. *$P<0.05$, $P<0.01$ and *$P<0.001$.

Figure 7B:
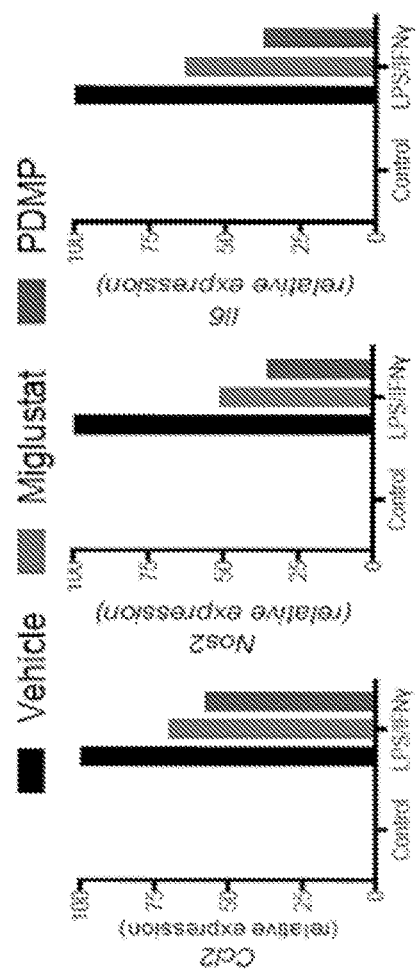
Figure 7A:
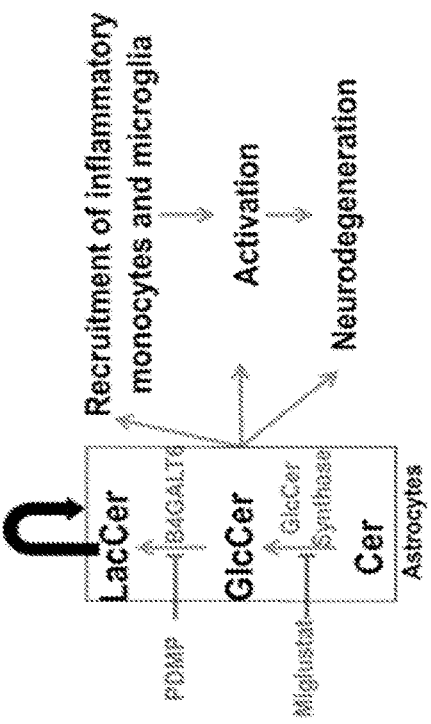

FIGS. 7a-b. Therapeutic potential of Miglustat in SPMS. A. Role of B4GALT6/LacCer in CNS inflammation. B. Effect of B4GALT6 inhibition by PDMP or GlcCer synthase inhibition with Miglustat on primary mouse astrocytes activated with LPS and IFNγ (LPS/IFNγ).

Figure 8A:
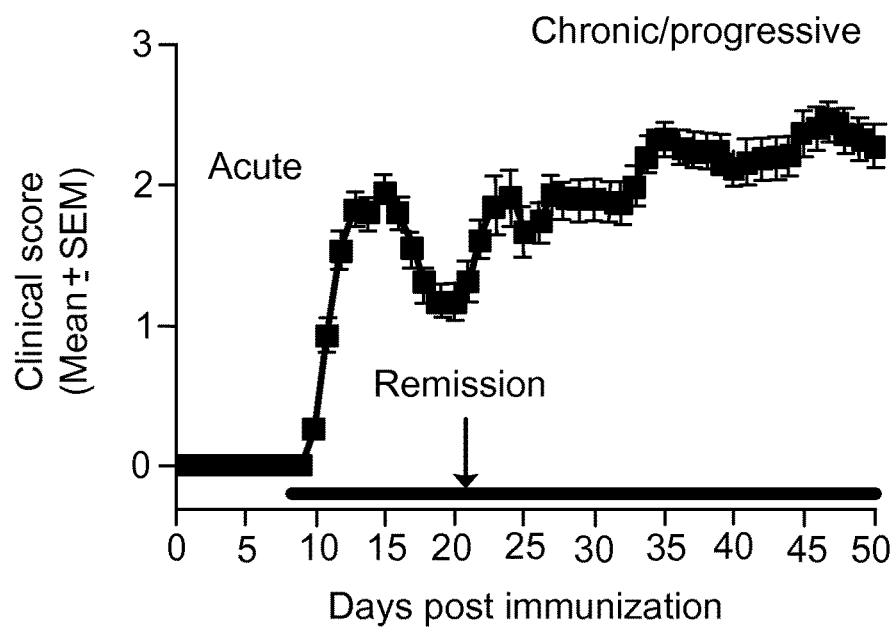
Figure 8A:
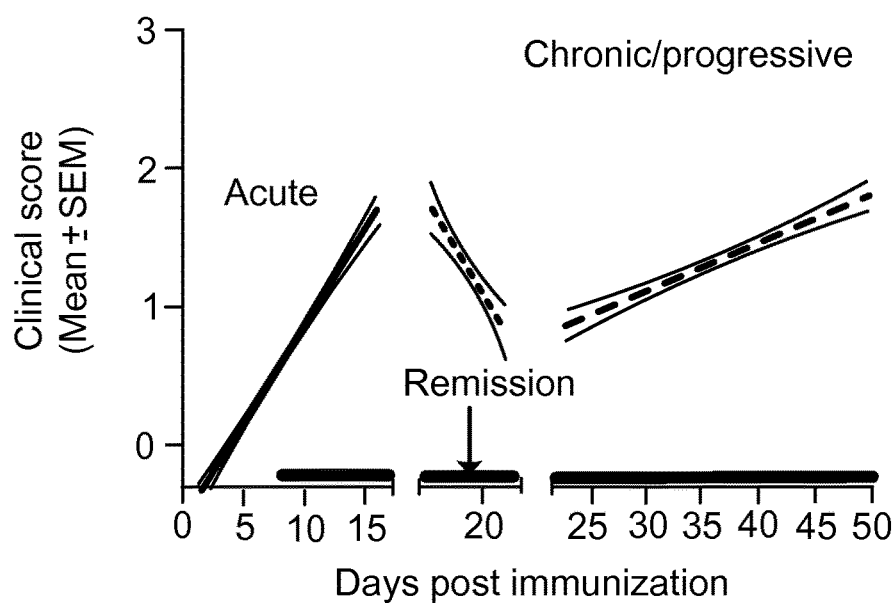
Figure 8B:
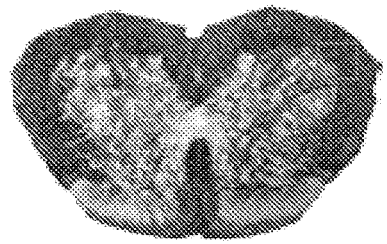
Figure 8B:
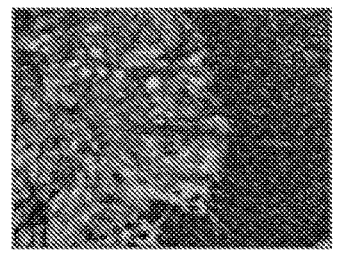
Figure 8B:
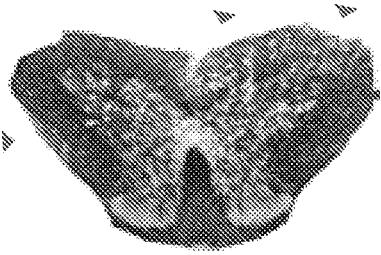
Figure 8B:
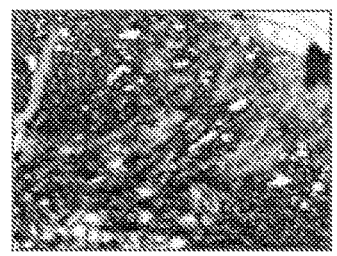
Figure 8C:
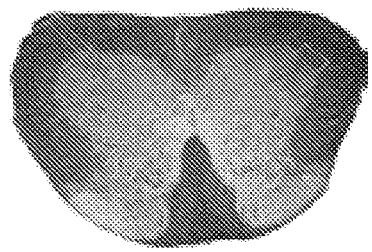
Figure 8C:
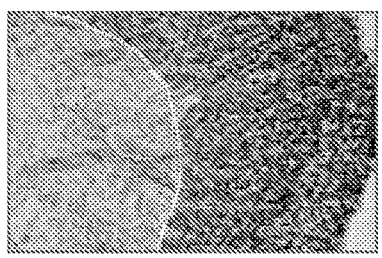
Figure 8C:
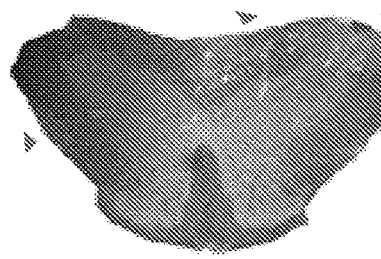
Figure 8C:
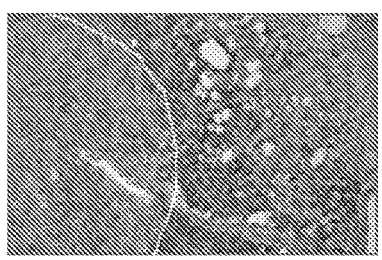

FIGS. 8a-c. F1 hybrid mice develop chronic progressive EAE. (a) Clinical scores of NOD C57BL/6 F1 hybrid mice EAE are presented as means and s.e.m. Right panel, linear-regression curve; dashed lines indicate 95% confidence interval of the regression line. Data are representative of seven independent experiments (means and s.e.m.) (n≥15 mice/group). (b, c) Histopathology analysis. Lumbar spinal cord sections of EAE induced F1 mice, were taken at the experiment endpoint and stained with (b) Bielschowsky's silver stain for axonal density or (c) Luxol fast blue for myelin content. Data are representative of three independent experiments.

FIGS. 9a-d. Depletion of reactive astrocytes reduces the recruitment of peripheral leukocytes to the CNS. (a-d). EAE was induced in WT or GFAP$^{TK}$ F1 hybrid mice and Ganciclovir (GCV) or vehicle control (PBS) was administered as in FIG. 1b. Data are representative of three independent experiments with n≥7 mice/group (means and s.e.m.). (a) Effect of GCV administration on reactive astrocytes detected by GFAP staining (b) Recruitment of monocytes (red gate) and lymphocytes (green gate) to the CNS assessed by FACS. Data are representative of three independent experiments. Statistical analysis by Student's t-test. (c, d) Effect of the depletion of reactive astrocytes during the chronic phase of EAE on the recall proliferative response to MOG$_{(35-55)}$ or anti-CD3 (c) and the expression of IFN-γ, IL-17A, Foxp3 and IL-10 in splenic CD4+ T cells (d). *$P<0.05$, and (n.s) not significant.

FIGS. 10a-g. Isolation of adult astrocytes from CNS. (a-c) Isolation of astrocytes from adult mice. (a) Exclusion of dead cells. (b) Exclusion of immune cells based on CD11b$^+$ staining (microglia and monocytes, blue gate) or CD45$^+$ CD11b$^{neg}$ (lymphocytes, green gate). (c) Contaminating immune cells and oligodendrocytes were removed from the "non-immune" cell fraction (b, red gate) using a dump channel (as detailed in the materials and methods). The negative fraction (c, Red gate), was designated as the astrocyte-enriched fraction and used for intracellular staining (d) or mRNA analysis (e-f). Total cells, the microglia/monocyte and lymphocyte fractions, as well as GFP$^+$ astrocytes from GFAP-GFP FVB mice were also taken for mRNA analysis. (d) GFAP expression in the astrocyte-enriched fraction (black—GFAP staining, gray—Isotype control). (e-f) qPCR analysis of purity in enriched astrocyte, microglia/monocyte, lymphocyte and brain fractions. (e) Expression of the astrocyte markers gfap, aldh1l1 and aqp4. (f) Expression of immune cell markers: microglia/monocytes cells (Cd11b, F4/80), dendritic cells (Cd11c), NK cells (Klrb1c), T-cells (Cd3), B-cells (Cd19). (g) Expression of oligodendrocyte (mog, mbp), and neuron (Syt1, Snap25) markers. Data are representative of three independent experiments (mean and s.e.m.), (n≥5 mice/group).

FIGS. 11a-d. LacCer synthases expression is up-regulated in astrocytes during chronic NOD EAE. (a) Immunostaining of B4GALT6 expression in GFAP+ astrocytes in white matter, gray-matter, and perivascular glia limitans (CD31 was used as a marker for endothelial cells). (b) Immunostaining of B4GALT6 expression in NESTIN+ Neural progenitors. qRT analysis of B4galt5 mRNA expression in (c) astrocytes or (d) microglia isolated from the CNS of naïve NOD mice, or during the chronic phase of EAE; Expression is presented relative to housekeeping gene (Gapdh). Data are representative of four experiments. Data presented are means and s.e.m. Statistical analysis was performed by Student's t-test, *$P<0.05$, and (n.s) no significance.

FIGS. 12a-i. B4GALT6 and LacCer do not affect the peripheral T-cell response during EAE. (a) Naïve C57BL/6 (Left panel) and NOD (right panel) mice were treated with LacCer (10 µg per mouse) or vehicle as indicated by red arrows, and EAE clinical scores was recorded. At experimental end point (day 25), astrocytes were isolated and their transcriptional profile was determined by nCounter Nanostring analysis. (b-e) EAE was induced in C57BL/6 (b, c) or NOD mice (d, e) and LacCer or vehicle were administrated as in FIGS. 1g and 1h, respectively. Splenic T-cell recall response to MOG$_{(35-55)}$ (20 µg/ml); proliferation (b, d) and secretion of IL-17A, IFN-γ and IL-10 cytokines (c, e). Data are representative of two independent experiments with ≥8 mice/group (mean and s.e.m.). (f-i) EAE NOD mice were treated with PDMP or vehicle during the chronic phase as in FIG. 1K. Data are representative of three independent experiments with n≥8 mice/group (mean and s.e.m.). (f) qPCR analysis of the expression of tbx21, ifng, rorc, il17A, csf2, il10, foxp3, and tgfb1 mRNA of CD3$^+$CD4$^+$ T-cells isolated from the CNS; expression is presented relative to gapdh. (g, h) Recall response to MOG$_{(35-55)}$ (20 μg/ml); proliferation (g) and secretion of IL-17A, IFN-γ and IL-10 cytokines (h). (i) Expression of IFN-γ, IL-17A, Foxp3 and IL-10 by splenic CD3$^+$CD4$^+$ T cells (mean and s.e.m.).

Figure 13:
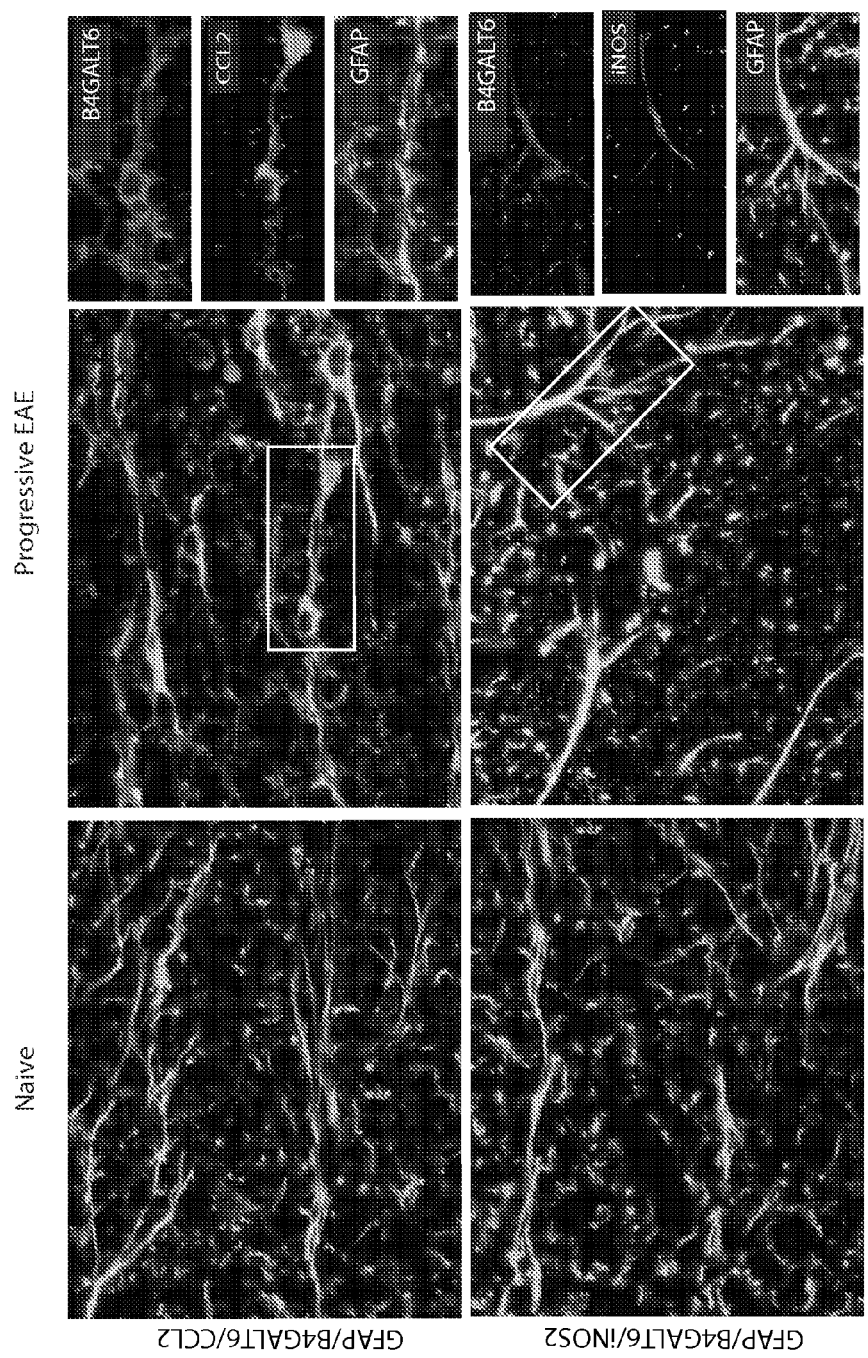

FIG. 13. CCL-2 and iNOS are co-expressed by B4GALT6$^+$ GFAP$^+$ astrocytes. Immunostaining studies identified the expression of CCL-2 or iNOS in B4GALT6$^+$ GFAP$^+$ astrocytes during chronic EAE, but not in naïve spinal cord sections. Representative data of two independent experiments, 6 animals/group were used.

FIGS. 14a-g. B4GALT6 directly controls astrocyte activation. (a) Cultured astrocytes were pre-treated for 1 h with PDMP (25 μM), LacCer (10 μM), both (LacCer+PDMP), or vehicle control (vehicle), followed by activation with LPS/IFNγ for 6 h, or left un-treated (control, Con). mRNA expression was analyzed 6 h following activation. qPCR analysis of the expression of cc/5, csf2, nos2, il6, H2-Aa, and tlr2 presented relative to gapdh. Statistical analysis by one-way ANOVA, followed by Tukey post-hoc analysis. (b, c) Cultured astrocytes were pre-treated for 1 h with LacCer (b) or PDMP (c), at indicated concentrations, followed by activation with LPS/IFNγ, or left un-treated (control, Con). Cell viability was determined 6 h after activation. Statistical analysis by one-way ANOVA reveled no significant cells death. Working concentrations (as in a) are marked in red. (d) The expression of B4galt6 (shB4galt6) or non-targeting shRNA (ShControl) in primary astrocytes was knocked-down using verified shRNA. Astrocytes were then pre-treated for 1 h with PDMP, or vehicle control (vehicle), followed by activation with LPS/IFNγ for 6 h, or left un-treated (control, Con). mRNA expression for H2-Aa, Ccl5 and Cxcl10 was determined; expression is presented as fold induction relative to housekeeping gene (Gapdh). Statistical analysis by one-way ANOVA, followed by Tukey post-hoc analysis (n≥3). (e) Immunostaining analysis of spinal cord slices from Mock- or Lentivirus-infected mice identify GFP+ expression only in GFAP$^+$ astrocytes. Representative data of two independent experiments, at least six animals/group were used. (f) NF-κB (P65), GAPDH, and Lamin B expression, in cytoplasmic and nuclear fractions analyzed by western blot. The degree of NF-κB translocation to the nucleus was assessed by the ratio between the expression of P65 in nuclear and cytoplasmic fractions following densitometric quantification on four independent experiments (Right panel). Statistical analysis by one-way ANOVA, followed by Tukey post-hoc analysis. Data are from five independent experiments (mean and s.e.m.) *P<0.05, and **P<0.01. (g) Expression of CCL-2 or iNOS in IRF-1$^+$ GFAP$^+$ astrocytes determined by IF during chronic EAE. Representative data of two independent experiments, 6 animals/group were used.

Figure 15A:
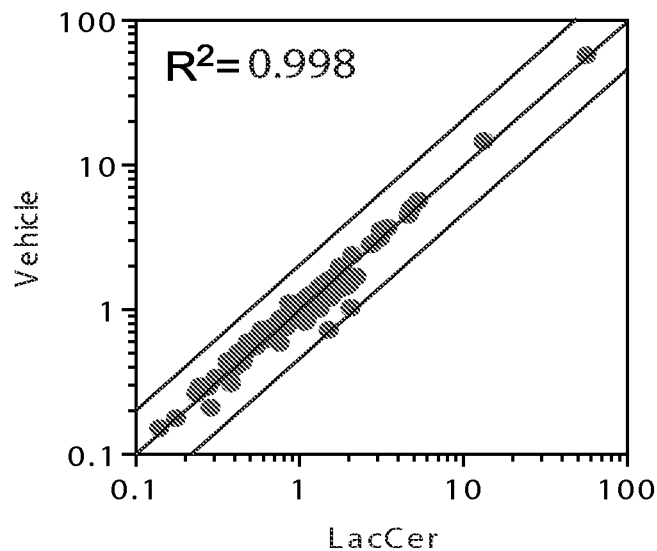
Figure 15B:
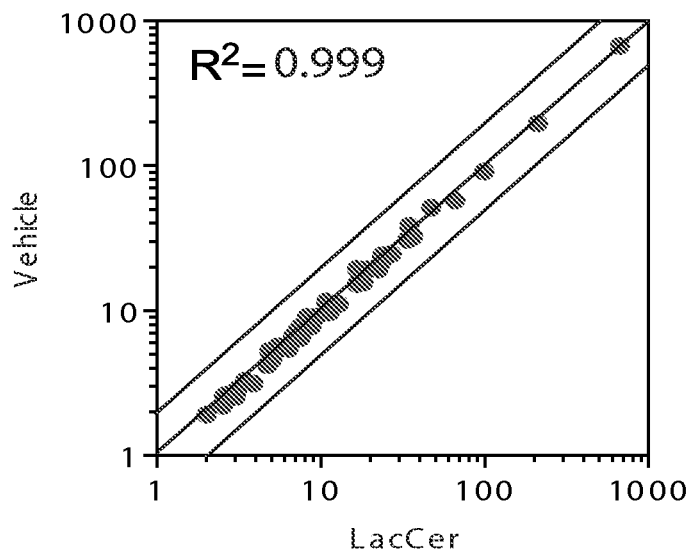

FIGS. 15a-b. LacCer does not affect the transcriptional response of primary leptomeningeal phagocytes and choroid plexus cells. Leptomeningeal phagocytes (a) and choroid plexus cells (b) were pre-treated for 1 h with LacCer (10 μM), or vehicle control (vehicle), followed by activation with LPS/IFNγ for 6 h, or left un-treated (control, Con). mRNA expression was was determined by nCounter Nanostring analysis. Representative data of two independent experiments.

Figure 16:
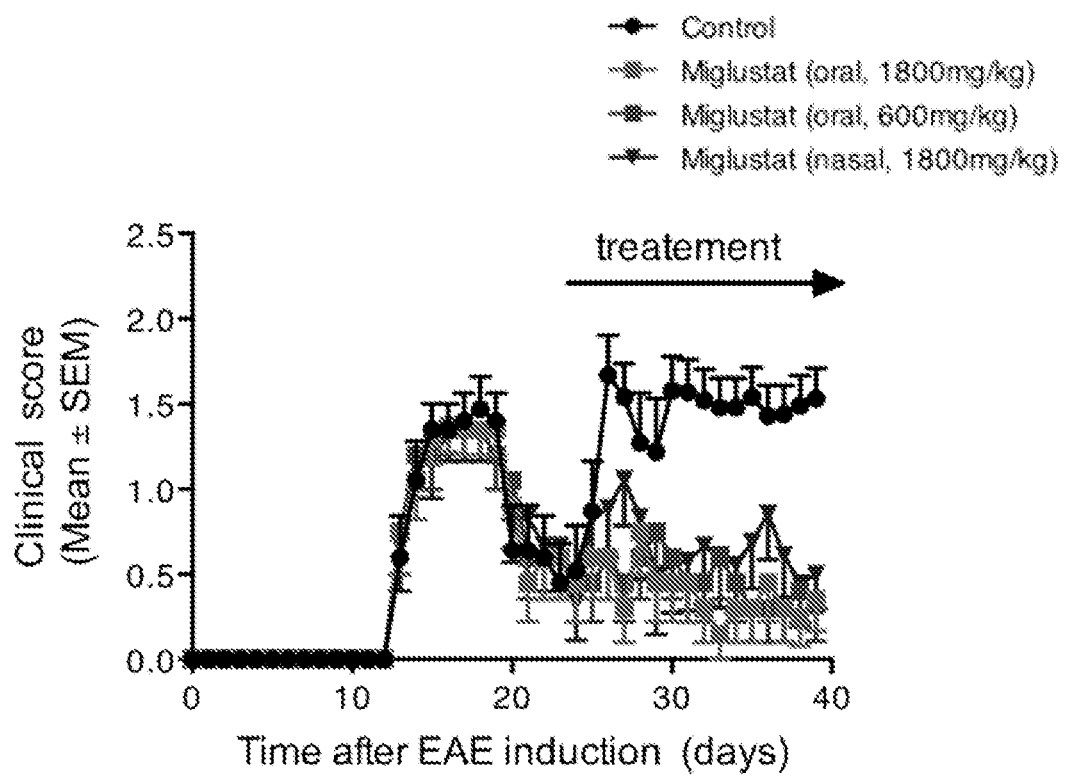
Figure 16:
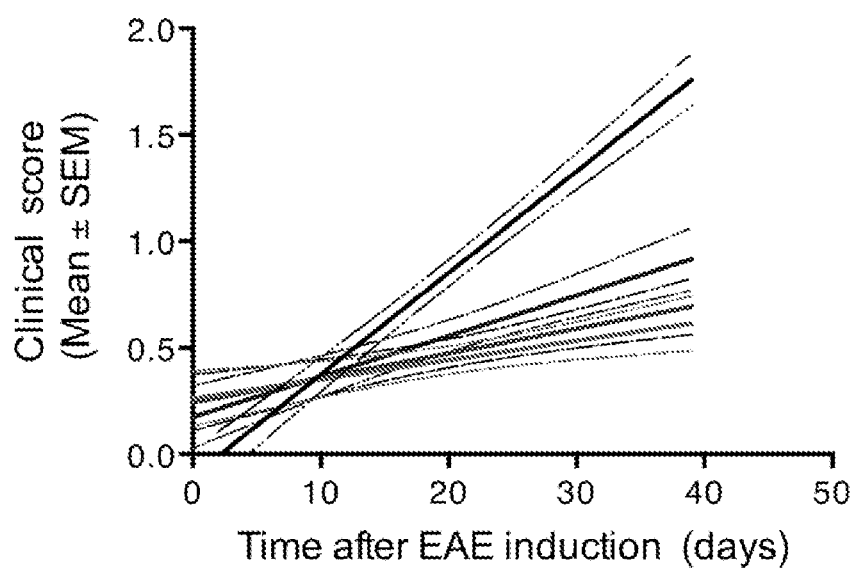

FIG. 16. Miglustat treatment halts chronic EAE progression. NOD Mice were immunized with MOG 35-55. Mice were treated daily with Miglustat or vehicle control at the beginning of the choric/progressive phase of NOD EAE and thereafter.

Figure 17:
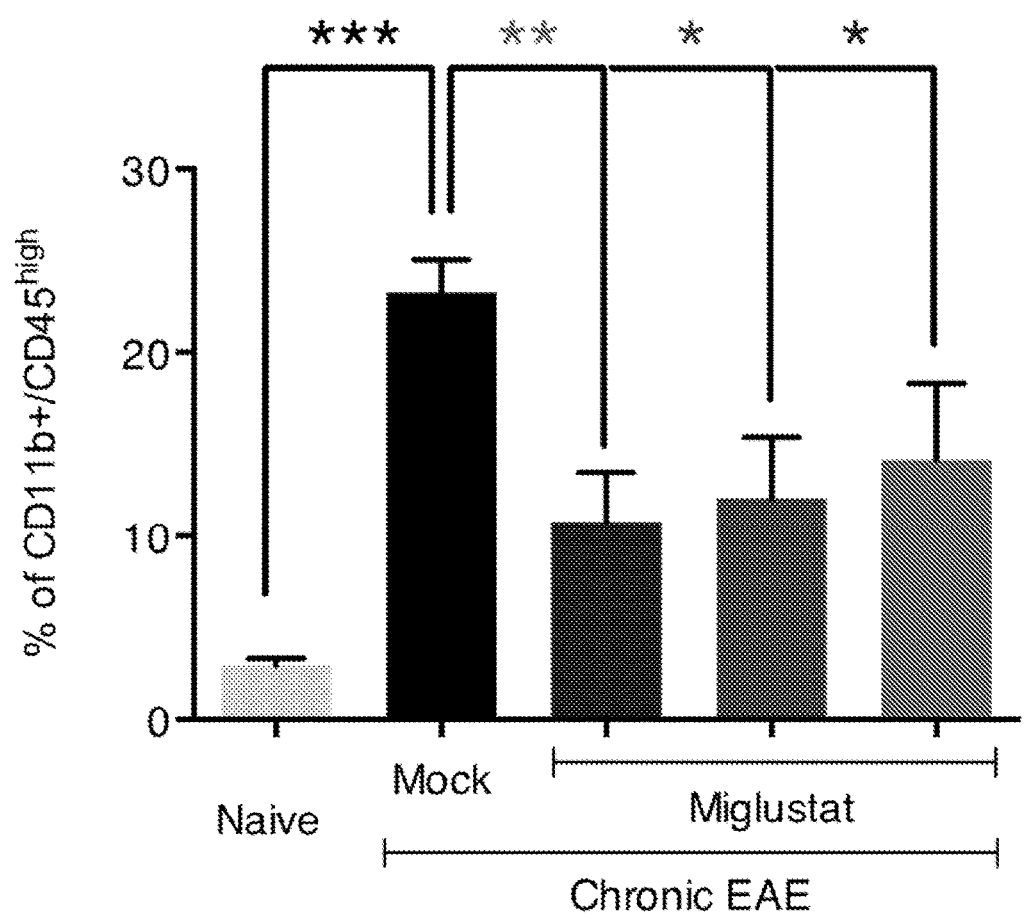

FIG. 17. Miglustat treatment reduces monocytes recruitment to the CNS

Figure 18:
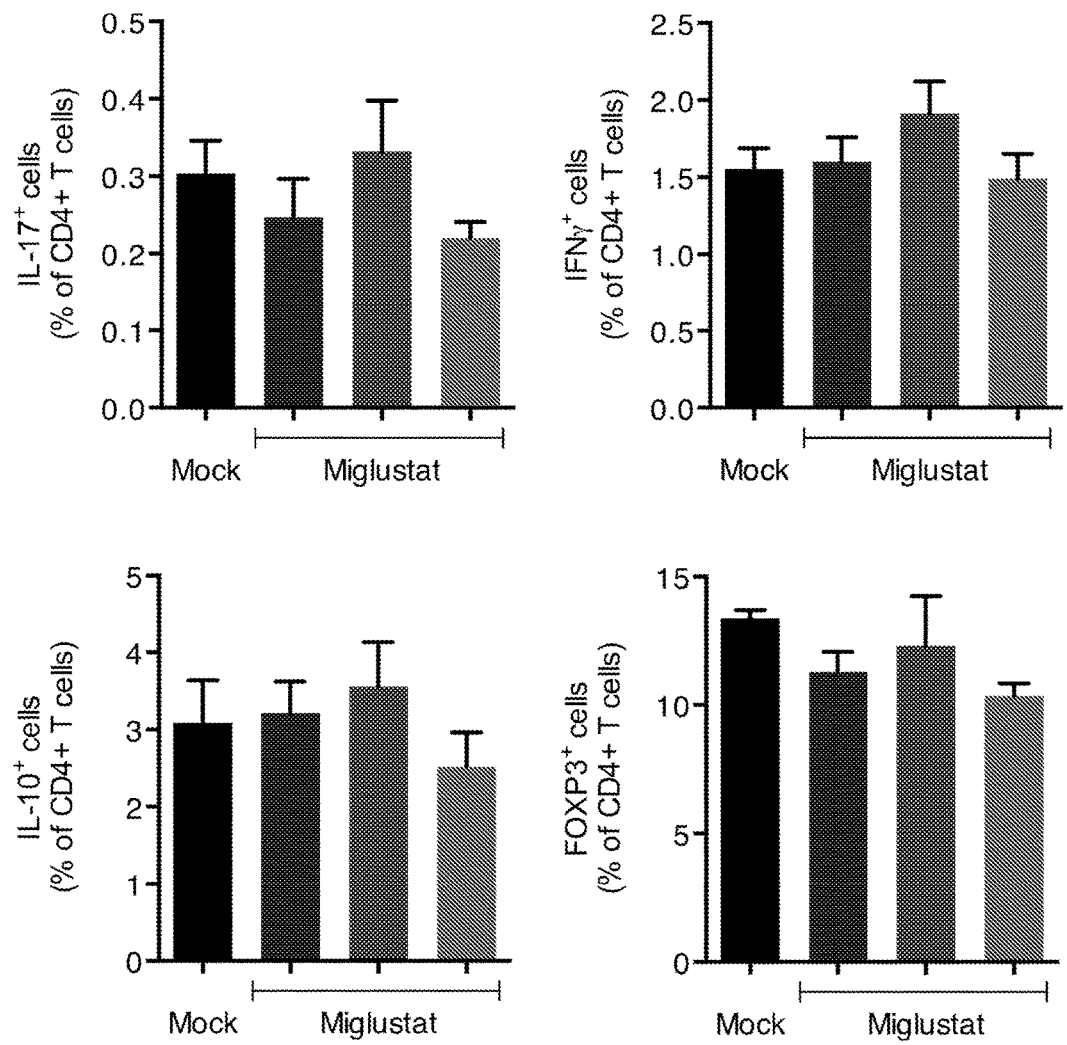

FIG. 18. Miglustat treatment does not affect T-cell polarization

Figure 19:
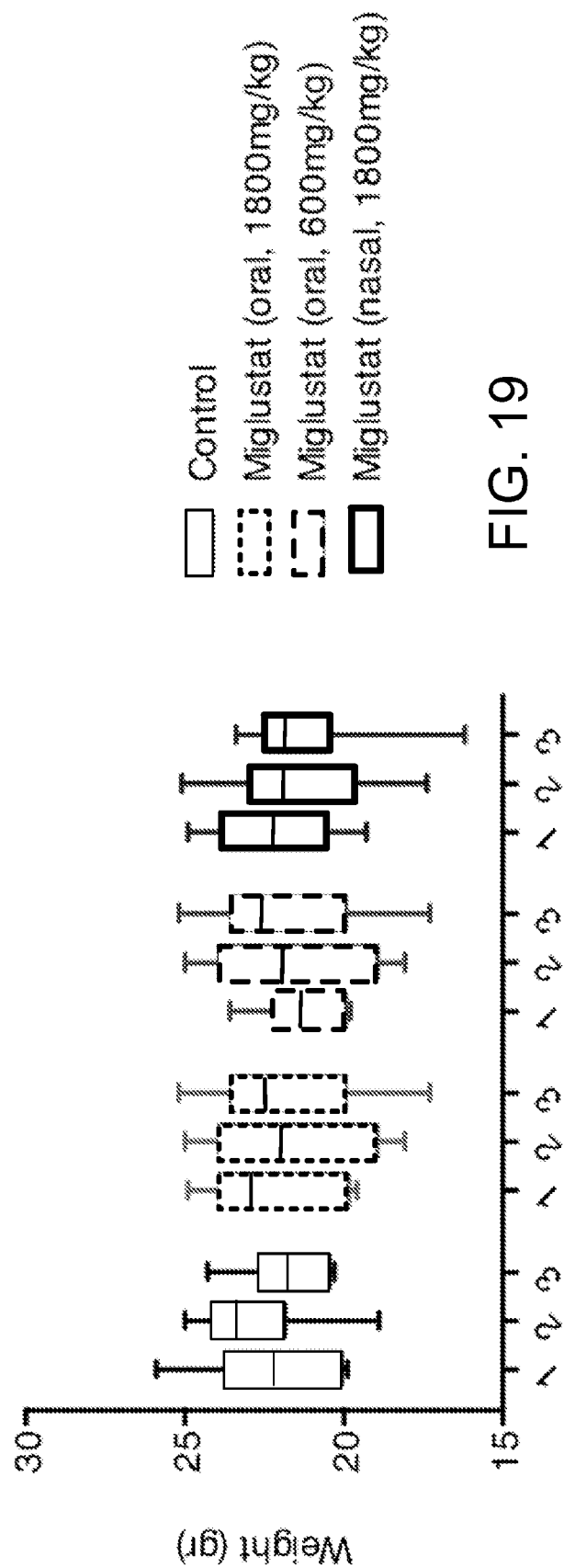

FIG. 19. Miglustat treatment does not affect body weight

DETAILED DESCRIPTION

Astrocytes play multiple functions in CNS development and function[1-4]. Both beneficial and detrimental roles have been assigned to astrocytes during CNS inflammation depending on factors such as the activation status, type and location of the astrocytes under investigation, the activating stimuli involved, and the duration of the immune response[3,32-36]. Indeed, astrocyte heterogeneity has only recently been recognized as a significant factor influencing the astrocyte response to activation[37,38]. GFAP$^{high}$ reactive astrocytes modulate leukocyte infiltration[7,8] and regulate the inflammatory response[5-9] in response to CNS trauma and acute EAE, but their regulation and function during chronic CNS inflammation is poorly understood.

As described herein, B4GALT6 up-regulation in astrocytes during the chronic phase of NOD EAE increases the CNS levels of the bioactive lipid LacCer, which acts in an autocrine manner to boost CNS inflammation and promote neurodegeneration. B4GALT5 and B4GALT6 are members of the β4-galactosyltransferase family that catalyze LacCer synthesis[17]. Although both enzymes are specifically up-regulated by astrocytes during chronic EAE and MS, B4GALT6, but not B4GALT5, is responsible for the increase in CNS LacCer levels and consequently astrocyte activation and disease progression. Previous studies described different biological roles for B4GALT5 and B4GALT6. For example, B4GALT5, but not B4GALT6, is essential for embryonic development[23,24]. Tokuda and coworkers have recently demonstrated that B4GALT6 deficiency results in a significant decrease in LacCer synthase activity in the CNS of naïve mice; LacCer synthesis in the kidney, however, is controlled by B4GALT5[24]. Taken together, these data suggest a spatial and functional compartmentalization of B4GALT5 and B4GALT6 LacCer synthase activities.

Microglia and Ly6C$^{high}$ CCR2$^+$ inflammatory monocytes are major components of the immune response in the CNS, with profound effects on neurodegeneration[9,14,19,21,31]. Astrocytes regulate leukocyte infiltration to the CNS through several mechanisms that range from the formation of a glial scar[39] to the secretion of chemokines, for example CCL-2 which recruits inflammatory monocytes to the CNS[20,21]. As demonstrated herein, the B4GALT6/LacCer axis controls the transactivation of the ccl2 promoter by NF-κB and IRF-1 and consequently, CCL-2 production by astrocytes. Accordingly, the inhibition of LacCer synthesis leads to both a decrease in CCL-2 production by astrocytes and a significant reduction in the recruitment of inflammatory monocytes to the CNS. B4GALT6 was also found to control the production of CCL-5 and CXCL-10; thus, these data identify the B4GALT6/LacCer pathway as an important regulator of inflammatory cell recruitment into the CNS.

CNS-infiltrating monocytes and microglia take different phenotypes that have been associated with pro- or anti-inflammatory activities; M1 pro-inflammatory microglia and monocytes are thought to contribute to the pathogenesis of MS and other CNS disorders[29,30,40]. Several factors influence microglia and monocyte activation[29,30,40]. GM-CSF, for example, promotes the polarization of M1 macrophages and activates microglia during EAE[41]. As shown herein, the B4GALT6/LacCer axis controls the production of GM-CSF by astrocytes and consequently controls microglial activation. Thus, the data suggest that in addition to Th17 cells[42,43], astrocytes also constitute a significant source of GM-CSF during chronic CNS inflammation. Collectively, the data demonstrate that LacCer produced by astrocytes controls the recruitment and the activation of inflammatory monocytes and microglia during chronic CNS inflammation.

Lipids exert significant effects on the immune response during microbial infections and autoimmunity, acting either as targets or regulators of the immune response[44-46]. Although lipid-specific antibodies and T cells have been identified in MS[47,48], the role of bioactive lipids in CNS autoimmunity is mostly unknown. Steinman and coworkers recently reported that myelin sheath lipids induce apoptosis in autoreactive T cells and ameliorate EAE[44]. Decreased levels of these lipids were detected in MS brain samples, suggesting that they play a role in the regulation of CNS-specific T cells. Considering the pro-inflammatory effects of LacCer shown herein, it appears that perturbations in the balance of anti- and pro-inflammatory lipids in the CNS play a significant role in MS pathology. Thus, profiling of CNS lipids can be used to identify subjects who have MS or other neurodegenerative diseases, and are candidates for therapeutic intervention as described herein.

Figures 1A, 1B:
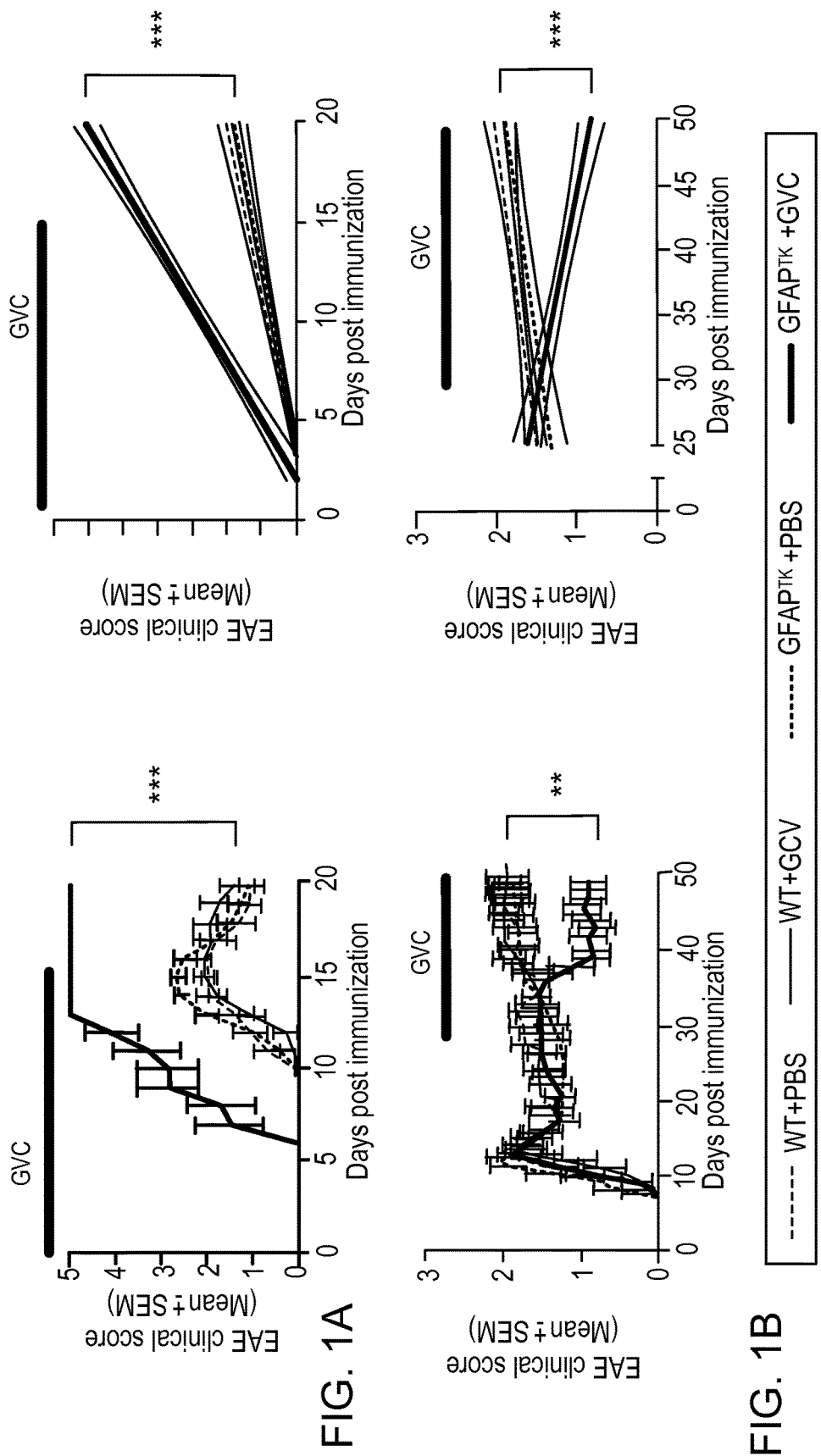

Importantly, as shown in FIGS. 1A-B, the depletion of reactive astrocytes during the acute phase resulted in a significant worsening of EAE (FIG. 1A), but astrocyte depletion during the progressive phase led to a significant amelioration of EAE (FIG. 1B). Moreover, although reactive astrocyte depletion in acute EAE results in increased monocyte and T-cell recruitment to the CNS, as shown herein, depletion during the progressive phase of EAE decreased leukocyte infiltration in the CNS (FIG. 9b) but did not affect the peripheral T-cell response (FIGS. 9c,d).

Taken together, these results demonstrate that LacCer produced by B4GALT6 controls a broad array of processes that drive CNS inflammation and neurodegeneration and are thought to play an important role in progressive MS. Thus, the modulation of LacCer synthesis is a therapeutic approach for progressive MS and also for other neurologic disorders in which astrocyte activation contributes to disease pathology.

Methods of Diagnosing and Predicting Development of Progressive MS

Included herein are methods for diagnosing neurodegenerative diseases, especially progressive multiple sclerosis (e.g., PPMS or SPMS), and for predicting the development of the same. The methods include obtaining a sample from a subject, and evaluating the presence and/or level of LacCer in the sample, and comparing the presence and/or level with one or more references, e.g., a control reference that represents a normal level of LacCer, e.g., a level in an unaffected subject, and/or a disease reference that represents a level of LacCer associated with progressive multiple sclerosis (e.g., PPMS or SPMS), e.g., a level in a subject having progressive multiple sclerosis (e.g., PPMS or SPMS). The presence of a level of LacCer above the reference level indicates that the subject indicates that the subject has with progressive multiple sclerosis (e.g., PPMS or SPMS).

In some embodiments, the level of LacCer is comparable to the level of LacCer in the disease reference, and the subject has one or more symptoms associated with progressive MS, e.g., PPMS or SMPS, then the subject has progressive MS, e.g., PPMS or SMPS. In some embodiments, the subject has no overt signs or symptoms of progressive MS, e.g., of PPMS or SMPS (e.g., has relapsing-remitting MS but has not shown signs of developing progressive MS, e.g., PPMS or SMPS), but the level of LacCer is comparable to the level of LacCer in the disease reference, then the subject is likely to develop or has an increased risk of developing progressive MS, e.g., PPMS or SMPS. In some embodiments, the sample includes a biological fluid, e.g., blood, plasma, serum, tears, saliva, semen, urine, and/or cerebrospinal fluid, or a biological tissue, e.g., a biopsy sample from a CNS lesion.

In some embodiments, once it has been determined that a person has progressive MS, e.g., PPMS or SMPS, or has an increased risk of developing progressive MS, e.g., PPMS or SMPS, then a treatment, e.g., as known in the art or as described herein, can be administered.

The presence and/or level of LacCer can be evaluated using methods known in the art, e.g., chromatography (e.g., liquid or thin layer chromatography) and/or mass spectrometry, e.g., using LC-MS/MS analysis, e.g., performed on a triple-quadrupole LC/MS/MS system, MRI-spectroscopy (see, e.g. Taki et al., J Biochem. 1992 May; 111(5):614-9), bioassays (e.g., by measuring proliferation of tumor cell lines that proliferate in the presence of LacCer; see, e.g., Jiang et al., Glycobiology 16:1045-1051 (2006); Hamamura et al., Proc. Natl. Acad. Sci. U.S.A 102 (31):11041-11046 (2005)); enzymatic assays for the detection of B4GALT6 activity; and immunoassays, e.g., quantitative immunoassay methods (such as ELISA or immunofluorescence) using an anti-LacCer antibody. Anti-LacCer antibodies are known in the art, e.g., mouse anti-lactosyl ceramide antibody (clone TrA7; IgM) (Symington et al., J Biol Chem 259:6008-6012 (1984) and Dohi et al., Cancer Res. 48:5680-5685 (1988)); other antibodies are commercially available, e.g., from Funakoshi Corp.

Suitable reference values can be determined using methods known in the art, e.g., using standard clinical trial methodology and statistical analysis. The reference values can have any relevant form. In some cases, the reference comprises a predetermined value for a meaningful level of LacCer, e.g., a control reference level that represents a normal level of LacCer, e.g., a level in an unaffected subject or a subject who has RRMS but is not presently at risk of developing progressive MS, e.g., PPMS or SMPS, and/or a disease reference that represents a level of LacCer associated with progressive MS, e.g., PPMS or SMPS, e.g., a level in a subject having progressive MS, e.g., PPMS or SMPS, or who later develops progressive MS, e.g., PPMS or SMPS (e.g., within a time period of 1, 3, 6, 9, 12 months, 2 years, 3 years, 4 years, or 5 years).

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have a disorder described herein (e.g., progressive MS, e.g., PPMS or SMPS) and does not develop progressive MS, e.g., PPMS or SMPS within 1, 3, 6, 9, 12 months, 2 years, 3 years, 4 years, or 5 years. In some cases it may be desirable that the control subject has RRMS, and in other cases it may be desirable that a control subject is a healthy control.

A disease reference subject is one who has (or has an increased risk of developing, e.g., of developing within a specific time period, e.g., 1, 3, 6, 9, 12 months, 2 years, 3 years, 4 years, or 5 years) progressive MS, e.g., PPMS or SMPS. An increased risk is defined as a risk above the risk of subjects in the general population.

Thus, in some cases the level of LacCer in a subject being greater than or equal to a reference level of LacCer is indicative of a clinical status (e.g., indicative of a disorder as described herein, e.g., SPMS). In other cases the level of LacCer in a subject being less than or equal to the reference level of LacCer is indicative of the absence of progressive MS, e.g., PPMS or SMPS, or normal risk of developing progressive MS, e.g., PPMS or SMPS, e.g., within 1, 3, 6, 9, 12 months, 2 years, 3 years, 4 years, or 5 years. In some embodiments, the amount by which the level in the subject is above the reference level is sufficient to distinguish a subject from a control subject, and optionally is a statistically significantly more than the level in a control subject. In cases where the level of LacCer in a subject being equal to the reference level of LacCer, the "being equal" refers to being approximately equal (e.g., not statistically different).

A predetermined reference value can depend upon the particular population of subjects (e.g., human subjects) selected. For example, an apparently healthy population, or a population of subjects with RRMS but not progressive MS, e.g., PPMS or SMPS (and who do not develop progressive MS, e.g., PPMS or SMPS, within a given time period, e.g., within 1, 3, 6, 9, 12 months, 2 years, 3 years, 4 years, or 5 years) will have a different 'normal' range of levels of LacCer than will a population of subjects which have, or are likely to develop (e.g., within a given time period, e.g., within 1, 3, 6, 9, 12 months, 2 years, 3 years, 4 years, or 5 years), a disorder described herein. Accordingly, the predetermined values selected may take into account the category (e.g., sex, age, health, risk, presence of RRMS or other diseases) in which a subject (e.g., human subject) falls. Appropriate ranges and categories can be selected with no more than routine experimentation by those of ordinary skill in the art.

In characterizing likelihood, or risk, numerous predetermined values can be established.

As an alternative to LacCer levels, levels of AHR, CCL2, CCL5, CCL7, CXCL10, CXCL3, CXCL9, Marco, NRF2, Timp1, TLR2, TLR8, TNFa, or VEGF mRNA or protein can be evaluated in a sample from a subject. Levels above a reference level indicate that the subject has or is at risk of developing progressive MS, e.g., PPMS or SPMS. A number of methods are known in the art for determining mRNA or protein levels. The presence and/or level of a protein can be evaluated using methods known in the art, e.g., using quantitative immunoassay methods. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289 (5485):1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect the presence and/or level of a protein or mRNA.

Methods of Treatment

The methods described herein include methods for the treatment of a neurological disorder, i.e., a neurological disorder associated with dysfunction of astrocytes, using as an active agent an inhibitor of LacCer synthesis, e.g., an inhibitor of B4GALT6 and/or glucosylceramide (GlcCer) synthase. As shown in FIGS. 1A-B, the depletion of reactive astrocytes during the acute phase resulted in a significant worsening of EAE (FIG. 1A), but astrocyte depletion during the progressive phase led to a significant amelioration of EAE (FIG. 1B). Thus in some embodiments, the disorder is progressive MS, e.g., SPMS or PPMS, and is not RRMS. Alternatively, the disease may be another neurodegenerative disease, e.g., Parkinson's Disease, Alzheimer's Disease, Amyotrophic Lateral Sclerosis, Alexander disease, Huntington Disease, or Rett's disease (See, e.g., Maragakis and Rothstein, Nature Clinical Practice Neurology (2006) 2, 679-689); or brain and spinal cord trauma. Dysfunction of astrocytes is described, e.g. in Maragakis and Rothstein, Nature Clinical Practice Neurology (2006) 2, 679-689.

In some embodiments, once it has been determined that a person has progressive MS, e.g., PPMS or SMPS, or has an increased risk of developing progressive MS, e.g., PPMS or SMPS, or has elevated levels of LacCer synthesis, then a treatment comprising administration of a therapeutically effective amount of an inhibitor of LacCer synthesis can be administered. These methods can thus include obtaining a sample from a subject, and evaluating the presence and/or level of LacCer in the sample, and comparing the presence and/or level with one or more references, e.g., a control reference that represents a normal level of LacCer, e.g., a level in an unaffected subject, and/or a disease reference that represents a level of LacCer associated with progressive multiple sclerosis (e.g., PPMS or SPMS), e.g., a level in a subject having progressive multiple sclerosis (e.g., PPMS or SPMS). The presence of a level of LacCer above the reference level indicates that the subject indicates that the subject has with progressive multiple sclerosis (e.g., PPMS or SPMS), and should be treated with an inhibitor of LacCer synthesis. These methods can also be used to predict whether someone will benefit from treatment with an inhibitor of GlcCer synthase; a subject who has a level of LacCer above a reference level is more likely to benefit from treatment with an inhibitor of LacCer synthesis than is a subject who has a level of LacCer below the reference level. In addition, the methods can be used for selecting a treatment for a subject; a treatment with an inhibitor of LacCer synthesis is selected for a subject who has a level of LacCer above a reference level. In some embodiments, the subject has one or more symptoms associated with progressive MS, e.g., PPMS or SMPS, and/or the subject has been diagnosed with MS, e.g., progressive MS, e.g., PPMS or SMPS, or previously diagnosed with RRMS but is suspected of having transitioned to progressive MS.

Generally, the methods include administering a therapeutically effective amount of an inhibitor of GlcCer synthase as described herein, to a subject who is in need of, or who has been determined to be in need of, such treatment. As used in this context, to "treat" means to ameliorate at least one symptom of the disorder associated with activation of astrocytes. A treatment can result in a reduction in one or more symptoms of MS, e.g., depression and fatigue, bladder dysfunction, spasticity, pain, ataxia, and intention tremor. A therapeutically effective amount can be an amount sufficient to prevent the onset of an acute episode or to shorten the duration of an acute episode, or to decrease the severity of one or more symptoms, e.g., heat sensitivity, internuclears ophthalmoplegia, optic neuritis, and Lhermitte symptom. In some embodiments, a therapeutically effective amount is an amount sufficient to prevent the appearance of, delay or prevent the growth (i.e., increase in size) of, or promote the healing of a demyelinated lesion in one or more of the brain, optic nerves, and spinal cord of the subject, e.g., as demonstrated on MRI.

In some embodiments, e.g., wherein an inhibitor of GlcCer synthase is administered, the disorder is MS, e.g., progressive MS, e.g., PPMS or SMPS; in some embodiments, the disorder is not Alzheimer's disease (AD), Niemann-Pick Disease Parkinson's disease, Landry-Guillain-Barre-Strohl syndrome, RRMS, viral encephalitis, acquired immunodeficiency disease (AIDS)-related dementia, amyotrophic lateral sclerosis, brain trauma, or a spinal cord disorder. In some embodiments, e.g., wherein an inhibitor of GlcCer synthase is administered, the methods do not include administering a glutathione donor such as S-nitroglutathione (GSNO), L-2-oxo-thiazolidine 4-carboxylate (Procysteine), N-acetyl cysteine (NAC), or N-acetyl glutathione as an active agent.

Relapsing-Remitting and Progressive MS

Multiple Sclerosis (MS) is an inflammatory demyelinating disease of the central nervous system (CNS). MS is typically characterized clinically by recurrent or chronically progressive neurologic dysfunction, caused by lesions in the CNS. Pathologically, the lesions include multiple areas of demyelination affecting the brain, optic nerves, and spinal cord. The underlying etiology is uncertain, but MS is widely believed to be at least partly an autoimmune or immune-mediated disease.

In 85% of the patients MS initially follows a relapsing-remitting course (RRMS) in which acute autoimmune attacks against the central nervous system (CNS) are followed by a complete recovery (Compston and Coles, Lancet 372, 1502-1517 (2008)). The majority of the RRMS patients go on to develop secondary progressive MS (SPMS), characterized by a progressive, irreversible accumulation of neurological disability (Rovaris et al., Lancet Neurol 5, 343-354 (2006)). The progressive and irreversible disability that characterizes SPMS occurs in the absence of new inflammatory lesions, suggesting that other mechanisms might play a role in this stage of MS (Rovaris et al., Lancet Neurol 5, 343-354 (2006)). Although several therapies show positive effects on RRMS, they are usually ineffective in SPMS, and no markers are available to monitor the transition to SPMS. Indeed, treatments that halt the adaptive inflammatory response show positive effects on the management of RRMS but are usually ineffective in SPMS (Lopez-Diego and Weiner, Nat Rev Drug Discov 7, 909-925 (2008)). Thus, it is important to characterize the processes involved in the transition to SPMS, to identify new therapies for progressive MS and biomarkers to monitor the RRMS to SPMS transition.

Secondary Progressive Multiple Sclerosis (SPMS), one of four internationally recognized forms of Multiple Sclerosis (the others being Relapsing/Remitting Multiple Sclerosis, Primary Progressive Multiple Sclerosis and Progressive Relapsing Multiple Sclerosis), is characterized by a steady progression of clinical neurological damage with or without superimposed relapses and minor remissions and plateaus. People who develop SPMS will generally have previously suffered a period of Relapsing/Remitting Multiple Sclerosis (RRMS), which may have lasted from two to forty years or more. Occasionally the subject will have some relapses and remissions after the development of SPMS, but these tend to become less frequent over time.

Primary progressive MS (PPMS) is relatively rare (about 15% of the MS patient population), and features a slowly progressive loss in ability from onset of the disease. Most PPMS patients have progressive myelopathy or progressive cerebellar dysfunction.

A diagnosis of MS, and a determination of subtype, can be made using methods known in the art, e.g., on the basis of the presence of CNS lesions disseminated in space and time, and the elimination of alternative diagnoses (Problems of experimental trials of therapy in multiple sclerosis: Report by the panel on the evaluation of experimental trials of therapy in multiple sclerosis Ann N Y Acad Sci. 122: 1965; 552-568). Alternatively, a diagnosis can be made based on the presence of clinical signs and symptoms including heat sensitivity, internuclear ophthalmoplegia, optic neuritis, and Lhermitte symptom (see, e.g., McDonald et al., Recommended Diagnostic Criteria for Multiple Sclerosis: Guidelines From the International Panel on the Diagnosis of Multiple Sclerosis. Ann. Neurol. 2001; 50:121; and Polman et al., Diagnostic Criteria for Multiple Sclerosis: 2005 Revisions to the "McDonald Criteria." Ann Neurol 2005; 58:840-846).

Methods of quantifying disability in MS include the Kurtzke Expanded Disability Status Scale (EDSS); MRI scanning; The Scripps Neurologic Rating Scale (SNRS); The Krupp Fatigue Severity Scale (FSS); The Incapacity Status Scale (ISS); The Functional Independence Measure (FIM); The Ambulation Index (AI); The Cambridge Multiple Sclerosis Basic Score (CAMBS); The Functional Assessment of Multiple Sclerosis (FAMS); Profile of Mood States (POMS); and the Sickness Impact Profile (SIP).

Further information about diagnosing and treating MS, and progressive MS, e.g., PPMS or SMPS, be found in the art, e.g., in Hurwitz et al, Ann Indian Acad Neurol. 2009 October-December; 12(4): 226-230; and Spinal Cord Medicine, Principles and Practice, Lin et al., Eds., (Demos Medical Publishing, Inc., 2003), e.g., Section V, Chapter 32, "Multiple Sclerosis".

Targeting LacCer Synthesis: B4GALT6 and GlcCer Synthesis

The methods described herein include methods for the treatment of progressive multiple sclerosis (e.g., PPMS or SPMS) using inhibitors of LacCer synthesis, e.g., inhibitors of B4GALT6 and/or glucosylceramide (GlcCer) synthase, or activators of glucocerebrosidase. The methods include identifying a subject having progressive multiple sclerosis (e.g., PPMS or SPMS), and administering a therapeutically effective amount of a specific inhibitor of LacCer synthesis, e.g., a therapeutic composition comprising a specific inhibitor of B4GALT6 and/or GlcCer synthesis, to a subject who has progressive multiple sclerosis (e.g., PPMS or SPMS).

Small Molecule Inhibitors of GlcCer Synthase

Inhibitors of GlcCer synthase include small molecules, most of which are enzyme substrate analogs that bind to the enzyme active site and prevent substrate binding. These inhibitors include ceramide analogs (see, e.g., U.S. Pat. Nos. 6,569,889; 6,255,336; 5,916,911; 5,302,609; Lee et al., J. Biol. Chem. 274(21):14662 (1999); Abe et al., J. Biochem. 111:191 (1992); Inokuchi et al., J. Lipid Res. 28:565 (1987); Shayman et al., J. Biol. Chem. 266:22968 (1991); and Bell et al. Ed., 1993, Advances in Lipid Research: Sphingolipids in Signaling (Academic Press, San Diego)) and sugar analogs (see, e.g., U.S. Pat. Nos. 6,660,749; 6,610,703; 5,472,969; 5,525,616; Overkleef et al., J. Biol. Chem. 273(41):26522 (1998)); see also US20120022126, US20130040953, US20130225573, US20070135487, U.S. Pat. Nos. 5,700,826 and 5,840,721; and Koltun et al., Bioorg Med Chem Lett. 2011 Nov. 15; 21(22):6773-7. Examples include 1-(3',4'-ethylenedioxy)phenyl-2-nonanoylamino-3-pyrrolidino-1-propanol; 1-(3',4'-ethylenedioxy)phenyl-2-octanoylamino-3-pyrrolidino-1-propanol; D-threo-(1R,2R)-phenyl-2-decanoylamino-3-morpholino-1-propanol (PDMP) and analogs thereof including D-PDMP, see, e.g., Hillaert et al., Bioorg Med Chem. 2006 Aug. 1; 14(15):5273-84; D-threo-EtDO-P4; ((1R,2R)-nonanoic acid[2-(2',3'-dihydro-benzo[1,4] dioxin-6'-yl)-2-hydroxy-1-pyrrolidin-1-ylmethyl-ethyl]-amide-L-tartaric acid salt; AMP-DNM; CCG0203586 (1-hydroxy-3-(pyrrolidin-1-yl)acetamide); Genz-112638 (eliglustat); Genz-529468; GZ-161; Genz-682452; EXEL-0346 (Richards et al., J Med Chem. 2012 May 10; 55(9): 4322-35); OGT2378; Genz-123346; deoxynojiromycin-based GCS inhibitors (e.g., N-butyl-deoxynojirimycin (NB-DNJ also known as miglustat), N-(5'-adamantane-1'-ylmethoxy)-pentyl-1-deoxynojirimycin (AMP-DNM), or al-deoxynojirimycin with a long alkyl side chain, e.g., long-chain N-alkyl derivative of 1,5-dideoxy-1,5-imino-D-glucitol having from nine to about 20 carbon atoms in the alkyl chain. The N-alkyl substituent thus can be, e.g, nonyl, decyl, undecyl, dodecyl, tetradecyl, hexadecyl, cis-11-hexadecenyl, octadecyl, cis-13-octadecenyl, and eicosyl. See U.S. Pat. No. 6,610,703)); and PPMP (DL-threo-1-Phenyl-2-palmitoylamino-3-morpholino-1-propanol) see US20130217691 and US 20050101674.

Additional inhibitors useful in the present methods include those described in U.S. Pat. No. 8,389,517; 20110166134; 20070203223; 20050222244; 20130095089; U.S. Pat. Nos. 7,335,681; 7,253,185; 7,148,251; 6,916,802; 6,890,949; 6,051,598; 6,040,332; 6,030,995; 5,952,370; 5,945,442; 20090247559; 20060111400; 20060058349; 20060074107; U.S. Pat. No. 8,557,844; 20100204162; U.S. Pat. No. 8,252,789; 20130012539; and 20090163500.

Inhibitory Nucleic Acids Targeting B4GALT6

Specific inhibitors of B4GALT6 include inhibitory nucleic acids that target the B4GALT6 gene or mRNA; the sequence of the human B4GALT6 mRNA is in GenBank at Acc. No. NM_004775.3; the genomic sequence is at NC_000018.10. Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), and other oligomeric compounds or oligonucleotide mimetics which hybridize to at least a portion of the target B4GALT6 nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. The inhibitory nucleic acids can be modified, e.g., to include a modified nucleotide (e.g., locked nucleic acid) or backbone (e.g., backbones that do not include a phosphorus atom therein), or can by mixmers or gapmers; see, e.g., WO2013/006619. A number of siRNAs directed against B4GALT6 are commercially available, e.g., from origene, labome, abnova, and qiagen.

The inhibitory nucleic acids used to practice the methods described herein, whether RNA, cDNA, genomic DNA, vectors, viruses or hybrids thereof, can be isolated from a variety of sources, genetically engineered, amplified, and/or expressed or generated recombinantly or synthetically. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. "Molecular Cloning: A Laboratory Manual." (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Inhibitory nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Inhibitory nucleic acids for use in the methods described herein can include one or more modifications, e.g., be stabilized against nucleolytic degradation such as by the incorporation of a modification, e.g., a nucleotide modification. For example, inhibitory nucleic acids can include a phosphorothioate at least the first, second, or third internucleotide linkage at the 5' or 3' end of the nucleotide sequence. As another example, inhibitory nucleic acids can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the inhibitory nucleic acids can include at least one 2'-O-methyl-modified nucleotide, and in some embodiments, all of the nucleotides include a 2'-O-methyl modification. In some embodiments, the inhibitory nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of inhibitory nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Antibodies that Bind to and Inhibit B4GALT6

Antibodies that bind to and inhibit the activity of B4GALT6 (i.e., to inhibit LacCer synthesis) can also be used; the sequence of human B4GALT6 protein is in GenBank at Acc. No. NP_004766.2. The term "antibody" as used herein refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, Antibodies: A Laboratory Manual (1988); Goding, Monoclonal Antibodies: Principles and Practice, (N.Y. Academic Press 1983); Howard and Kaser, Making and Using Antibodies: A Practical Handbook (CRC Press; 1st edition, Dec. 13, 2006); Kontermann and Dübel, Antibody Engineering Volume 1 (Springer Protocols) (Springer; 2nd ed., May 21, 2010); Lo, Antibody Engineering: Methods and Protocols (Methods in Molecular Biology) (Humana Press; Nov. 10, 2010); and Dübel, Handbook of Therapeutic Antibodies: Technologies, Emerging Developments and Approved Therapeutics, (Wiley-VCH; 1 edition Sep. 7, 2010). Antibodies that bind to B4GALT6 are available commercially from EMD Millipore, R&D Systems, Cell Signaling Technology, OriGene, Novus Biologicals, Thermo Fisher Scientific, LSBio, Abcam, and/or Cloud-Clone Corp.), and one of skill in the art would readily be able to make or obtain an antibody and test the ability of the antibody to inhibit LacCer synthesis in a cell expressing B4GALT6.

Activators of Glucocerebrosidase

Activators of glucocerebrosidase can also be used, in addition to or as an alternative to the other compounds described herein. Activators are known in the art, including NCGC00182186 (5-cyclopropylidene-7-(difluoromethyl)-N-(2-phenylsulfanylphenyl)-1H-pyrazolo[1,5-a]pyrimidine-3-carboxamide) and NCGC00182510 ([2-(tert-butylamino)-2-oxoethyl] 2-[2-(4-bromoanilino)-2-oxoethoxy]benzoate) (see, e.g., Goldin et al., PLoS ONE 7(1):e29861); or Saposin C or phosphatidylserine (see, e.g., Salvioli et al., Biochem. J. (2005) 390 (95-103)). Saposin C is a sphingolipid activator protein of 8.5 kDa that activates lysosomal glucocerebrosidase. Two functional domains, each comprising a binding site adjacent to or partially overlapping with an activation site, have been identified. Domain 1 is located within amino acid positions 6-34, and domain 2 is amino acids 41-60. The activation sites span residues 27-34 and 41-49, and binding sites comprise residues 6-27 and 45-60. Peptides containing the sequences of either domain 1 or displayed 90% of the activity of the full-length synthetic saposin C. (See Yoneshige et al., J Neurosci Res. 2010 Aug. 1; 88(10):2118-34; Weiler et al., Protein Sci. 1995 April; 4(4):756-64; Weiler et al., J Mol Neurosci. 1993 Fall; 4(3):161-72; Fujibayashi and Wenger, Clin Chim Acta. 1985 Mar. 15; 146(2-3):147-56; Zschoche et al., Eur J Biochem. 1994 May 15; 222(1):83-90). Thus, Saposin C or active fragments thereof (e.g., comprising Domains 1 or 2) can be used. The sequence of human Saposin C is as follows (domains 1 and 2 are bold and double-underlined):

SDVYCEVCEFLVKEVTKLIDNNKTEKEILDAFDK-MCSKLPKSLSEECQEVVDTYGSSILSILLEEV-SP'ELVCSMLHLCSG (SEQ ID NO:1)

Identifying Subjects with Progressive Multiple Sclerosis (e.g., PPMS or SPMS)

In some embodiments, the methods can include screening for subjects for SPMS, e.g., by screening for one or more indicators of progressive multiple sclerosis (e.g., PPMS or SPMS). Methods for identifying subjects with progressive multiple sclerosis (e.g., PPMS or SPMS) are known in the art, and can also include identifying subjects by detecting elevated levels of LacCer as described herein. In some embodiments, SPMS is identified by progression of disability in a subject with MS to an EDSS of 3.5 or greater, usually in motor/cerebellar functions. SPMS can also be diagnosed in the presence of deterioration in symptoms independent of relapses for ≥6 months following an initial relapsing-remitting course. PPMS can be diagnosed, e.g., based on the progression of disability from the onset of disease (e.g., without periods of improvement), e.g., a minimum of one year of disease progression with at least two of a positive brain MRI, a positive spinal cord MRI, and positive CSF findings.

The methods can include detecting the presence of progressive multiple sclerosis (e.g., PPMS or SPMS) in a subject, or a likelihood of development of progressive multiple sclerosis (e.g., PPMS or SPMS) in a subject (e.g., within a specific time period, e.g., 1, 3, 6, 9, 12 months, 2 years, 3 years, 4 years, or 5 years, e.g., using a method described herein), and selecting the subject on the basis that they have or are likely to develop progressive multiple sclerosis (e.g., PPMS or SPMS).

In general, the methods described herein can be practiced on any mammal, preferably a human.

Standard Treatments

In some embodiments, a treatment described herein is administered in combination with a standard treatment for MS, e.g., administration of corticosteroid therapy, interferon beta-1b, Glatiramer acetate, mitoxantrone, Fingolimod, teriflunomide, dimethyl fumarate, natalizumab, cannabis, or a combination thereof. In some embodiments, the treatment described herein is administered in combination with a treatment for one or more symptoms of MS, e.g., depression and fatigue, bladder dysfunction, spasticity, pain, ataxia, and intention tremor; such treatments include pharmacological agents, exercise, and appropriate orthotics. Additional information on the diagnosis and treatment of MS can be found at the National MS Society website, on the world wide web at nationalmssociety.org.

In some embodiments, where a subject is identified as having or likely to develop SPMS within a specific time period, e.g., as having a level of GlcCer above a reference level a treatment for progressive MS is administered, e.g., comprising mitoxantrone or natalizumab.

Pharmaceutical Compositions

The methods described herein include the manufacture and use of pharmaceutical compositions, which include inhibitors of LacCer synthesis as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with the intended route of administration. Examples of routes of administration that are especially useful in the present methods include parenteral (e.g., intravenous), intrathecal, oral, and nasal or intranasal (e.g., by administration as drops or inhalation) administration. For compounds that don't cross the blood brain barrier, delivery directly into the CNS or CSF can be used, e.g., using implanted intrathecal pumps (see, e, g., Borrini et al., Archives of Physical Medicine and Rehabilitation 2014; 95:1032-8; Penn et al., N. Eng. J. Med. 320:1517-21 (1989); and Rezai et al., Pain Physician 2013; 16:415-417) or nanoparticles, e.g., gold nanoparticles (e.g., glucose-coated gold nanoparticles, see, e.g., Gromnicova et al. (2013) PLoS ONE 8(12): e81043). Methods of formulating and delivering suitable pharmaceutical compositions are known in the art, see, e.g., the books in the series *Drugs and the Pharmaceutical Sciences: a Series of Textbooks and Monographs* (Dekker, N.Y.); and Allen et al., *Ansel's Pharmaceutical Dosage Forms and Drug Delivery Systems*, Lippincott Williams & Wilkins; 8th edition (2004).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

For oral administration, the compositions can be formulated with an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998).

Liposomes (e.g., as described in U.S. Pat. No. 6,472,375) and microencapsulation can also be used to deliver a compound described herein. Biodegradable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser, e.g., single-dose dispenser together with instructions for administration. The container, pack, or dispenser can also be included as part of a kit that can include, for example, sufficient single-dose dispensers for one day, one week, or one month of treatment.

Dosage

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

EXAMPLES

The invention is further described in the following examples, which do not limit the scope of the invention described in the claims.

Materials and Methods

The following Materials and Methods were used in the Examples set forth below.

Animals.

C57BL/6J, NOD/ShiLtJ (NOD), IRF-1 deficient mice and GFAP-HSV-TK mice, were from The Jackson Laboratory. Heterozygote GFAP-HSV-TK bearing C57B1/6 mice were used to generate F1 littermates that were either GFAP$^{TK}$ or WT F1. Tg(GFP-hGFAP) FVB transgenic mice have been described[49]. All animals were kept in a pathogen-free facility at the Harvard Institutes of Medicine. All experiments were carried out in accordance with guidelines prescribed by the Institutional Animal Care and Use Committee of Harvard Medical School.

EAE Induction and Treatments.

EAE was induced by immunization female mice with MOG$_{35-55}$ peptide emulsified in CFA (Difco Laboratories) at a dose of 100 µg (C57BL/6 and F1 mice) or 150 µg (NOD mice) per mouse, followed by the administration of pertussis toxin (150 ng per mouse; List biological laboratories, Inc.) on days 0 and 2 as described[14]. Clinical signs of EAE were assessed according to the following score: 0, no signs of disease; 1, loss of tone in the tail; 2, hind limb paresis; 3, hind limb paralysis; 4, tetraplegia; 5, moribund. GCV (APP Pharmaceuticals), or vehicle control (PBS) was administered daily (25 mg/kg, subcutaneously) 7 days before EAE induction and continued for the duration of the acute phase (day 15), or only during the progressive/chronic phase (day 30-50). LacCer (Matreya LLC) or vehicle (10% DMSO), were administered at a dose of 10 µg per mouse together with the MOG$_{35-55}$ peptide to C57BL/6J mice during EAE induction, and also intraperitoneally (i.p.) every other 3 days thereafter. LacCer or vehicle administration to NOD mice were initiated 35 days after disease induction at a dose of 10 µg per mouse given i.p. every 3 other days. PDMP (Matreya LLC) or vehicle control (5% tween-80), were administered at day 40 after EAE induction twice a day with 20 mg/kg given i.p. for the duration of the experiment.

Immunofluorescence (IF).

Animals were perfused with 4% paraformaldehyde in 0.1 M PBS. Tissues were cryoprotected in 0.1 M PBS plus 30% sucrose, and cut with cryostat into 10-µm-thick sections. Sections were blocked in 5% goat serum, M.O.M.™ Mouse Ig Blocking reagent (Vector laboratories) containing 0.3% Triton™ X-100 (Sigma-Aldrich), and incubated overnight at 4° C. with following antibodies: GFAP (chicken, 1:500, Abcam), GFP (chicken, 1:500, Abcam), IBA-1 (Rabbit, 1:200, Dako), B4GALT6 (Rabbit, 1:100, proteintech), iNOS [mouse (4E5), 1:100, iNOS], CCL2 [mouse (2D8), 1:100, Fisher scientific], Nestin [mouse (rat-401), Millipore], CD31 [mouse (RM0032-1D12), 1:100, Abcam], and IRF-1 (rabbit, 1:250, Santa cruz). The next day sections were washed 3 times, and incubated with an appropriate fluorophore-conjugated goat secondary Abs (1:1000; Abcam) for 1 h at room temperature. Six animals/group were used. Images were taken using a LSM 710 confocal microscope (Carl Zeiss).

Isolation of Cells from Adult Mice CNS.

Mononuclear cells were isolated from the CNS as previously described[50] with minor modifications. Naïve and EAE mice were euthanatized, and then subjected to perfusion through the left ventricle with ice-cold sterile PBS. Brains and spinal cord were then removed, minced and enzymatically dissociated with 0.05% (w/v) collagenase type III (Worthington Biochemical), 0.5% Dispase II (Roche Applied Science), 40 µg/ml DNAse I, 20 mM HEPES in HBSS) for 30 min at 37 C to make a suspension of single cells. Enzymes were inactivated with 20 ml of $Ca^{2+}/Mg^{2+}$-free HBSS containing 2 mM EDTA and 20 mM HEPES. The digested tissue was triturated and passed through a 100-04 cell strainer. Cells were centrifuged and resuspended in 30% isotonic Percoll (GE Healthcare) and 40 µg/ml DNAse I, underlined by 70% isotonic Percoll, and centrifuged at 1000×g at 4° C. for 25 min. Cells were collected from the 70%-30% interphase, and sorted by FACS Aria.

FACS Sorting of Astrocytes, Microglia and Monocytes.

These purification procedures are based on previously described dissociation and purification protocols[50,51]. Isolated CNS cells, were incubated with anti-Mouse CD16/CD32 for 15 min on ice to block the Fc receptors, and stained with fluorochrome-conjugated antibody for CD11b (M1/70), CD45(90), CD3 (145-2C11), CD4 (GK1.5), and Ly6C (HK1.4), and Biotion-conjugated GSL I—isolectin B4 (Vector labs), CD105 (N418), CD140a (APA5), CD11c (N418), F4/80 (BM8), O4 (O4, Miltenyi Biotec), and CD19 (eBio1D3), and un-conjugated antibodies recognizing mouse MOG (8-18C5, Millipore), O1 (O1), and Galactocerebroside (mGlaC, Millipore). All antibodies were from Ebioscience, unless otherwise mentioned (clone number, when relevant, in parentheses). Cells were washed and incubated PE-conjugated Streptavidin and R-Phycoerythrin AffiniPure F(ab')2 fragment of Goat Anti-Mouse IgG+IgM (H+L) (Jackson ImmunoResearch laboratories) for 20 min at 4 C in the dark. Cells were washed, incubated with 7-AAD or Fixable Viability Dye eFluor® 450 (if cells were to be used for intracellular staining), for exclusion of dead cells (FIG. S3A), and sorted as following. Microglia were sorted as CD11b[+] cells with low CD45 expression and low Ly6C (CD11b+/CD45$^{low}$/Ly6C$^{low}$), while the inflammatory monocytes were considered as CD11b+/Ly6C$^{high}$ [52]. T-cells were sorted as CD3[+]CD4[+] cells. Astrocytes were isolated following the depletion of lymphocytes, microglia, monocytes (FIG. S3B), and oligodendrocytes, and lymphocytes (T-cells, B-cells, and NK cells) (FIG. S3C). Sorted cells were found to be >85% GFAP[+] by FACS analysis (FIG. S3D). We confirmed that we had isolated a relatively pure populations of astrocytes by qPCR for the astrocyte markers[44,51] gfap, aldh1l1 and aqp4, and found them to be exclusively expressed in the astrocyte fraction (in a similar expression pattern to that of GFP[+] astrocytes sorted from Tg(GFP-hGFAP) FVB transgenic mice[49]) (FIG. S3E). We used an additional cohort of markers to explore for presence of immune cells [microglia/monocytes cells—itgam (CD11b), and emr1 (F4/80), dendritic cells—itgax (CD11c), NK cells—Klrb1c (Nk1.1), T-cells—cd3, and B-cells—cd19], oligodendrocytes (mog, mbp), and neurons (syt1, snap25) (FIG. S3F, G).

LacCer Measurement.

Chemical standards of LacCer (d18:1/16:0) and LacCer (d18:1/18:0) were obtained from Avanti Polar Lipids. Quantification of LacCer (d18:1/16:0) and LacCer (d18:1/18:0) was achieved by LC-MS/MS analysis performed on an Agilent (Agilent Technologies, Santa Clara, Calif.) 6460 triple-quadrupole LC/MS/MS system. The fragments from the [M+H]$^+$ ions for LacCer and internal standard were subjected to collision induced dissociation and the two major types of fragment ions were monitored via electrospray ionization in the positive ion mode in multiple reaction monitoring (MRM) mode for each ion. These two MRM transitions corresponded to the loss of the neutral lactosyl moiety, and to the formation of the lactose ion. Specifically, the MRM transitions used for quantification for LacCer (d18:1/16:0) and LacCer(d18:1/18:0) were 862.5>464.5 and 890.6>548.5, respectively. Secondary confirmatory MRM transitions for LacCer(d18:1/16:0) and LacCer(d18:1/18:0) of 862.5>264.3 and 890.6>264.3 were also monitored. Mass spectrometer parameter settings were gas temp (325° C.), gas flow (12 L/min), nebulizer (25 psi), sheath gas temp (400° C.), sheath gas flow (12 L/min), capillary voltage (4000v), and nozzle voltage (500v). Liquid chromatography conditions with an a Phenomenex Gemini C18 column 4.6×50 mm 5 µm particle size was used for separation. Chromatography method the following flow rate=0.4 mLs/min; solvent A=5 mM ammonium formate in 5% MeOH and 0.1% formic acid v/v/v; solvent B=80% 2-propanol, 15% methanol, 5% water and 0.1% formic acid (v/v/v/v). The gradient started at 20% A and progressed to 100% A in 10 minutes and maintained for the next 10 minutes. The column was re-equilibrated to starting conditions for 5 minutes before the next injection. An internal standard of non-native LacCer (18:1/12:0) was utilized since a stable isotope version was not available. Standard curve mixture was analyzed at various concentrations between 0.10 nM to 3.3 µM in LacCer (d18:1/16:0) and an internal standard concentration of 1 µM. The lower limit of quantification was estimated at 1 nM and a $R^2$ of 0.9969 was obtained using linear regression analysis. A standard curve with the internal standard doped in was run between 1 nM to 3.3 µM. Since the standards were only available only for LacCer (18:1/16:0), the values for LacCer (18:1/18:0) assumes that the relative ionization efficiency for the two closely related lipids is identical.

Extraction of Lipids.

The brain tissue was weighed and homogenized using a Dounce homogenizer (VWR), in the extraction solvent using a Bligh and Dyer type liquid-liquid extraction. All solvents were obtained from Sigma-Aldrich in ultra-high purity. The internal standard LacCer (18:1/12:0) was dissolved in 2:1 chloroform-methanol v/v. 6 ml of 2:1 chloroform-methanol and 2 ml of PBS. After approximately 2 minutes of homogenization, the liquid was transferred to a 8 ml glass vial. The mixture was spun in a high speed centrifuge at 1000 g for 20 minutes. This resulted in the formation of a protein disk and insoluble materials in the middle. The bottom layer was removed using a glass Pasteur pipet and transferred to a clean vial for evaporation under a stream of gentle nitrogen. The dried sample was reconstituted in 100 µl of 2:1 chloroform-methanol, and analyzed using the HPLC-MS.

nCounter Gene Expression.

100-200 ng of total RNA was hybridized with reporter and capture probes for nCounter Gene Expression code sets (Mouse Inflammation Kit, or a custom made astrocyte-oriented probe set (Table S1)), according to manufacturer's instructions (NanoString Technologies). Data were normalized to spiked positive controls and housekeeping genes (nSolver Analysis system). Transcript counts less than the mean of the negative control transcripts plus 2 standard deviations for each sample were considered background.

Analysis of Gene Expression Data.

Nanostring generated gene expression data were analyzed by use of the Expander 6.06 platform[53]. Genes were clustered using the unbiased CLICK algorithm, and each cluster was further analyzed for enrichments in transcription factors binding sites (promoter analysis).

q PCR.

RNA was extracted with RNAeasy columns (Qiagen), or TRIzol® (Invitrogen), cDNA was prepared and used for qPCR and the results were normalized to gapdh (mice) or ACTIN (human). All primers and probes were from Applied Biosystems. Aldh1l1 (Mm03048957_m1), aqp4 (Mm00802131_m1), b4galt5 (Mm00480147_m1), b4galt6 (Mm00480045_m1), ccl5 (Mm01302427_m1), cd19 (Mm00515420_m1), cd3e (Mm00599684_g1), cd40 (Mm00441891_m1), csf2 (Mm01290062_m1), cxcl10 (Mm00445235_m1), emr1 (Mm00802529_m1), foxp3 (Mm00475162_m1), gapdh (Mm00484668_m1), gfap (Mm01253033_m1), h2-Aa (Mm00439211_m1), Ifng (Mm01168134_m1), Il10 (Mm00439614_m1), il17a (Mm00439618_m1), il1b (Mm00434228_m1), il6 (Mm00446190_m1), irf1 (Mm01288580_m1), itgam (Mm00433455_m1), itgax (Mm00498698_m1), klrb1c (Mm00824341_m1), mbp (Mm01266402_m1), mog (Mm00447824_m1), nos2 (Mm00440502_m1), relb (Mm00485664_m1), snap25 (Mm00456921_m1), spp1 (Mm00436767_m1), syt1 (Mm00436858_m1), tbx21 (Mm00450960_m1), tgfb1 (Mm01178820_m1), tlr2 (Mm00442346_m1), tnf (Mm00443260_g1), vim (Mm01333430_m1), ACTB (Hs01872448_s1), B4GALT5 (Hs00941041_m1), B4GALT6 (Hs00153133_m1), CCL2 (Hs01060665_g1), CCL5 (Hs00941041_m1), IL6 (Hs00234140_m1), NOS2 (Hs00174575_m1), PTGST2 (Hs00191135_m1), and TLR2 (Hs00985639_m1).

T-Cell Proliferation and Cytokine Measurement.

Splenocytes and lymph node cells were cultured in X-VIVO medium and were plated for 72 h at a density of $5 \times 10^5$ cells per well in the presence of $MOG_{35-55}$ peptide. During the final 16 h, cells were pulsed with 1 Ci [3H] thymidine (PerkinElmer), followed by collection on glass fiber filters and analysis of incorporated [3H]thymidine in a-counter (1450 MicroBeta TriLux; PerkinElmer). Supernatants were collect after 48 h of culture for cytokine measurement by enzyme-linked immunosorbent assay[14]. For intracellular cytokine staining, cells were stimulated for 6 h with PMA (phorbol 12-myristate 13-acetate; 50 ng/ml; Sigma), ionomycin (1 µg/ml; Sigma) and monensin (GolgiStop; 1 ml/ml; BD Biosciences). After staining of surface markers, cells were fixed and made permeable according to the manufacturer's instructions BD Cytofix/Cytoperm™ Kit (BD Biosciences), or Foxp3 Fixation/Permeabilization (Ebiosceince).

Mouse Primary Microglia.

Mouse primary microglia were prepared as described[54] with minor modifications. Cerebral cortices from 1- to 3-day-old neonatal mice were dissected, carefully stripped of their meninges, digested with 0.25% trypsin, and dispersed into a single-cell level. The cell suspension ("mixed glia") was then cultured at 37° C. in humidified 5% CO2-95% air. Medium was replaced every 4-5 days. Mixed glia cultures reached confluence after 7-10 days, and were used to harvest microglia between 15 and 20 days after preparation. Microglia were isolated by the mild trypsinization procedure (Mild T/E) as previously described[54]. Briefly, treatment of the confluent mixed glial cultures with 0.06% trypsin (mild T/E) resulted in detachment of an intact layer of cells containing almost all the astrocytes and leaving behind a highly enriched population of microglia (>98%, as determined by staining with fluorescein-conjugated Griffonia simplicifolia isolectin B4 (IB4) (Vector Laboratories) or PE-conjugated CD11b Ab (data not shown)). The attached microglia were allowed to recover for 24-48 hours.

Mouse Primary Astrocytes.

Mix Glia was prepared as above, and incubated with 20 ug/ml biotin anti-IB4 (Vector Labs) for 20 min at RT, washed and incubated with Streptavidin—conjugated magnetic beads (Miltenyi Biotec) for 15 min at 4 C. Cells were washed, and cleared of $IB4^+$ cells (microglial and endothelial cells)[51] using cell separation Columns (Miltenyi Biotec). Cells were then cultured until confluent (day 7-10), the astrocyte monolayer was separated using the mild trypsinization procedure, separated into single cells suspension with Accutase (Invitrogen) and plated. Cells were >98% astrocytes, as determined by staining with GFAP or GLAST, with less than 2% contamination of $CD11b^+$ microglia cells (data not shown)).

Mouse Primary Leptomeningeal Phagocytes.

The meninges were carefully stripped from the brains of 1- to 3-day-old neonatal mice, and digested with 1% collagenase for 20 min at 37° C., and then dispersed into a single-cell level. Isolated cells, were incubated with anti-mouse CD16/CD32 for 15 min on ice to block the Fc receptors, and stained with APC-conjugated antibody for CD11b (M1/70) for 30 min at 4° C. Cells were washed, incubated with 7-AAD for exclusion of dead cells, and sorted.

Mouse Primary Choroid Plexus Cells.

Mouse primary choroid plexus cells were prepared as described[55,56] with minor modifications. In brief, the choroid plexus was removed from 1- to 3-day-old neonatal mice, digested with 1% collagenase for 20 min at 37° C., and then dispersed into a single-cell level. The cell suspension was washed in culture medium for choroid plexus cells [Dulbecco's modified Eagle medium/Ham's F12 (Invitrogen) supplemented with 10% foetal calf serum (Sigma-Aldrich), 1 mM 1-glutamine, 1 mM sodium pyruvate, 100 U/ml penicillin, 100 mg/ml streptomycin, 5 mg/ml insulin, 20 mM Ara-C) and cultured ($2.5 \times 10^5$ cells/well) at 37° C., 5% CO2 in poly-D-lysine coated 24-well plates. After 24 h, the medium was changed, and the cells were either left untreated or treated as described.

Plasmids.

The dual reporter construct expressing Gaussia luciferase under the murine Ccl2 promoter, and Secreted alkaline phosphatase (SEAP) under the CMV promoter (used for transfection normalization), was from GeneCopoeia, Inc. The construct encoding IRF1 was from Addgene. The pLenti-GFAP-EGFP-mir30-shAct1 vector[25] was a kind gift from Dr. Guang-Xian Zhang (Thomas Jefferson University, PA, USA).

In Vitro Knock-Down with shRNA.

The expression of LacCer synthases was knocked-down in C8-D30 astrocytes, using shRNA lentiviruses particles against b4galt5 (TRCN0000018782), b4galt6 (TRCN0000334278), or a non-targeting sequence (TRCN0000018782) as a control (Sigma). Astrocytes were incubated with lentiviruses and 8 µg/ml polybrene (both from Sigma-Aldrich) for 12 h, allowed to recover for 24 h, and were selected with puromycin (2 µg/ml). Gene knock-down in puromycin-resistant cells was verified by qPCR.

In Vivo Astrocyte-Specific Knock-Down with shRNA Lentivirus.

pLenti-gfap-egfp-mir30-shRNA harboring shRNA sequences against b4galt5, b4galt6, and a non-targeting shRNA were cloned using the pLenti-GFAP-EGFP-mir30-shAct1 vector[25] as a backbone, by replacing the shRNA for Act1 with the above-mentioned in vitro validated shRNA sequences (b4galt5: 5'-GCAGCCTGAATGACTCAGAT-TctcgagAATCTGAGTCATTCAGGCTGC-3' (SEQ ID NO:2), b4galt6: 5'-CGATGGACTGAACAATTTATTctcga-gAATAAATTGTTCAGTCCACG-3' (SEQ ID NO:3), and a non-targeting shRNA: 5'-GCGCGA-TAGCGCTAATAATTTctcgagAAATTATTAGCGCTA-TCGCGC-3' (SEQ ID NO:4)). Lentivirus particles were then generated by transfecting 293FT cells (Invitrogen) with 3 μg of the newly generated pLenti-GFAP-EGFP-mir30-shRNA vectors and 9 μg of the ViraPower™ Packaging mix (The helper plasmids pLP1, pLP2, pLP/VSV-G, Invitrogen). 48 h later supernatants were collected, filtered through a 0.45 μM PVDF filter, and concentrated over-night with the Lenti-X™ concentrator kit (Clontech) according to the manufacture's instructions. The viral titrate was determined using the Lenti-X™ qRT-PCR titration kit (Clontech) according to the manufacture's instructions, and stored at −70° C.

For in vivo injection, NOD EAE mice, 35 days after immunization (progressive phase) were anesthetized by an i.p. injection of ketamine (100 mg/kg) and xylazine (20 mg/kg) and placed in a Kopf Stereotaxic Alignment System. Using a Hamilton syringe, $1 \times 10^7$ IU/mouse of shB4galt5, shBrgalt5, shControl (non-targeting) virus were injected 0.44 mm posterior to the bregma, 1.0 mm lateral to it and 2.2 mm below the skull surface. Injection speed was maintained at 1 μl/minute to prevent leaking.

Viability Assay.

Astrocytes, microglia or Ly6Chigh monocytes were pre-treated with indicated concentrations of PDMP or LaCcer, and further activated with LPS/IFNγ (microglia and astro-cytes), CCL-2 (monocytes), or left untreated. Viability was assed following activation using the CellTiter-Fluor™ Cell viability assay (Promega).

Subcellular Fractionation and Immunoblot Analysis.

Astrocytes were treated as indicated, and total extracts (30 μg of protein), or the nuclear and cytoplasmic subcellular fractionations of cells, were separated by NuPAGE 10% Bis-Tris Gel (Invitrogen), and electroblotted onto supported nitrocellulose membrane. Subcellular fractionations were prepared using the NE-PER® Nuclear and Cytoplasmic Extraction kit (Pierce Biotechnology), according the manu-facture instruction. Blot were probed with Rabbit anti-IRF-1 (D5E4) XP®, Rabbit mAb, GAPDH (D16H11) XP®, Rab-bit mAb, Lamin B1 polyclonal Rabbit Abs, NF-κB p65 (D14E12) XP®, Rabbit mAb, followed by goat anti-rabbit IgG peroxidase conjugate Abs (all antibodies from Cell signaling). The blots were developed using the SuperSignal West Pico chemiluminescence kit (Pierce Biotechnology). Each blot was reprobed with GAPDH (total extract, or cytoplasmic fractionation) or Lamin B1 (nuclear fraction-ation) to verify protein uniformity. Data quantification was done using Image Studio software (Version 3.1.4) (LI-COR, Inc.)

Transfection and Luciferase Assay.

293T cells were grown in DMEM supplemented with 10% FBS, transfected with Fughene-HD Transfection Reagent (Roche) with the CCL2 dual-reporter and con-structs encoding IRF1, NF-κB p65, or an appropriate empty control. Luciferase and SEAP activity was analyzed 24 h after transfection with the Secrete-Pair Dual Luminescence Assay Kit (GeneCopoeia, Inc).

ChIP.

Cells were crosslinked with 1% formaldehyde for 15 min. Crosslinking was stopped by the addition of Glycine, and cells were lysed with 0.35 ml lysis buffer (1% SDS, 10 mM EDTA and 50 mM Tris-HCl, pH 8.1) containing 1× protease inhibitor 'cocktail' (Roche Molecular Biochemicals). Chro-matin was sheared by sonication and supernatants were collected after centrifugation and diluted in buffer (1% Triton X-100, 2 mM EDTA, 150 mM NaCl nd 20 mM Tris-HCl, pH 8.1). Antibody (5 μg) was prebound for 6 h to protein A and protein G Dynal magnetic beads (Invitrogen) and was washed three times with ice-cold 5% BSA in PBS, and then was added to the diluted chromatin and immuno-precipitated overnight (antibodies described below). Mag-netic bead-chromatin complexes were then washed three times in RIPA buffer (50 mM HEPES, pH 7.6, 1 mM EDTA, 0.7% sodium deoxycholate, 1% Nonidet-P40 and 0.5 M LiCl), followed by three times with Tris-EDTA buffer. Immunoprecipitated chromatin was then extracted with 1% SDS, 0.1 M NaHCO3 and heated for at least 8 h at 65° C. for reversal of the formaldehyde crosslinking DNA frag-ments were purified with a QIAquick DNA purification Kit (Qiagen) and analyzed by SYBR Green real-time PCR (primers described below). The following antibodies were used for ChIP: anti-IRF1 (SC-640x; Santa Cruz Biotechnol-ogy), anti-NF-κB p65 (ab7970; Abcam), and rabbit IgG (ab27478; Abcam). The following primer pairs were used: The following primer pairs were used: ccl2:NF-κB forward, 5'-CAGCTAAATATCTCTCCCGAAGG-3' (SEQ ID NO:5), and reverse, 5'-CATAGATGCCCACAGCTCAT-3' (SEQ ID NO:6); ccl2:ISRE forward, 5'-CTGCCAATTCTTC-CCTCTTTC-3' (SEQ ID NO:7), and reverse, 5'-GTGGGT-TGGA-ATTTGGTATTT-3' (SEQ ID NO:8); csf2:NF-κB forward, 5'-GACCAGATGGGTGGAGTGACC-3' (SEQ ID NO:9), and reverse, 5'-AGCCACACGCTTCTGGTTCC-3' (SEQ ID NO:10); csf2:ISRE forward, 5'-GCTTTC-GAGGGTCA-GATAACA-3' (SEQ ID NO:11), and reverse, 5'-CACACGCTTGGGCTAAGA-3' (SEQ ID NO:12); nos2:NF-κB(1) forward, 5'-CACAGACTAGGAGTGTC-CATCA-3' (SEQ ID NO:13), and reverse, 5'-GCAGCAGC-CATCAGGTATTT-3' (SEQ ID NO:14); nos2:ISRE/NF-κB (2) forward, 5'-ACCATGCGAAGATGAGTGGA-3' (SEQ ID NO:15), and reverse, 5'-AGCC-AGGAACACTACACA-GAA-3' (SEQ ID NO:16).

Monocytes Migration Assay.

Splenic Ly6C$^{high}$ monocytes were sorted (CD11b$^+$/F4-80$^+$, SSC$^{low}$/Ly6C$^{high}$), and seeded in the upper chamber of a 24-well cell culture insert with 3-μm pore-size (Corning). Cells were pre-treated with PDMP, LacCer, PDMP+LacCer or vehicle for 1 h. Then inserts were transferred to different wells with pre-warmed media containing CLL-2 (50 ng/ml, peprotech) or vehicle (PBS). Migrating monocytes were quantified in the lower chamber after 3 hr.

Human Primary Astrocytes.

Human fetal astrocytes were isolated as previously described[57] from human CNS tissue from fetuses at 17-23 wk of gestation obtained from the Human Fetal Tissue Repository (Albert Einstein College of Medicine, Bronx, N.Y.) following Canadian Institutes for Health Research-approved guidelines. Cultures were >90% pure.

MS Tissues.

Brain tissue was obtained from MS patients with clini-cally diagnosed and neuropathologically confirmed MS, non-MS CNS inflammatory diseases (NMSCID, including viral encephalitis, Rasmussen's encephalitis and ADEM and healthy controls. Autopsy samples were immediately frozen in liquid nitrogen. White matter MS tissue samples were selected as previously described[58]. All patients and controls, or their next of kin, had given informed consent for autopsy and use of their brain tissue for research purposes. Ethic approval was given prior to autopsy (CHUM ethic approval: SL05.022 and SL05.023 and BH07.001).

Statistical Analysis.

Prism software version 6.0e (GraphPad Software) was used for statistical analysis. P values of less than 0.05 were considered significant.

Example 1. LacCer Synthases Control CNS Inflammation and Neurodegeneration

Experimental autoimmune encephalomyelitis (EAE) induced in susceptible mouse strains constitutes a useful experimental model of MS. Different aspects of MS, however, are modeled by the EAE that develops in each mouse strain. C57BL/6 mice immunized with the myelin peptide $MOG_{35-55}$, for example, develop a monophasic form of EAE that resembles a single attack during RRMS. Immunization of non-obese diabetic (NOD) mice with the same antigen, however, leads to the development of an acute attack (acute phase), which is followed by a phase of progressive and irreversible accumulation of neurological impairment (progressive phase) that resembles SPMS[13,14].

Figure 9A:
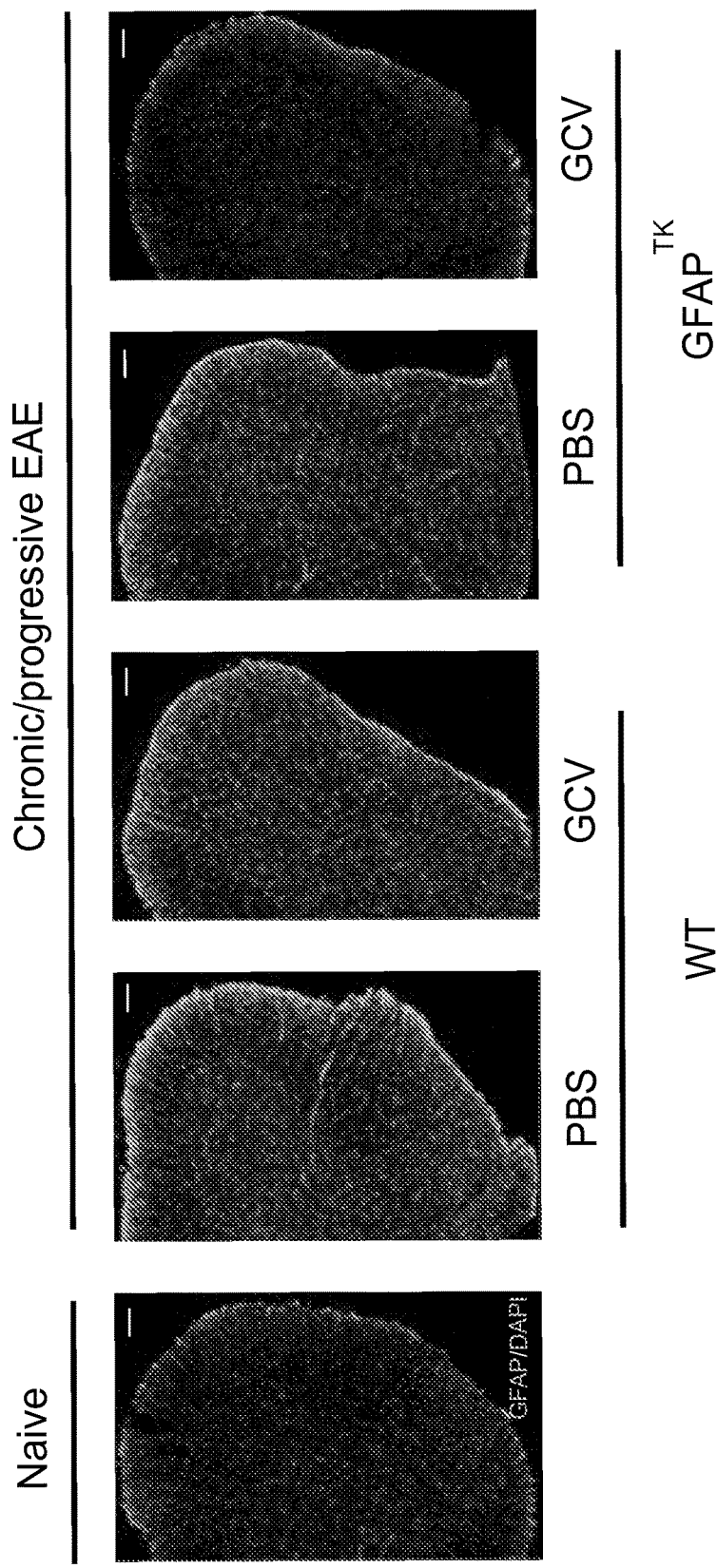
Figure 9B:
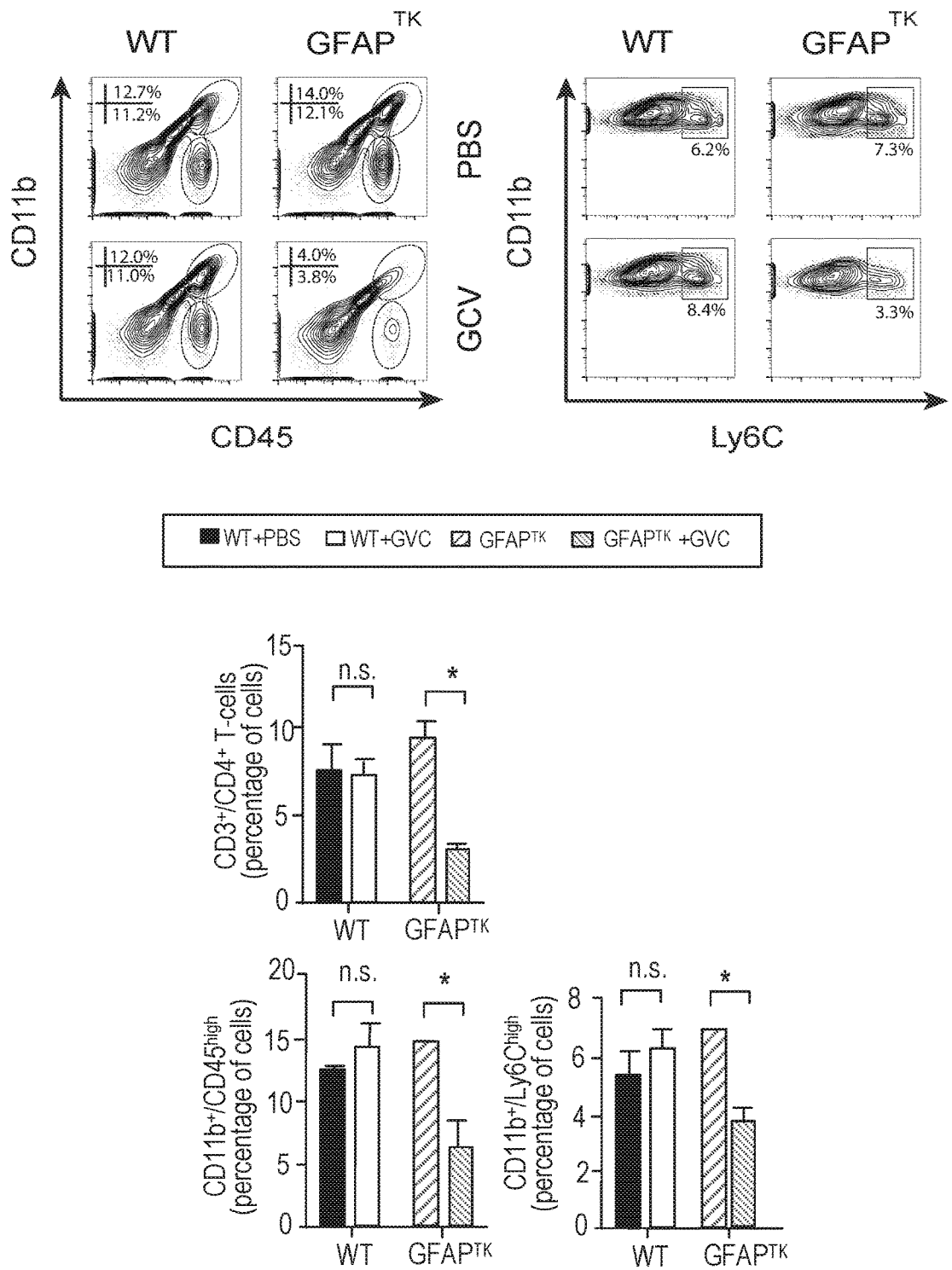
Figure 10D:
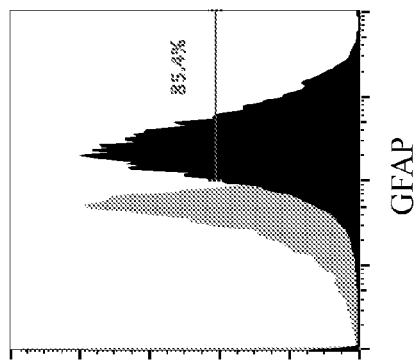
Figure 10C:
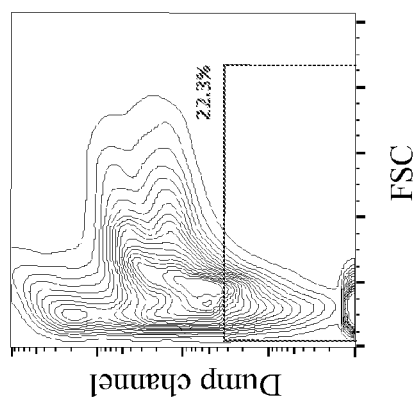
Figure 10B:
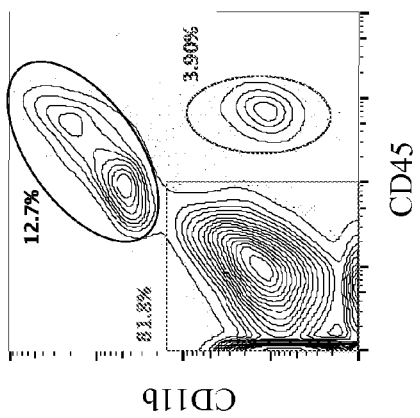
Figure 10A:
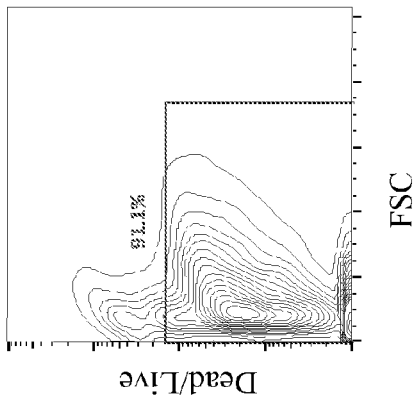
Figure 10E:
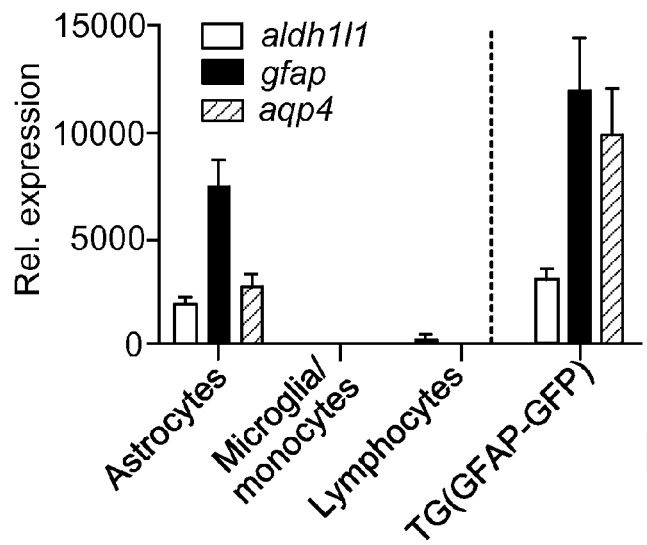
Figure 10F:
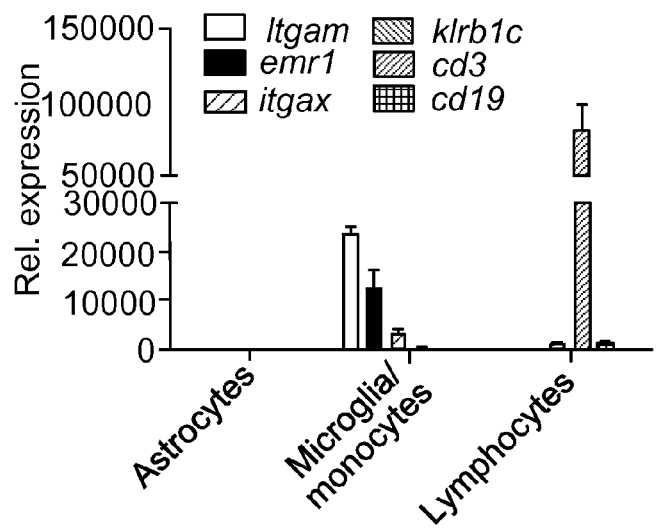
Figure 10G:
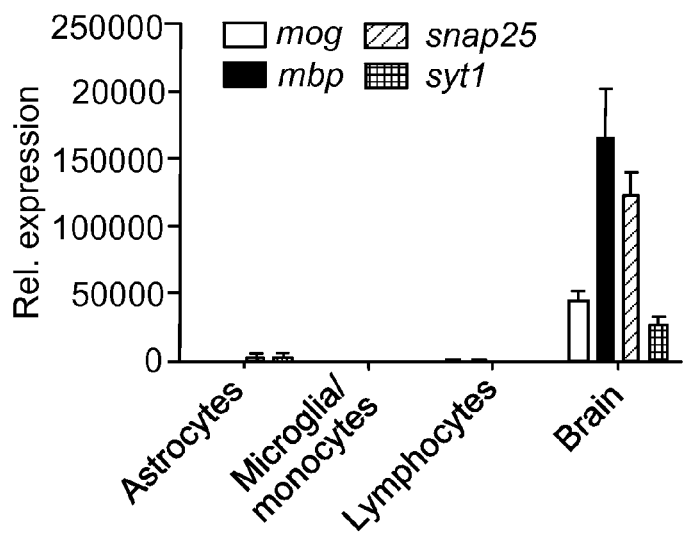

We recently found that F1 hybrid mice derived from breeding NOD and C57BL/6 mice also develop a chronic progressive form of EAE (FIGS. 8a-c). Thus, to study the role of astrocytes during CNS inflammation we analyzed the course of EAE in F1 NOD C57BL/6 GFAP-HSV-TK hybrid mice, in which reactive astrocytes can be depleted by Ganciclovir (GCV) administration (FIG. 9a). In accordance with previous findings in C57BL/6 mice[7,8], we found that the depletion of reactive astrocytes during the acute phase resulted in a significant worsening of EAE (FIG. 1a). However, astrocyte depletion during the progressive phase led to a significant amelioration of EAE (FIG. 1b). Moreover, although reactive astrocyte depletion in acute EAE results in increased monocyte and T-cell recruitment to the CNS[5,8], we found that depletion during the progressive phase of EAE decreased leukocyte infiltration in the CNS (FIG. 9b) but did not affect the peripheral T-cell response (FIGS. 9c,d). Of note, although GCV administration might potentially deplete neural progenitor cells (NPCs) in NOD C57BL/6 GFAP-HSV-TK hybrid mice, NPCs show protective effects in EAE[15,16]. Thus, these data suggest that depletion of reactive astrocytes is responsible for the amelioration of EAE.

Figure 11A:
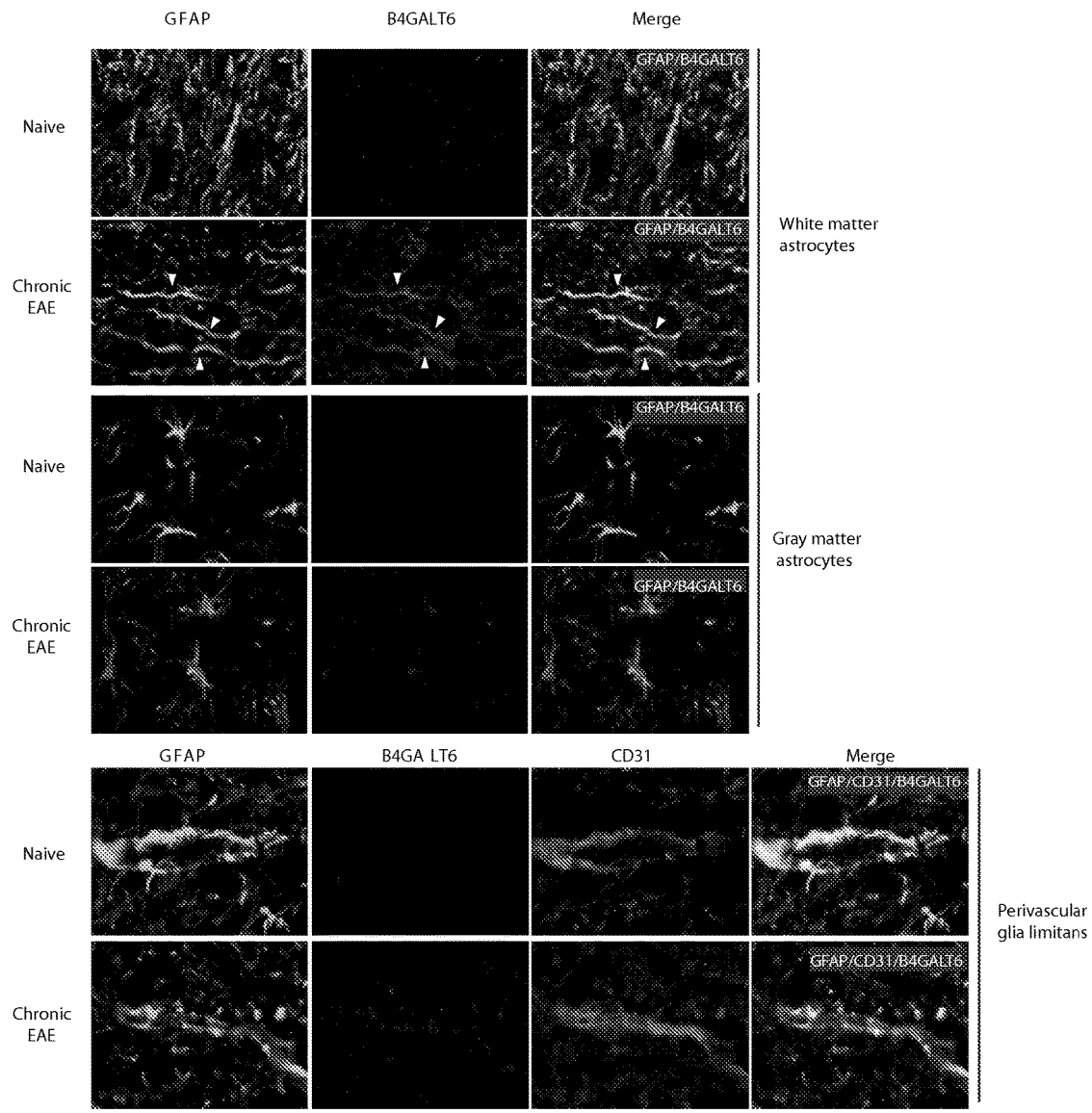
Figure 11B:
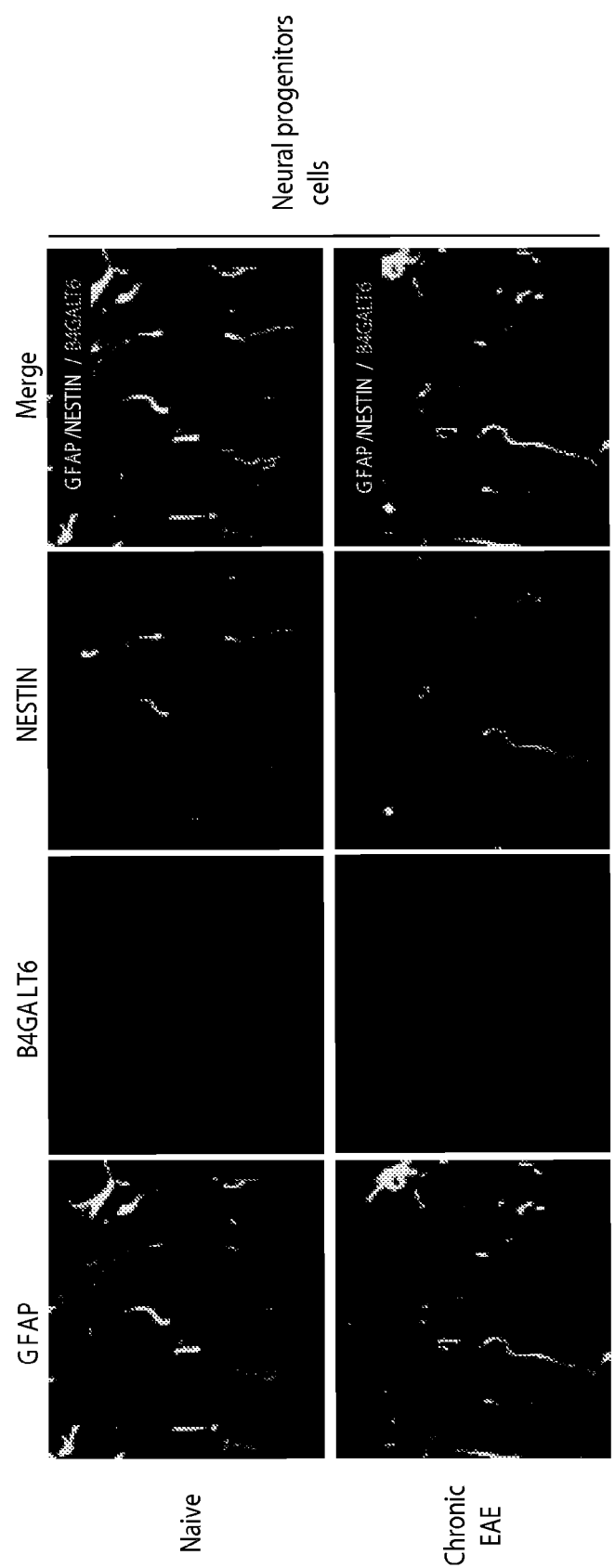
Figure 11C:
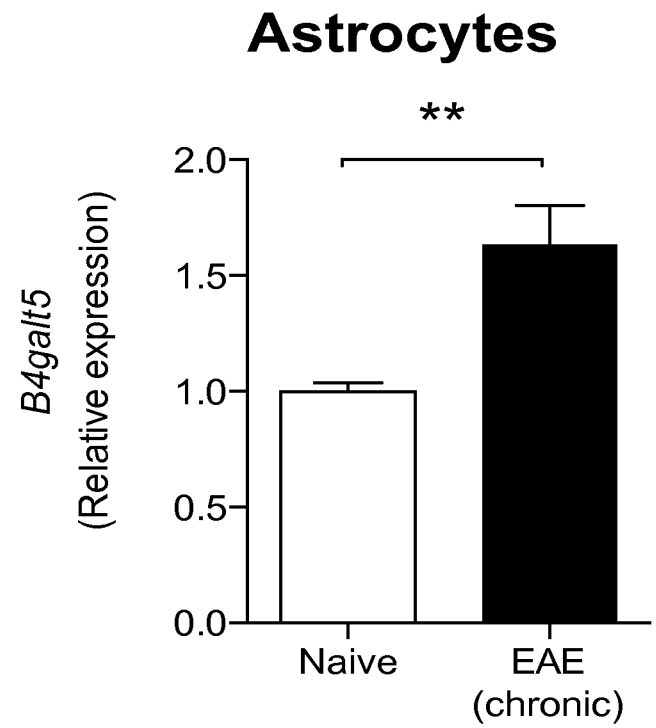
Figure 11D:
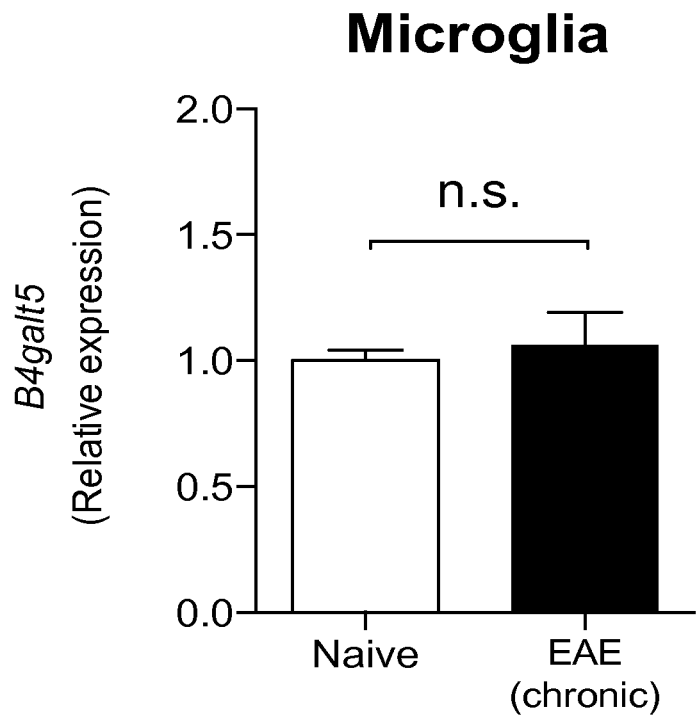

To study the molecular mechanisms controlling astrocyte activity during chronic autoimmune CNS inflammation we isolated astrocytes from naïve NOD mice, or during the acute and the progressive phases of EAE (FIGS. 10a-g), and analyzed their transcriptome using a custom made Nanostring nCounter array (Table 1). We found significant differences in the mRNA expression profile of astrocytes during the different stages of NOD EAE (FIG. 1c) and identified a unique cluster of genes up-regulated during the progressive phase (FIG. 1d). One of the genes whose expression was associated with progressive NOD EAE was b4galt6, a LacCer synthase[17]. Validation qPCR studies confirmed the up-regulation of B4galt6 expression in astrocytes during the progressive phase of NOD EAE, but not in microglial cells (FIG. 1e). Further validation by immunofluorescence (IF) detected B4GALT6 expression in white matter GFAP+ astrocytes, but not in gray matter, perivascular glia limitans, or in nestin+ neural progenitors (FIGS. 11a,b). In addition, we also detected a significant up-regulation of β-1,4-galactosyltransferase 5 (B4GALT5), which together with B4GALT6 are the only members of the B4GALT family with LacCer synthase activity[17] (FIG. 11c). Indeed, in agreement with the LacCer synthase activity of B4GALT5 and B4GALT6 (B4GALT5/6), we detected increased LacCer levels in the CNS of NOD mice during the progressive phase of EAE (FIG. 1f).

Figure 1G:
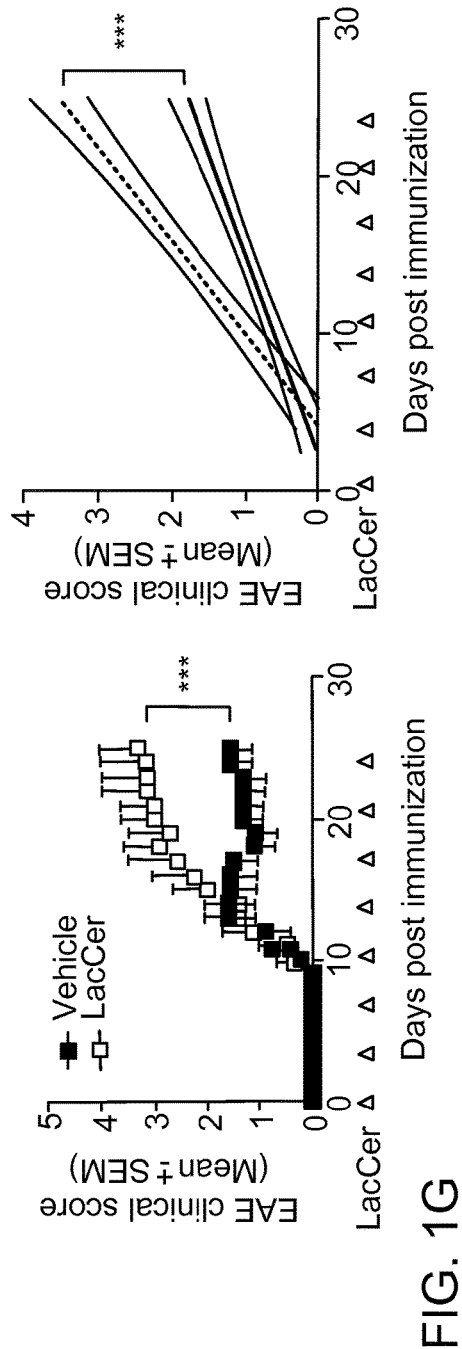
Figure 1H:
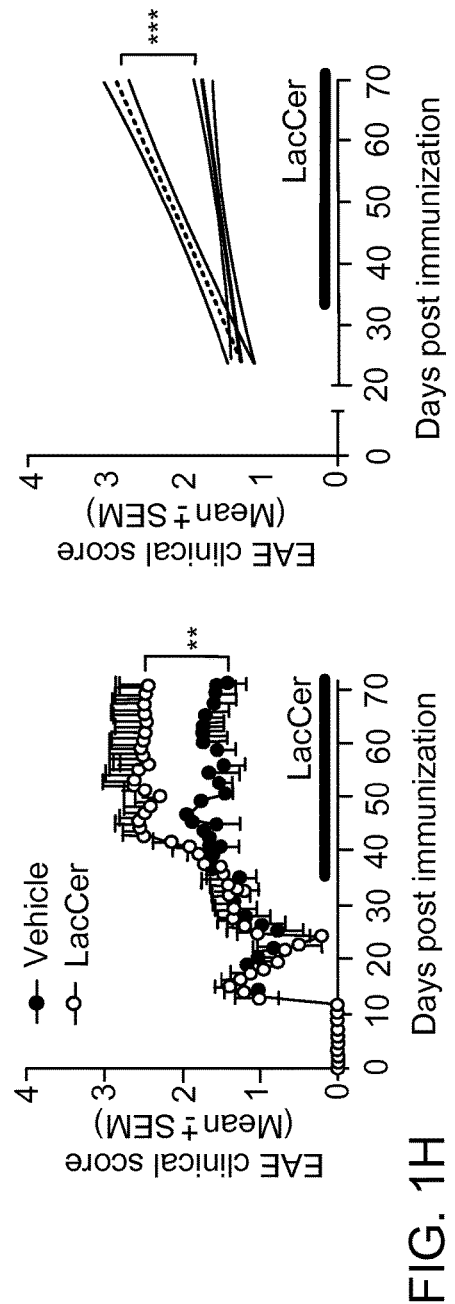

We then investigated the effects of LacCer on CNS inflammation. LacCer administration in the absence of MOG immunization did not result in the induction of EAE-like disease nor in astrocyte activation in vivo (FIG. 12a). However, LacCer administration resulted in a significant worsening of EAE in C57BL/6 mice (FIG. 1g). Similarly, LacCer administration initiated during the progressive phase, 35 days after EAE induction in NOD mice, also resulted in a significant worsening of disease clinical symptoms (FIG. 1h). Of note, the worsening of C57BL/6 and NOD EAE that followed LacCer administration was not linked to changes in the T-cell response (FIGS. 12b-e).

Figure 1I:
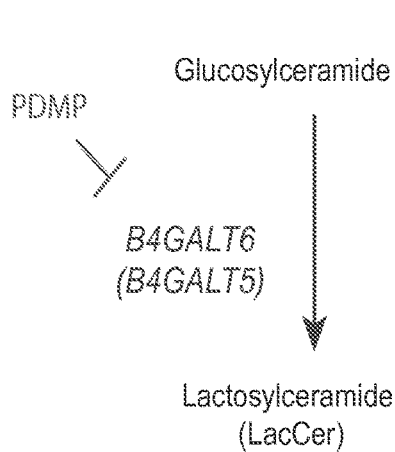
Figure 1J:
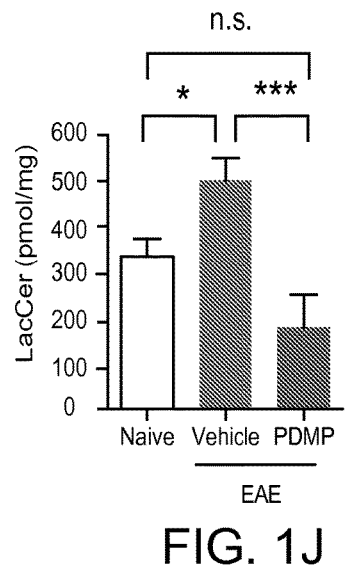
Figure 1L:
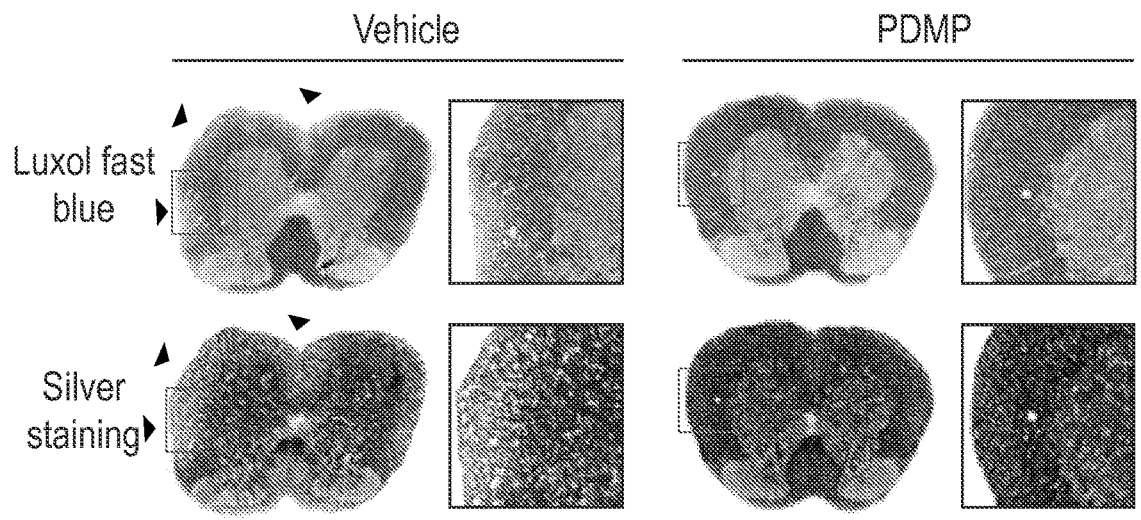
Figure 1K:
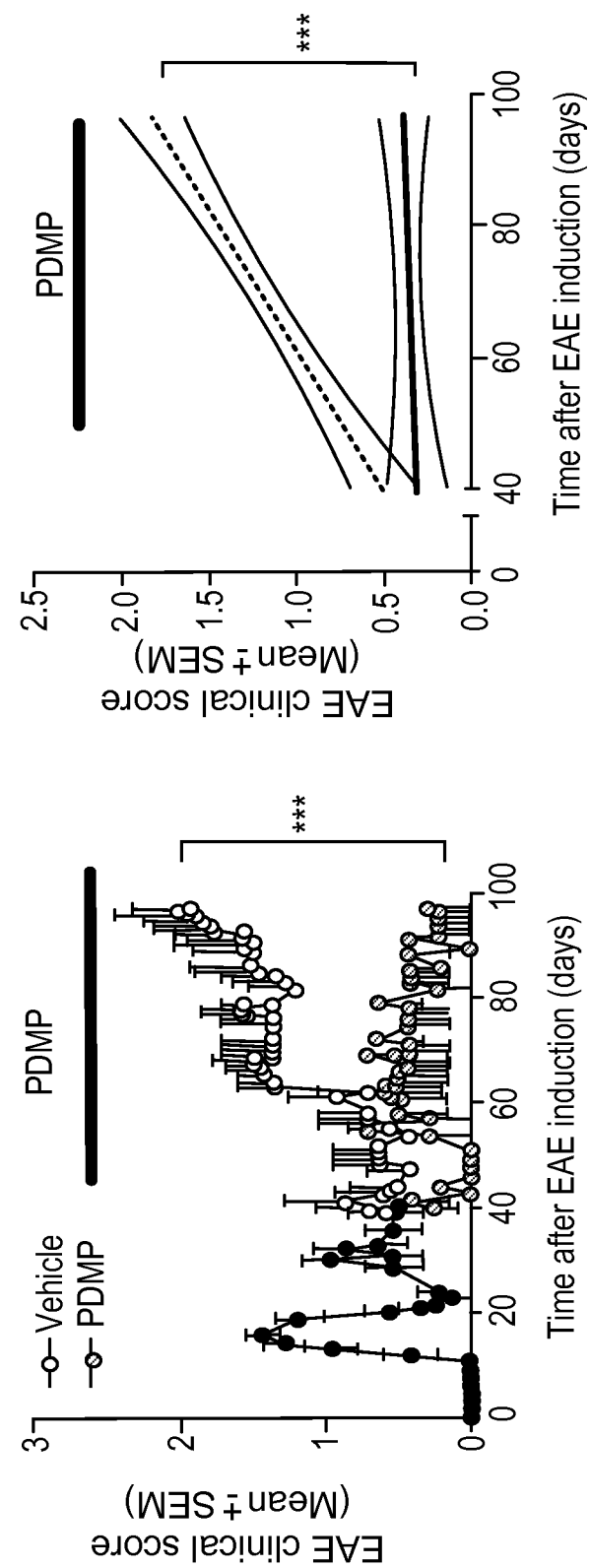

To further investigate the role of LacCer in the progressive phase of NOD EAE we inhibited its synthesis using the B4GALT5/6-specific inhibitor D-threo-1-phenyl-2-decanoylamino-3-morpholino-1-propanol (PDMP)[17] (FIG. 1i). Daily PDMP administration (20 mg/kg, twice a day) initiated 40 days after EAE induction resulted in a significant decrease in CNS LacCer levels (FIG. 1j) and a suppression of disease progression in terms of clinical score, demyelination and axonal loss (FIG. 1k,l). No significant changes, however, were detected in the T-cell response of PDMP-treated mice (FIGS. 12f-i). Taken together, these data suggest that LacCer produced by B4GALT5/6 plays a detrimental role in CNS inflammation.

TABLE 1

Astrocyte custom designed NanoString nCounter code set.

| Group | Symbol | Gene name |
|---|---|---|
| Target genes | Ahr | Aryl hydrocarbon receptor |
| | Akr1b10 | Aldo-keto reductase family 1, member B10 (aldose reductase) |
| | Aldh1l1 | Aldehyde dehydrogenase 1 family, member L1 |
| | Aqp4 | Aquaporin 4 |
| | Arg1 | Arginase, liver |
| | B4galt6 | UDP-Gal:betaGlcNAc beta 1,4-galactosyltransferase, polypeptide 6 |
| | Bcan | Brevican |
| | Bdnf | Brain derived neurotrophic factor |
| | Brunol4 | Bruno-like 4, RNA binding protein (*Drosophila*) |
| | Ccl2 | Chemokine (C—C motif) ligand 2 |
| | Ccl3 | Chemokine (C—C motif) ligand 3 |
| | Ccl4 | Chemokine (C—C motif) ligand 4 |
| | Ccl5 | Chemokine (C—C motif) ligand 5 |
| | Ccl7 | Chemokine (C—C motif) ligand 7 |
| | Ccl20 | Chemokine (C—C motif) ligand 20 |
| | Cd3e | CD3 antigen, epsilon polypeptide |
| | Cd19 | CD19 antigen |
| | Cd24a | CD24a antigen |
| | Cd274 | CD274 antigen |
| | Cd36 | CD36 antigen |
| | Cd38 | CD38 antigen |
| | Cd40 | CD40 antigen |
| | Cd80 | CD80 antigen |
| | Cd86 | CD86 antigen |
| | Cd163 | CD163 antigen |
| | Chi3l3 | Chitinase 3-like 3 (ym1) |
| | Ciita | Class II transactivator |
| | Csf1 | Colony stimulating factor 1 (macrophage) |
| | Csf2 | Colony stimulating factor 2 (granulocyte-macrophage) |
| | Csf3 | Colony stimulating factor 3 (granulocyte) |
| | Cspg4 | Chondroitin sulfate proteoglycan 4 |
| | Cxcl3 | Chemokine (C—X—C motif) ligand 3 |
| | Cxcl9 | Chemokine (C—X—C motif) ligand 9 |

TABLE 1-continued

Astrocyte custom designed NanoString nCounter code set.

| Group | Symbol | Gene name |
|---|---|---|
| | Cxcl10 | Chemokine (C—X—C motif) ligand 10 |
| | Cxcl11 | Chemokine (C—X—C motif) ligand 11 |
| | Cxcl12 | Chemokine (C—X—C motif) ligand 12 |
| | Cxcl15 | Chemokine (C—X—C motif) ligand 15 |
| | Cyp1a1 | Cytochrome P450, family 1, subfamily a, polypeptide 1 |
| | Ddx58 | DEAD (Asp-Glu-Ala-Asp) box polypeptide 58 (RIG-I) |
| | Dhx58 | DEXH (Asp-Glu-X-His) box polypeptide 58 (LPG2) |
| | Ebi3 | Epstein-Barr virus induced gene 3 |
| | Emr1 | EGF-like module containing, mucin-like, hormone receptor-like sequence 1 |
| | Entpd1 | Ectonucleoside triphosphate diphosphohydrolase 1 (CD39) |
| | Fasl | Fas ligand (TNF superfamily, member 6) |
| | Fgf2 | Fibroblast growth factor 2 |
| | Gfap | Glial fibrillary acidic protein |
| | Glul | Glutamate-ammonia ligase (glutamine synthetase) |
| | H2-Aa | Histocompatibility 2, class II antigen A, alpha |
| | H2-Ab1 | Histocompatibility 2, class II antigen A, beta 1 |
| | H2-Ea | Histocompatibility 2, class II antigen E alpha |
| | Icam1 | Intercellular adhesion molecule 1 |
| | Ifih1 | Interferon induced with helicase C domain 1 (MDA5) |
| | Ifnb1 | Interferon beta 1, fibroblast |
| | Ifng | Interferon gamma |
| | Ifnga | Interferon alpha |
| | Igf1 | Insulin-like growth factor 1 |
| | Il1b | Interleukin 1 beta |
| | Il2 | Interleukin 2 |
| | IL4ra | Interleukin 4 receptor, alpha |
| | Il6 | Interleukin 6 |
| | Il10 | Interleukin 10 |
| | Il10ra | Interleukin 10 receptor, alpha |
| | Il11 | Interleukin 11 |
| | Il12a | Interleukin 12a |
| | Il12b | Interleukin 12b |
| | Il13 | Interleukin 13 |
| | Il15 | Interleukin 15 |
| | Il17ra | Interleukin 17 receptor A |
| | Il17rc | Interleukin 17 receptor C |
| | Il21 | Interleukin 21 |
| | Il23a | Interleukin 23, alpha subunit p19 |
| | Il27 | Interleukin 27 |
| | Il27ra | Interleukin 27 receptor, alpha |
| | Il33 | Interleukin 33 |
| | Irf1 | Interferon regulatory factor 1 |
| | Irf2 | Interferon regulatory factor 2 |
| | Irf3 | Interferon regulatory factor 3 |
| | Irf4 | Interferon regulatory factor 4 |
| | Irf5 | Interferon regulatory factor 5 |
| | Irf6 | Interferon regulatory factor 6 |
| | Irf7 | Interferon regulatory factor 7 |
| | Irf8 | Interferon regulatory factor 8 |
| | Irf9 | Interferon regulatory factor 9 |
| | Itgam | Integrin alpha M (CD11b) |
| | Itgax | Integrin alpha X (CD11c) |
| | Ly6c1 | Lymphocyte antigen 6 complex, locus C1 |
| | Ly6g | lymphocyte antigen 6 complex, locus G |
| | Maf | Avian musculoaponeurotic fibrosarcoma (v-maf) AS42 oncogene homolog |
| | Marco | Macrophage receptor with collagenous structure |
| | Mbp | Myelin basic protein |
| | Mmp2 | Matrix metallopeptidase 2 |
| | Mmp9 | Matrix metallopeptidase 9 |
| | Mmp12 | Matrix metallopeptidase 12 |
| | Mog | Myelin oligodendrocyte glycoprotein |
| | Mrc1 | Mannose receptor, C type 1 |
| | Ncan | Neurocan |
| | Ncr1 | Natural cytotoxicity triggering receptor 1 |
| | Nfe2l2 | Nuclear factor, erythroid derived 2, like 2 |
| | Ngf | Nerve growth factor |
| | Nod1 | Nucleotide-binding oligomerization domain containing 1 |
| | Nod2 | Nucleotide-binding oligomerization domain containing 2 |
| | Nos2 | Nitric oxide synthase 2, inducible |
| | Nqo1 | NAD(P)H dehydrogenase, quinone 1 |
| | Ntf3 | Neurotrophin 3 |
| | Prom1 | Prominin 1 (CD133) |
| | Relb | Avian reticuloendotheliosis viral (v-rel) oncogene related B |
| | Retnla | Resistin like alpha |
| | Rnf146 | Ring finger protein 146 |
| | Slc1a2 | Solute carrier family 1 (glial high affinity glutamate transporter), member 2 |
| | Spp1 | Secreted phosphoprotein 1, osteopontin (OPN) |
| | Stat1 | Signal transducer and activator of transcription 1 |
| | Stat2 | Signal transducer and activator of transcription 2 |
| | Stat3 | Signal transducer and activator of transcription 3 |
| | Stat4 | Signal transducer and activator of transcription 4 |
| | Stat5a | Signal transducer and activator of transcription 5A |
| | Tdo2 | Tryptophan 2,3-dioxygenase |
| | Tgfb1 | Transforming growth factor, beta 1 |
| | Tgfb2 | Transforming growth factor, beta 2 |
| | Tgfb3 | Transforming growth factor, beta 3 |
| | Timp1 | Tissue inhibitor of metalloproteinase 1 |
| | Tiparp | TCDD-inducible poly(ADP-ribose) polymerase |
| | Tlr1 | Toll-like receptor 1 |
| | Tlr2 | Toll-like receptor 2 |
| | Tlr3 | Toll-like receptor 3 |
| | Tlr4 | Toll-like receptor 4 |
| | Tlr5 | Toll-like receptor 5 |
| | Tlr6 | Toll-like receptor 6 |
| | Tlr7 | Toll-like receptor 7 |
| | Tlr8 | Toll-like receptor 8 |
| | Tlr9 | Toll-like receptor 9 |
| | Tlr11 | Toll-like receptor 11 |
| | Tlr12 | Toll-like receptor 12 |
| | Tlr13 | Toll-like receptor 13 |
| | Tnf | Tumor necrosis factor |
| | Traf3ip2 | TRAF3 interacting protein 2 (ACT1) |
| | Vcam1 | Vascular cell adhesion molecule 1 |
| | Vegfa | Vascular endothelial growth factor A |
| | Vim | Vimentin |
| | Vwf | Von Willebrand factor homolog |
| House-keeping genes | Gapdh | Glyceraldehyde-3-phosphate dehydrogenase |
| | B2m | Beta-2 microglobulin |
| | Cltc | Clathrin, heavy polypeptide (Hc) |
| | Gusb | Glucuronidase, beta |
| | Hprt1 | Hypoxanthine guanine phosphoribosyl transferase 1 |
| | Pgk1 | Phosphoglycerate kinase 1 |
| | Tubb5 | Tubulin, beta 5 |

Example 2. B4GALT5/6 Inhibition Suppresses Astrocyte Activation During EAE

Figure 2A:
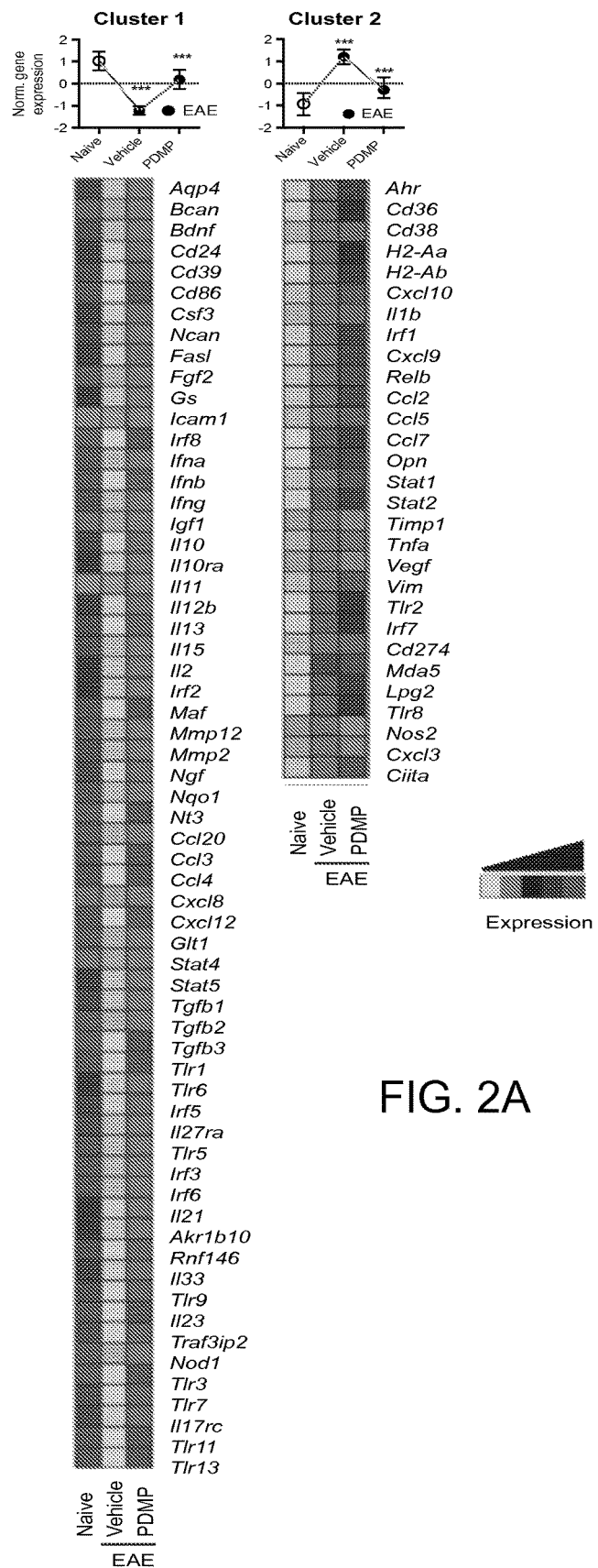
Figure 2B:
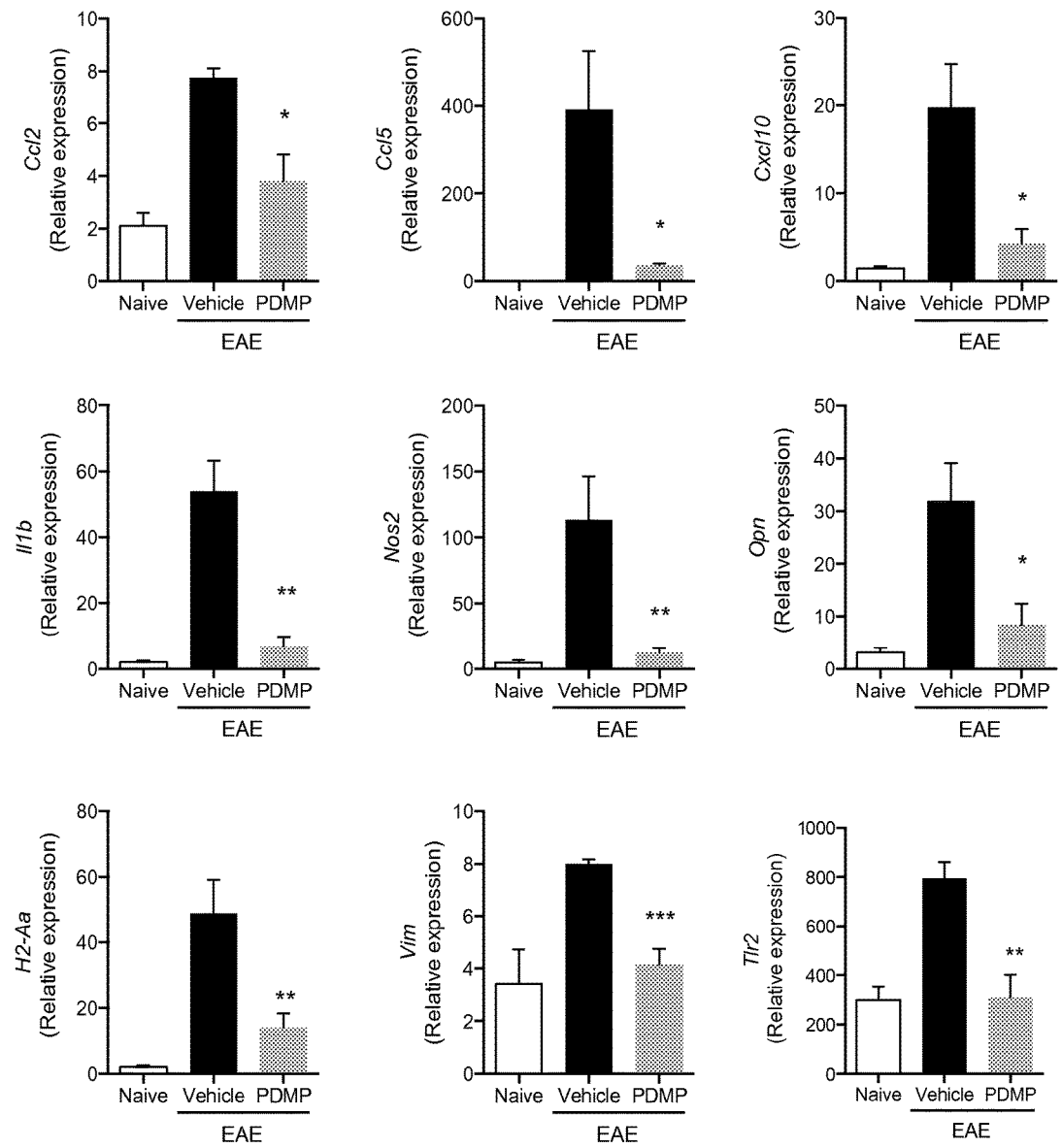

LacCer has been suggested to promote pathology during experimental spinal cord injury[18]. Thus, we studied the effects of B4GALT5/6 inhibition on the transcriptional program of astrocytes isolated from vehicle- or PDMP-treated NOD mice during the progressive phase of EAE (day 100). Our unbiased analyses identified two sets of genes: genes down-regulated during EAE and up-regulated by PDMP, and genes up-regulated during EAE and down-regulated by PDMP (clusters 1 and 2 in FIG. 2a, respectively). Cluster 2 included several genes associated with EAE and MS pathology: ccl2 (recruitment of inflammatory monocytes into the CNS)[19-21], ccl5 and cxcl10 (recruitment of peripheral immune cells to the CNS), IL-1β (il1b), osteopontin (opn), nitric oxide synthase (nos2), MHC-II (H2-Aa) and vimentin (vim, associated with astrocyte activation). Validation experiments by qPCR on independent samples confirmed the suppressive effects of PDMP on the expression of representative genes included in cluster 2 (FIG. 2b). Additional support for the role of B4GALT6 in regulating the expression of genes associated with EAE and MS pathology was provided by IF studies in which we detected co-expression of B4GALT6 with CCL2 and iNOS in GFAP+ astrocytes (FIG. 13).

Moreover, since astrocytes are reported to regulate re-myelination and neuronal viability[9,22], we analyzed the expression of genes associated with the control of myelination by astrocytes (Table 2 and FIG. 2c). In agreement with the demyelination and axonal damage shown in FIG. 11, we detected a significant up-regulation of genes associated with demyelination, and a down-regulation of genes associated with remyelination in the progressive phase of NOD EAE. However, B4GALT5/6 inhibition by PDMP resulted in a significant reduction in the expression of demyelination-associated genes concomitant with and increased expression of remyelination-associated genes (FIG. 2c). Collectively, these data demonstrate that B4GALT5/6 controls astrocyte activation during EAE.

To identify the molecular mechanisms mediating the effects of B4GALT5/6 blockade on the transcriptional response of astrocytes during EAE, we searched the promoter sequence of the genes included in clusters 1 and 2 for the enrichment of specific transcription factor binding sites. We found that genes included in cluster 2, whose expression was suppressed by B4GALT5/6 inhibition, were enriched for interferon-sensitive response elements (ISREs) ($P=4.83\times10^{-6}$) and NF-κB response elements ($P=9.99\times10^{-6}$). Additional support for the participation of these pathways during the regulation of EAE by B4GALT5/6 was provided by the up-regulation of irf1 and relB expression detected during EAE, and its subsequent suppression when LacCer synthesis was inhibited with PDMP (FIG. 2d,e). Taken together, these results suggest that B4GALT5/6 controls NF-κB and IRF-1 activation during CNS inflammation.

TABLE 2

Astrocyte genes associated with the control of myelination and neuronal viability/axonal growth as previously described[9,59].

| Demyelination | | Remyelination | |
|---|---|---|---|
| Bcan | Il12 | Bdnf | Il4 |
| Ccl2 | Icam | Cd274 | Il5 |
| Ccl5 | Il1b | Cntf | Lif |
| Cd24 | Il23 | Csf1 | Mmp12 |
| Cd40 | Il33 | Ctla4 | Mmp9 |
| Cd80 | Il6 | Cxcl1 | Ngf |
| Cd86 | Mmp2 | Cxcl12 | Nos2 |
| Csf2 | Ncan | Cd95l | Nrf2 |
| Cx3cl1 | Nos2 | Fgf2 | Nt3 |
| Cxcl10 | Opn | Gs | Ntf4 |
| Cxcl8 | TNFa | Igf1 | Pdgf |
| Gfap | Traf3ip2 | Il10 | Slc1a2 |
| H2-Aa | Vcam | Il11 | Tgfb1 |
| H2-Ab | Vim | Il27 | Timp1 |

Example 3. LacCer Produced by B4GALT6 Acts in an Autocrine Manner to Boost Astrocyte Activation To investigate whether LacCer produced by B4GALT5/6 acts directly on murine astrocytes to regulate their activity, we studied the effects of B4GALT5/6 inhibition and LacCer supplementation on the transcriptional response of primary astrocytes to activation. We found that B4GALT5/6 inhibition suppressed the transcriptional response of astrocytes to stimulation with lipopolysaccharide and interferon-γ (LPS/IFNγ) (FIGS. 3a,b and FIG. 14a). Conversely, supplementation with exogenous LacCer boosted the response of astrocytes to LPS/IFNγ, suggesting that LacCer synthesized by B4GALT5/6 acts on an autocrine manner to promote astrocyte activation under these experimental conditions (FIGS. 3a,b and FIG. 14a). Consistent with this interpretation, exogenous LacCer overcame the suppressive effects of PDMP on astrocyte activation (FIGS. 3a,b and FIG. 14a). Of note, PDMP or LacCer treatment did not affect astrocyte viability (FIGS. 14b,c) and similar effects of PDMP and LacCer were detected when we analyzed their effects on astrocytes activated with IL-1β, poly(I:C), or the combination of IFNγ and IL-17 produced by encephalitogenic T cells.

To analyze the relative contribution of B4GALT5 and B4GALT6 on astrocyte activation[17,23,24], we knocked-down down b4galt5 and b4galt6 expression using validated lentivirus-delivered shRNAs (FIG. 3c). We found that the knock-down of b4galt6 significantly suppressed the up-regulation of h2-Aa, ccl5 and cxcl10 expression triggered by LPS/IFNγ activation, to a similar extent than PDMP treatment. However, the knock-down of b4galt5 did not affect the expression of those genes (FIGS. 3d-f), suggesting that B4GALT6 plays a dominant role in the regulation of astrocyte activation by LacCer. Of note, PDMP treatment of astrocytes in which B4GALT6 had been knocked down with shRNA did not further suppress h2-Aa, ccl5 and cxcl10 expression, suggesting that the effects of PDMP result from the specific inhibition of B4GALT6-dependent LacCer synthesis (FIG. 14d).

Figure 3G:
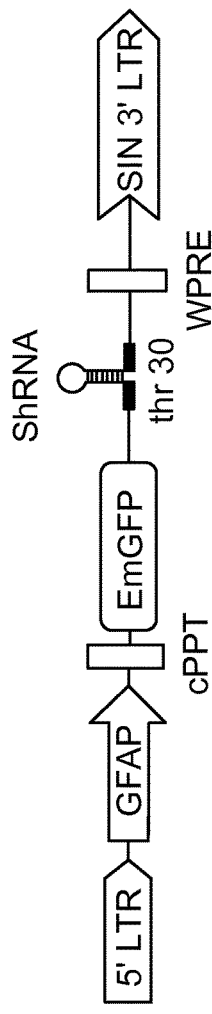
Figure 3H:
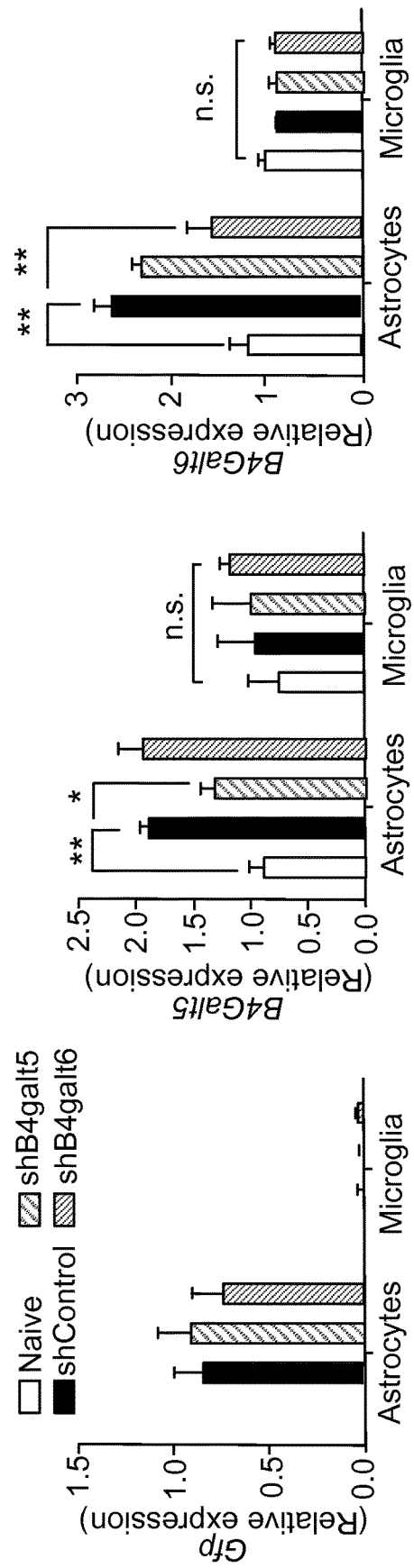
Figure 3I:
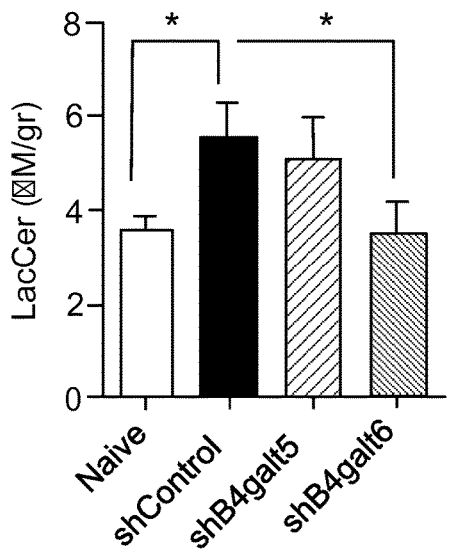
Figure 3J:
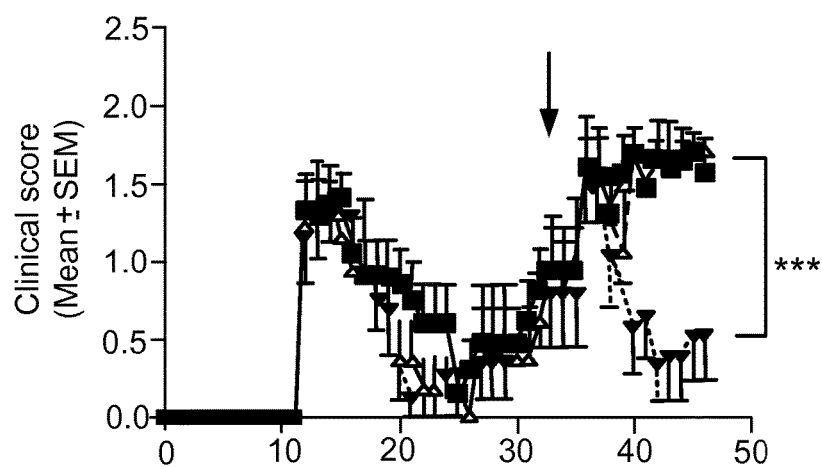
Figure 3J:
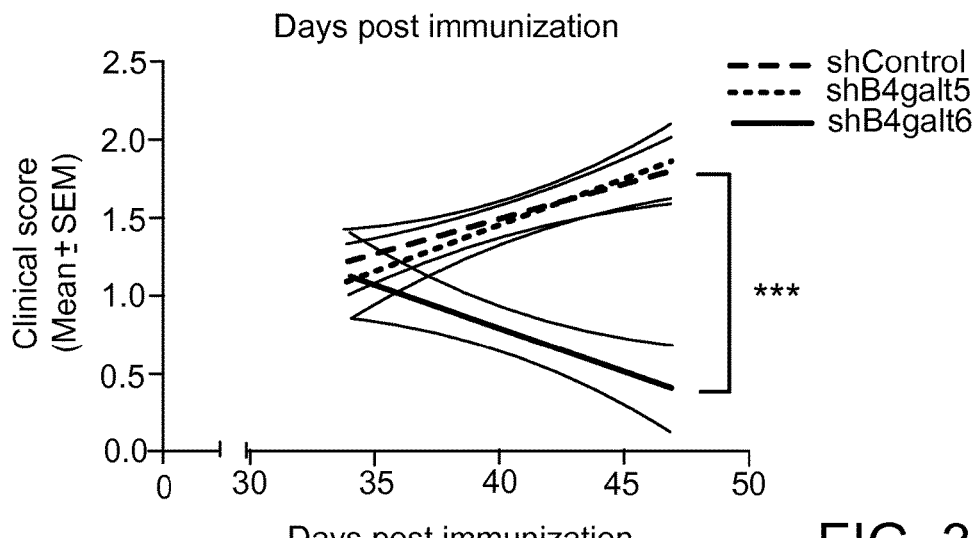

To determine the relative contribution of B4GALT5 and B4GALT6 on astrocyte activation in vivo and the control of EAE progression, we delivered the shRNAs to NOD mice using a lentivirus-based system optimized for astrocyte-specific knock-down in vivo[25] (FIG. 3g). In this system, the mouse gfap promoter drives the expression of an shRNA of choice and a GFP reporter. Following intra-cerebroventricular (i.c.v.) injection of shRNA-encoding lentivirus during the progressive phase, 35 days after EAE induction in NOD mice, we detected expression of the GFP reporter restricted to GFAP+ astrocytes but not Iba1+ microglia and inflammatory macrophages (FIG. 3h and FIG. 14e). Consequently, we detected an astrocyte-specific knock-down of b4galt6 and b4galt5 expression (FIG. 3h). The knock down of b4galt6, but not of b4galt5, led to a significant decrease of CNS LacCer levels during the progressive phase of NOD EAE (FIG. 3i). Moreover, the knock down of b4galt6, but not of b4galt5, suppressed disease progression in NOD mice (FIG. 3j). Taken together, these data show that LacCer produced by B4GALT6 acts in an autocrine manner to promote astrocyte activation and EAE progression.

To investigate the molecular mechanisms mediating the effects of LacCer on astrocyte activation, we searched the promoters of genes regulated by LacCer in primary astrocytes in culture (FIG. 3a) for enrichment in specific TF binding sites. Similar to our findings in astrocytes isolated from NOD mice treated with PDMP, we detected a significant enrichment ($P<10^{-5}$) in NF-κB and ISRE responsive elements.

It has been previously reported that LacCer activates NF-κB in astrocytes[18,26]. Accordingly, we found a decreased translocation of NF-κB to the nucleus following B4GALT6 inhibition; conversely, exogenous LacCer triggered NF-M3 activation, and even abrogated the inhibition induced by PDMP (FIG. 14f). The role of IRF1/ISRE in the regulation of astrocyte activity by LacCer, however, is unknown. We found that LacCer treatment enhanced the translocation of IRF-1 to the nucleus, whereas B4GALT6 inhibition interfered with this process (FIG. 3k). Moreover, in chromatin immunoprecipitation (ChIP) experiments we detected a significant recruitment of NF-κB and IRF-1 to the nos2 promoter in astrocytes activated with LPS/IFNγ (FIG. 3l). To study the functional relevance of IRF-1 on the response of astrocytes to LacCer we compared the response of WT and IRF-1 deficient astrocytes to activation with LPS/IFNγ. We found that IRF-1 deficiency abrogated the up-regulation triggered by LacCer of nos2 and other genes that harbor ISRE biding sites in their promoters (csf2, ccl2, ccl5, il6 and tlr2) (FIG. 3m). Further support for a role of IRF-1 in the regulation of ccl2 and nos2 expression during progressive NOD EAE was provided by the co-expression of IRF-1 with CCL-2 and iNOS detected by IF in GFAP+ astrocytes (FIG. 14g). Taken together, these results demonstrate that LacCer produced by B4GALT6 acts in an autocrine manner to activate astrocytes through NF-κB and IRF-1 dependent pathways.

Example 4. B4GALT6 Regulates Ccl2 Transcriptional Activity in Astrocytes

The recruitment of inflammatory monocytes into the CNS driven by CCL-2 is thought to promote neurodegeneration and disease progression in MS and EAE[19-21,27]. We found that B4GALT6 and LacCer control ccl2 expression by astrocytes (FIGS. 2a,b and 3a). Based on our findings on the effects of LacCer on the activation of NF-κB and IRF-1 in astrocytes, we searched the ccl2 promoter for responsive elements to these transcription factors. Our bioinformatic studies identified potential binding sites for NF-κB and IRF-1 (FIG. 4a). To evaluate their functional relevance, we used a reporter construct containing the luciferase gene under the control of the ccl2 promoter. We found that IRF-1 and NF-κB (p65) significantly transactivated the ccl2 promoter (FIG. 4b). Moreover, in ChIP studies we detected a significant recruitment of NF-κB and IRF-1 to the ccl2 promoter in astrocytes activated with LPS/IFNγ (FIG. 4c). This recruitment was arrested by the inhibition of LacCer synthesis with PDMP, and the effects of PDMP could be abrogated by the addition of exogenous LacCer (FIG. 4c). Thus, LacCer produced by B4GALT6 controls ccl2 expression.

Figure 4E:
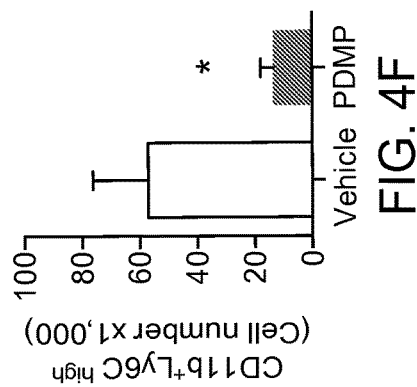
Figure 4F:
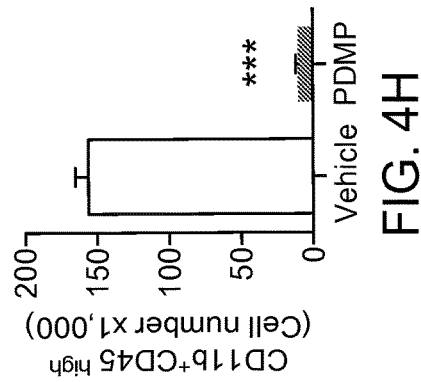
Figure 4G:
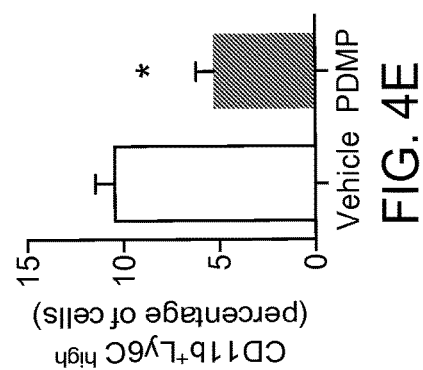
Figure 4H:
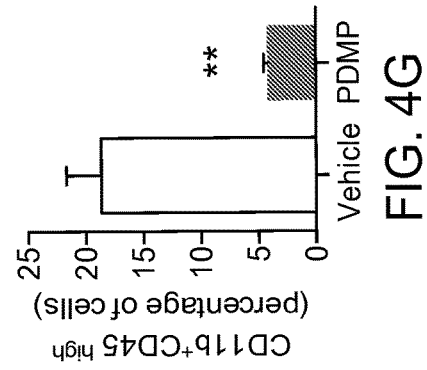
Figure 4D:
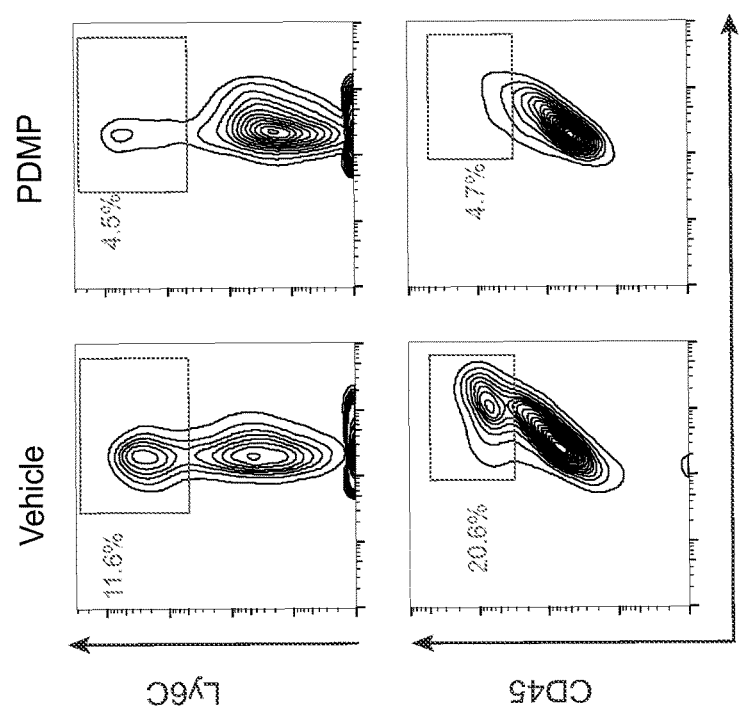

To investigate the in vivo relevance of the regulation of ccl2 expression by B4GALT6-LacCer we analyzed the recruitment of inflammatory monocytes into the CNS of NOD EAE mice treated with vehicle or with the B4GALT6 inhibitor PDMP. We found that B4GALT6 inhibition significantly reduced the frequency and the total numbers (FIGS. 4d-h) of inflammatory monocytes (defined either as of CD11b+Ly6C$^{high}$ or CD11b+CD45$^{high}$ cells) recruited to the CNS during EAE. Similar results were also obtained when B4GALT6 was knocked-down in astrocytes using lentivirus-delivered shRNAs during the chronic phase of NOD EAE (FIG. 4i). Thus, B4GALT6 controls the production of CCL-2 and the recruitment of inflammatory monocytes into the CNS. Of note, the inhibition of B4GALT6 or treatment with LacCer did not affect the viability of purified Ly6C$^{high}$ monocytes, their migration in a CCL-2 gradient, or their response to LPS/IFNγ stimulation (FIGS. 4j-m), suggesting that B4GALT6/LacCer does not act directly in monocytes to control their recruitment to the CNS.

Figures 5A, 5B:
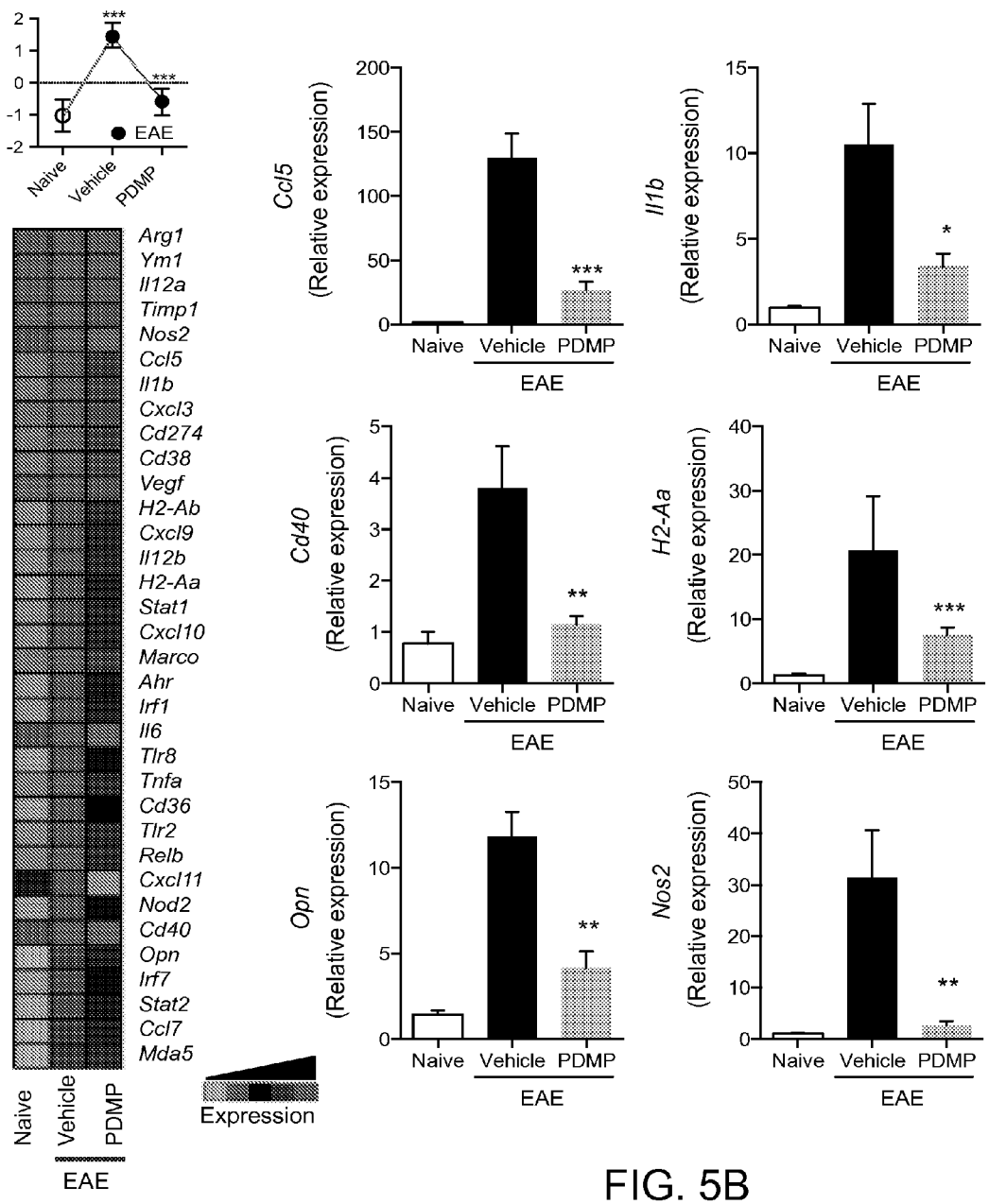
Figure 5C:
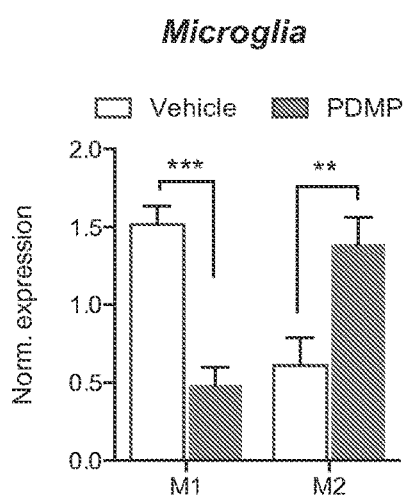
Figure 5D:
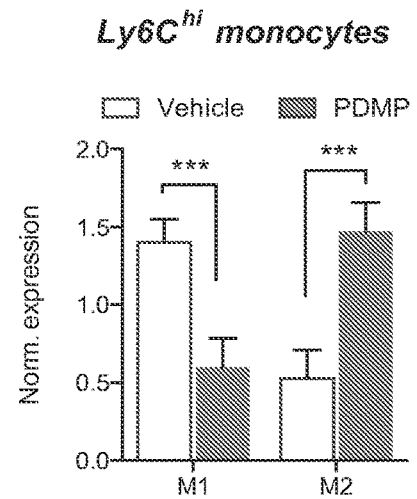
Figure 5E:
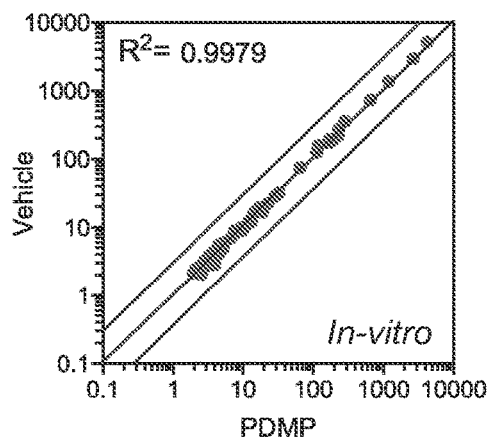
Figure 5F:
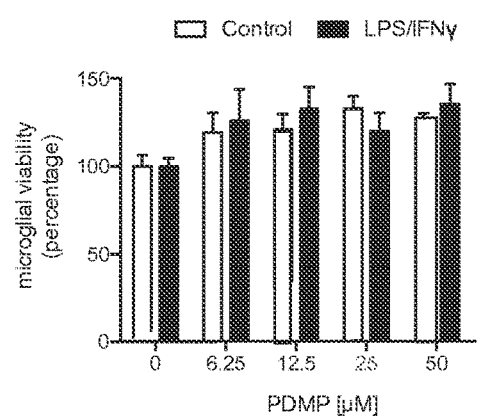
Figure 5G:
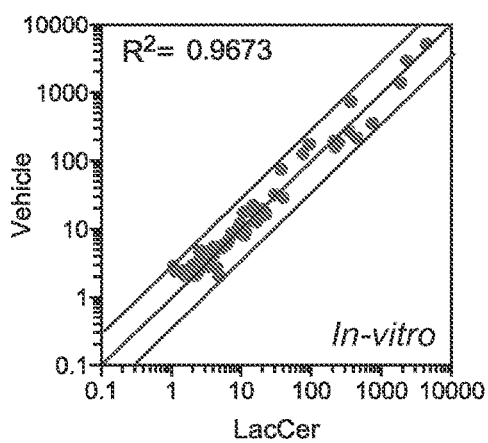
Figure 5H:
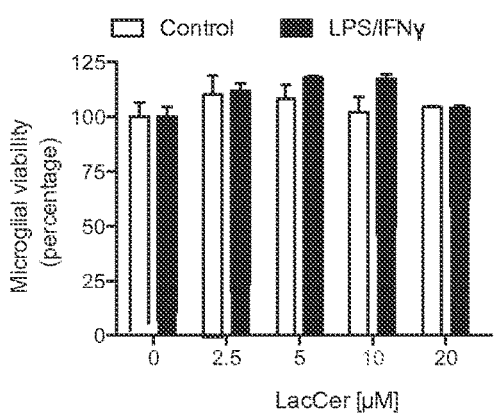

Example 5. B4GALT6 in Astrocytes Regulates the Activation of Microglia and CNS-Infiltrating Monocytes Microglia play a central role in the control of CNS inflammation[28]. To study the effects of B4GALT5/6 on microglia, we isolated microglial cells from naïve mice, or during the progressive phase of NOD EAE in vehicle- or PDMP-treated mice, and analyzed their transcriptional profile by NanoString nCounter. We found that B4GALT5/6 inhibition reduced the expression of genes associated with microglia activation during EAE (FIGS. 5a,b). To further analyze the effects of B4GALT5/6 inhibition on microglia and CNS-infiltrating monocytes, we studied the expression of genes associated with pro- or anti-inflammatory phenotypes (M1 or M2, respectively) in the macrophage/monocyte lineage, thought to affect disease pathology in MS and EAE[29-31]. We found that B4GALT5/6 inhibition led to a significant down regulation of M1-associated genes, concomitant with an up-regulation of M2-associated genes in microglia and CNS-infiltrating monocytes (FIGS. 5c,d and Table 3). Thus, although B4GALT5/6 are not up-regulated by microglia during EAE, LacCer modulates the activation of microglia and CNS-infiltrating monocytes.

Given that B4GALT5/6 inhibition in vivo altered the M1/M2 balance in microglia and CNS-infiltrating monocytes (FIGS. 5c,d), we studied whether the effects of B4GALT5/6 and LacCer in microglia and monocytes were cell autonomous. We found that neither the viability nor the response of cultured primary mouse microglia to LPS/IFNγ was affected by the inhibition of B4GALT5/6 or the addition of LacCer in the absence of astrocytes (FIGS. 5e-h). In addition, LacCer did not affect the transcriptional response to activation of either leptomeningeal phagocytes or choroid plexus cells (FIGS. 15a,b).

Figure 5I:
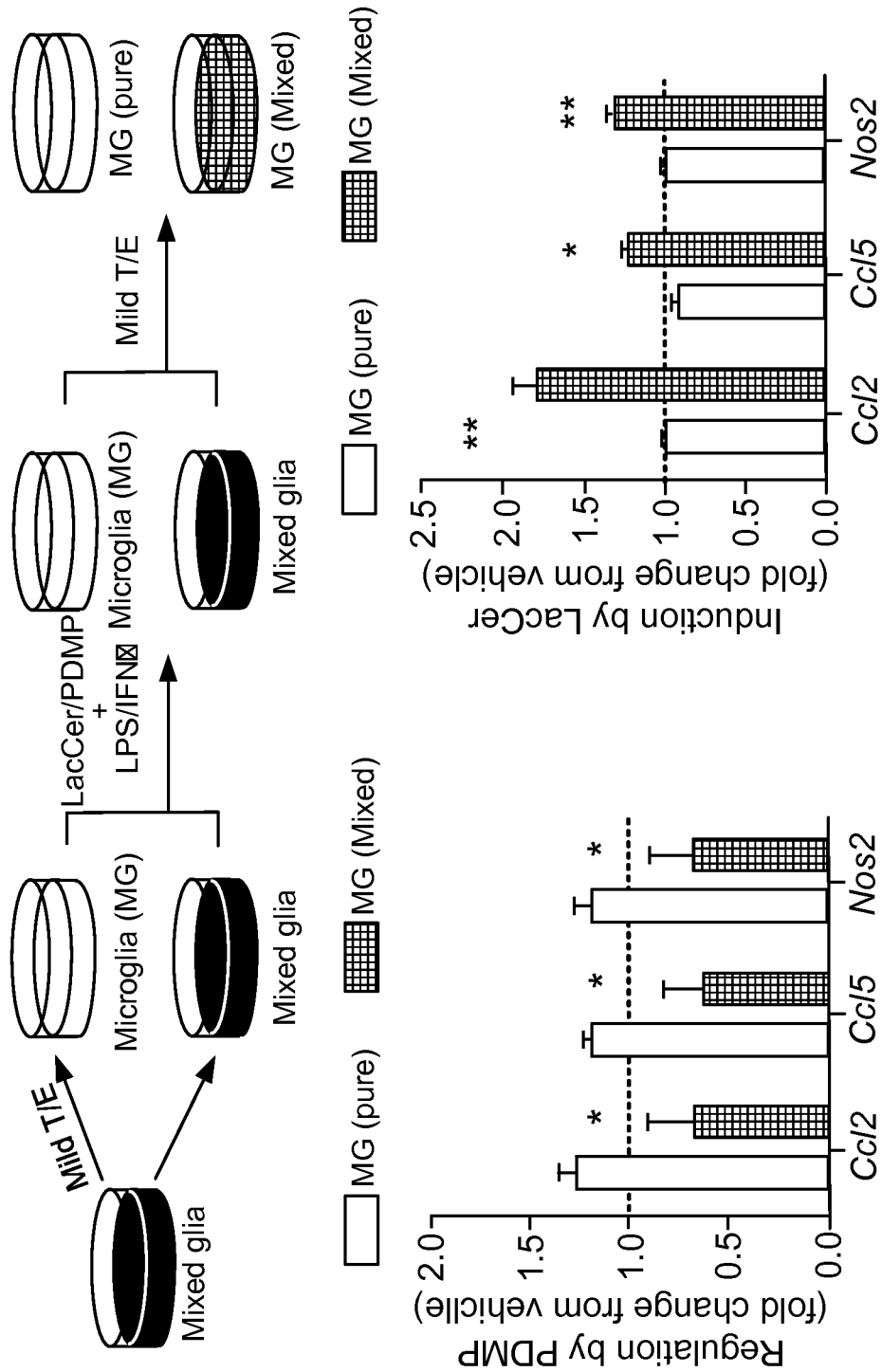

However, we detected significant effects of PDMP and LacCer on microglial activation in mixed glia cultures containing both microglia and astrocytes (FIG. 5i). To identify the B4GALT6/LacCer-dependent mechanisms involved in the regulation of microglial activation by astrocytes we used blocking antibodies. We treated mixed glia cultures with blocking antibodies to neutralize GM-CSF, IL-12, TNFα, or IL-6 signaling and analyzed microglial activation (as indicated by nos2 up-regulation) in the presence of LPS/IFNγ and LacCer. We found that blockade of GM-CSF inhibits the LacCer-dependent boost in the up-regulation of microglial nos2 (FIG. 5j). Indeed, we also found that B4GALT6/LacCer pathway controls the recruitment of NF-κB and IRF-1 to the csf2 (GM-CSF) promoter during astrocyte activation (FIG. 5k).

To evaluate the physiological relevance of these in vitro findings, we analyzed csf2 expression in astrocytes following b4galt6 knock-down with shRNAs during the chronic phase of NOD EAE. In agreement with our in vitro results, the knock down of b4galt6 led to a significant decrease in csf2 expression in astrocytes (FIG. 5l). Moreover, the specific knock-down of b4galt6 in astrocytes resulted in decreased nos2 expression in microglia (FIG. 5m). Taken together, these data suggest that GM-CSF produced by astrocytes in a B4GALT6/LacCer-dependent manner modulates microglia activation.

TABLE 3

| M1/M2 associated genes as previously described[29,30,60-62]. | | | |
|---|---|---|---|
| M1 associated genes | | M2 associated genes | |
| Ccl4 | Icam | Arg1 | Il8 |
| Ccl5 | Il1b | Ccl1 | Il21 |
| Ccl8 | Il6 | Ccl2 | Il21r |
| Ccl15 | Il7r | Ccl17 | Irf4 |
| Ccl19 | Il15 | Ccl20 | Maf |
| Ccl20 | Il15ra | Cd14 | Pparg |

TABLE 3-continued

M1/M2 associated genes as previously described[29,30,60-62].

| M1 associated genes | | M2 associated genes | |
|---|---|---|---|
| Ccl23 | Il12a | Cd163 | Ptgst1 |
| Cd40 | Il12b | Cd206 | Sra1 |
| Cd80 | Il12ra | Cd209 | Stat6 |
| Cd83 | Il18 | Cd36 | Tgfb |
| Cd86 | Il18r | Cd39 | Tlr1 |
| Cxcl9 | Il23a | Cd73 | Tlr8 |
| Cxcl10 | Irf5 | Cxcl1 | Ym1 |
| Cxcl11 | Nos2 | Cxcl2 | |
| Cxcl13 | Ptgs2 | Cxcl3 | |
| H2-Aa | Socs3 | Fizz1 | |
| H2-ab | Stat1 | Igf1 | |
| H2-Ea | Tnf | Il10 | |
| Marco | | | |

Example 6. B4GALT6 and LacCer Levels are Up-Regulated in MS Lesions

Figure 6A:
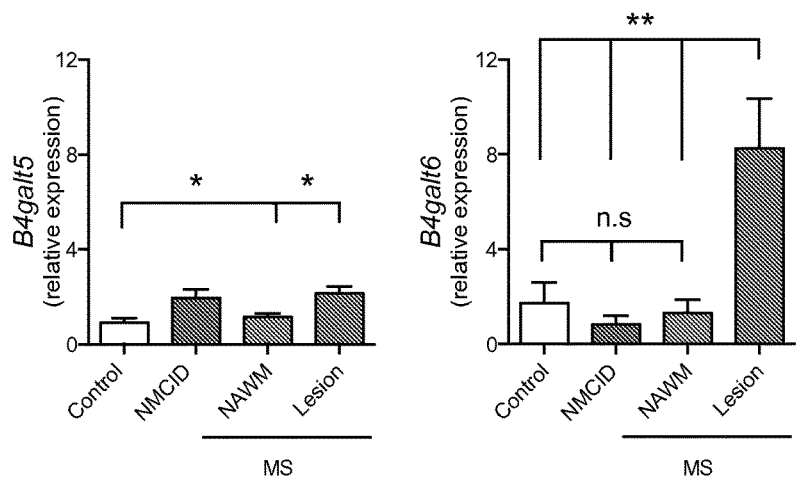

To examine the relevance of our findings for MS, we analyzed B4GALT6 and B4GALT5 expression in brain samples from MS patients and controls. We found a significant up-regulation of B4GALT5 (2.15±0.28 fold) and B4GALT6 (8.26.15±2.11 fold) expression in MS lesions, but not in normal appearing white matter (NAWM) or controls. In addition, in brain samples from non-MS CNS inflammatory diseases (NMCID) we detected an up-regulation of B4GALT5 (1.95±0.34) but not of B4GALT6 expression (0.82±0.37) (FIG. 6a).

Figure 6B:
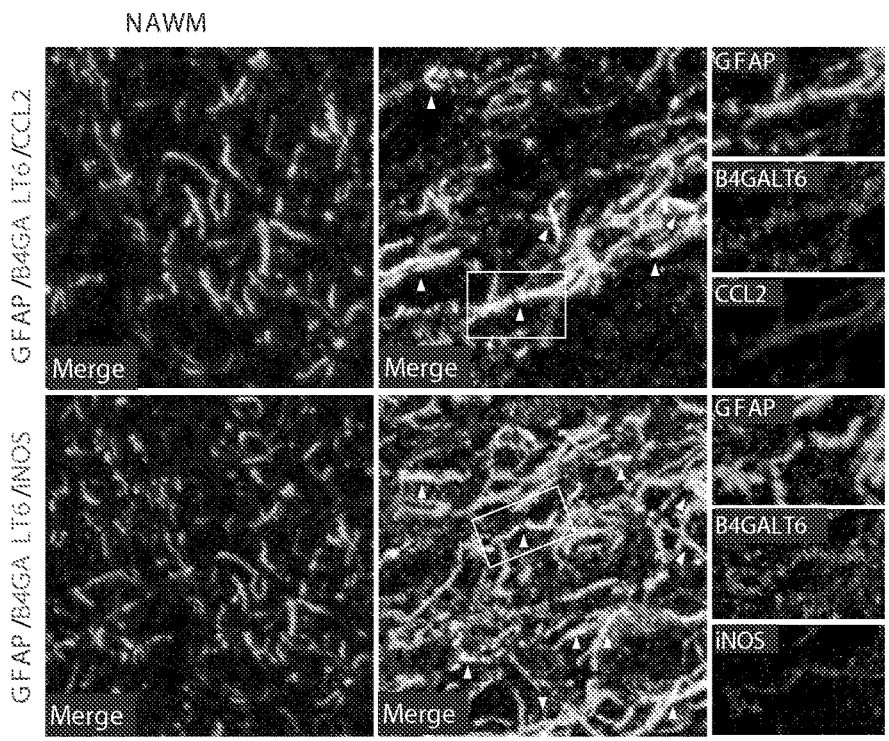

To further investigate the role of B4GALT6 up-regulation in MS we analyzed patient brain samples by IF and detected the expression of B4GALT6 in GFAP$^+$ astrocytes (FIG. 6b). Moreover, we detected the co-expression of B4GALT6 with CCL2 and iNOS in GFAP$^+$ astrocytes (FIG. 6b).

Figure 6C:
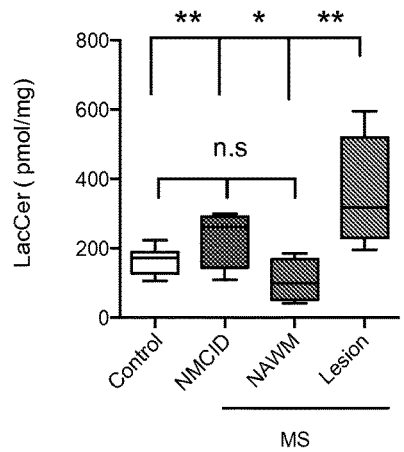

To investigate the biological relevance of the up-regulation of B4GALT5/6 expression, we quantified LacCer levels in the same collection of samples. In agreement with our data on B4GALT5/6 expression, we detected similar LacCer levels in control, NMCID and MS NAWM samples (FIG. 6c). LacCer levels, however, were significantly up-regulated in MS lesions, suggesting that increased B4GALT6 activity and LacCer levels are also associated with MS pathology.

Figure 6D:
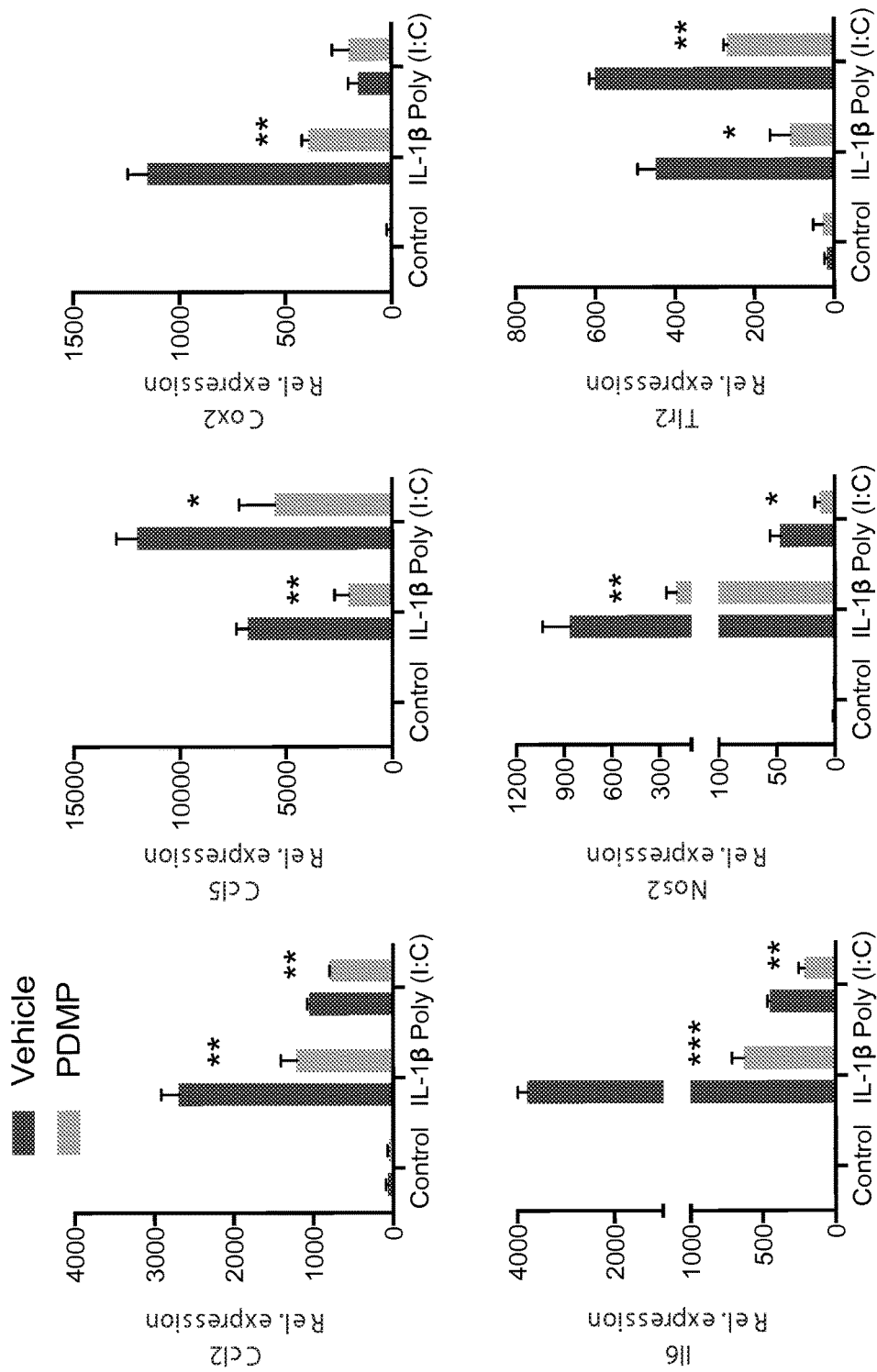

We next studied whether B4GALT6 also modulates the activity of human astrocytes. To that end, human primary astrocytes were activated by either the TLR-3 agonist poly (I:C) (an exogenous stimuli) or IL-1β (endogenous stimuli), in the presence of PDMP or vehicle control. We found that B4GALT6 inhibition led to a significant decrease in CCL2, CCL5, COX2, 1L6, NOS2 and TLR2 expression (FIG. 6d). Thus, these results suggest that B4GALT6 is a potential therapeutic target for the regulation of astrocyte activity in human neuroinflammatory disorders.

Example 7. Miglustat Inhibits Astrocyte Activation

As demonstrated herein, LacCer promotes astrocyte activation and neurodegeneration. Miglustat, a drug approved for human use (Venier, R. E. & Igdoura, S. A. Miglustat as a therapeutic agent: prospects and caveats. J Med Genet 49, 591-597 (2012)), crosses the blood brain barrier and inhibits the synthesis of glucosylceramide (GlcCer), which is used by B4GALT6 to synthesize LacCer (FIG. 1A) (Venier & Igdoura, J Med Genet 49, 591-597 (2012); Jeyakumar et al., Nature reviews. Neuroscience 6, 713-725 (2005); Platt et al. Science (New York, N.Y.) 276, 428-431 (1997)). In support of its repurposing for the modulation of astrocyte activity, it was found that, similar to the observation with PDMP, Miglustat inhibits astrocyte activation (FIG. 7B). Thus, Miglustat can be used to suppress pathologic astrocyte activation in MS and other neurodegenerative diseases.

Example 8. Miglustat Treatment Halts Chronic EAE Progression

Experimental autoimmune encephalomyelitis (EAE) constitutes a useful experimental model of MS, with a proven record in attributing to MS research and actually, EAE has led directly to the development of three therapies approved for use in multiple sclerosis (MS): glatiramer acetate, mitoxantrone, and natalizumab. Immunization of non-obese diabetic (NOD) mice with MOG$_{35-55}$, results in an acute attack (acute phase) followed by a phase of progressive and irreversible accumulation of neurological impairment (progressive phase) that resembles secondary progressive MS.

To investigate the therapeutic potential of Miglustat in the progressive phase of NOD EAE we initiated Miglustat administration at the onset of the progressive phase (FIG. 16). Miglustat was administrated daily via the oral or nasal routes. Mice treated orally were given a single dose of either 1800 kg/mg or 600 mg/kg of Miglustat, while mice treated nasally where treated twice a day with a dose of 900 mg/kg (amounting to 1800 mg/kg per day). We found that daily administration of Miglustat suppressed the clinical course of disease progression (FIG. 16). Moreover, it also reduced the recruitment of inflammatory monocytes to the CNS (FIG. 17), which are thought to be major contributors to the pathogenesis of MS and other neurodegenerative disorders (see, e.g., David and Kroner, Nat Rev Neurosci. 2011; 12(7):388-99; Lawrence and Natoli, Nat Rev Immunol. 2011; 11(11):750-61; Murray and Wynn, Nat Rev Immunol. 2011; 11(11):723-37). Of note, miglustat did not affect the T-cell response or body weight lost (FIGS. 18 and 19, respectively). Taken together, these data suggest that Miglustat administration halts chronic EAE progression, and represents a therapeutic approach for progressive MS.

REFERENCES

1. Clarke, L. E. & Barres, B. A. Emerging roles of astrocytes in neural circuit development. Nat Rev Neurosci 14, 311-321 (2013).
2. Rouach, N., Koulakoff, A., Abudara, V., Willecke, K. & Giaume, C. Astroglial metabolic networks sustain hippocampal synaptic transmission. Science 322, 1551-1555 (2008).
3. Seifert, G., Schilling, K. & Steinhauser, C. Astrocyte dysfunction in neurological disorders: a molecular perspective. Nat Rev Neurosci 7, 194-206 (2006).
4. Tsai, H. H., et al. Regional astrocyte allocation regulates CNS synaptogenesis and repair. Science 337, 358-362 (2012).
5. Bush, T. G., et al. Leukocyte infiltration, neuronal degeneration, and neurite outgrowth after ablation of scar-forming, reactive astrocytes in adult transgenic mice. Neuron 23, 297-308 (1999).
6. Myer, D. J., Gurkoff, G. G., Lee, S. M., Hovda, D. A. & Sofroniew, M. V. Essential protective roles of reactive astrocytes in traumatic brain injury. Brain 129, 2761-2772 (2006).
7. Toft-Hansen, H., Fuchtbauer, L. & Owens, T Inhibition of reactive astrocytosis in established experimental autoimmune encephalomyelitis favors infiltration by myeloid cells over T cells and enhances severity of disease. *Glia* 59, 166-176 (2011).
8. Voskuhl, R. R., et al. Reactive astrocytes form scar-like perivascular barriers to leukocytes during adaptive immune inflammation of the CNS. *J Neurosci* 29, 11511-11522 (2009).
9. Mayo, L., Quintana, F. J. & Weiner, H. L. The innate immune system in demyelinating disease. *Immunol Rev* 248, 170-187 (2012).
10. Nylander, A. & Hafler, D. A. Multiple sclerosis. *J Clin Invest* 122, 1180-1188 (2012).
11. Weiner, H. L. The challenge of multiple sclerosis: how do we cure a chronic heterogeneous disease? *Ann Neurol* 65, 239-248 (2009).
12. Joseph, J., Bittner, S., Kaiser, F. M., Wiendl, H. & Kissler, S. IL-17 silencing does not protect nonobese diabetic mice from autoimmune diabetes. *J Immunol* 188, 216-221 (2012).
13. Basso, A. S., et al. Reversal of axonal loss and disability in a mouse model of progressive multiple sclerosis. *J Clin Invest* 118, 1532-1543 (2008).
14. Farez, M. F., et al. Toll-like receptor 2 and poly(ADP-ribose) polymerase 1 promote central nervous system neuroinflammation in progressive EAE. *Nat Immunol* 10, 958-964 (2009).
15. Cao, W., et al. Leukemia inhibitory factor inhibits T helper 17 cell differentiation and confers treatment effects of neural progenitor cell therapy in autoimmune disease. *Immunity* 35, 273-284 (2011).
16. Pluchino, S., et al. Injection of adult neurospheres induces recovery in a chronic model of multiple sclerosis. *Nature* 422, 688-694 (2003).
17. Chatterjee, S. & Alsaeedi, N. Lactosylceramide synthase as a therapeutic target to mitigate multiple human diseases in animal models. *Adv Exp Med Biol* 749, 153-169 (2012).
18. Pannu, R., Won, J. S., Khan, M., Singh, A. K. & Singh, I. A novel role of lactosylceramide in the regulation of lipopolysaccharide/interferon-gamma-mediated inducible nitric oxide synthase gene expression: implications for neuroinflammatory diseases. *J Neurosci* 24, 5942-5954 (2004).
19. Ajami, B., Bennett, J. L., Krieger, C., McNagny, K. M. & Rossi, F. M. Infiltrating monocytes trigger EAE progression, but do not contribute to the resident microglia pool. *Nat Neurosci* 14, 1142-1149 (2011).
20. Izikson, L., Klein, R. S., Charo, I. F., Weiner, H. L. & Luster, A. D. Resistance to experimental autoimmune encephalomyelitis in mice lacking the CC chemokine receptor (CCR)2. *J Exp Med* 192, 1075-1080 (2000).
21. Mildner, A., et al. CCR2+Ly-6Chi monocytes are crucial for the effector phase of autoimmunity in the central nervous system. *Brain* 132, 2487-2500 (2009).
22. Watkins, T. A., Emery, B., Mulinyawe, S. & Barres, B. A. Distinct stages of myelination regulated by gamma-secretase and astrocytes in a rapidly myelinating CNS coculture system. *Neuron* 60, 555-569 (2008).
23. Nishie, T., et al. Beta4-galactosyltransferase-5 is a lactosylceramide synthase essential for mouse extra-embryonic development. *Glycobiology* 20, 1311-1322 (2010).
24. Tokuda, N., et al. beta4GalT6 is involved in the synthesis of lactosylceramide with less intensity than beta4GalT5. *Glycobiology* 23, 1175-1183 (2013).
25. Yan, Y., et al. CNS-specific therapy for ongoing EAE by silencing IL-17 pathway in astrocytes. *Molecular therapy: the journal of the American Society of Gene Therapy* 20, 1338-1348 (2012).
26. Lee, J. K., et al. Lactosylceramide Mediates the Expression of Adhesion Molecules in TNF-alpha and IFNgamma-stimulated Primary Cultured Astrocytes. *The Korean journal of physiology & pharmacology: official journal of the Korean Physiological Society and the Korean Society of Pharmacology* 15, 251-258 (2011).
27. Huang, D. R., Wang, J., Kivisakk, P., Rollins, B. J. & Ransohoff, R. M. Absence of monocyte chemoattractant protein 1 in mice leads to decreased local macrophage recruitment and antigen-specific T helper cell type 1 immune response in experimental autoimmune encephalomyelitis. *J Exp Med* 193, 713-726 (2001).
28. Heppner, F. L., et al. Experimental autoimmune encephalomyelitis repressed by microglial paralysis. *Nat Med* 11, 146-152 (2005).
29. Lawrence, T. & Natoli, G. Transcriptional regulation of macrophage polarization: enabling diversity with identity. *Nat Rev Immunol* 11, 750-761 (2011).
30. Murray, P. J. & Wynn, T. A. Protective and pathogenic functions of macrophage subsets. *Nat Rev Immunol* 11, 723-737 (2011).
31. Miron, V. E., et al. M2 microglia and macrophages drive oligodendrocyte differentiation during CNS remyelination. *Nat Neurosci* 16, 1211-1218 (2013).
32. Bi, F., et al. Reactive astrocytes secrete lcn2 to promote neuron death. *Proc Natl Acad Sci USA* 110, 4069-4074 (2013).
33. Colombo, E., et al. Stimulation of the neurotrophin receptor TrkB on astrocytes drives nitric oxide production and neurodegeneration. *J Exp Med* 209, 521-535 (2012).
34. Freeman, M. R. Specification and morphogenesis of astrocytes. *Science* 330, 774-778 (2010).
35. Hochstim, C., Deneen, B., Lukaszewicz, A., Zhou, Q. & Anderson, D. J. Identification of positionally distinct astrocyte subtypes whose identities are specified by a homeodomain code. *Cell* 133, 510-522 (2008).
36. Matyash, V. & Kettenmann, H. Heterogeneity in astrocyte morphology and physiology. *Brain Res Rev* 63, 2-10 (2010).
37. Zhang, Y. & Barres, B. A. Astrocyte heterogeneity: an underappreciated topic in neurobiology. *Curr Opin Neurobiol* 20, 588-594 (2010).
38. Molofsky, A. V., et al. Astrocytes and disease: a neurodevelopmental perspective. *Genes & development* 26, 891-907 (2012).
39. Sofroniew, M. V. Molecular dissection of reactive astrogliosis and glial scar formation. *Trends in neurosciences* 32, 638-647 (2009).
40. David, S. & Kroner, A. Repertoire of microglial and macrophage responses after spinal cord injury. *Nat Rev Neurosci* 12, 388-399 (2011).
41. Ponomarev, E. D., et al. GM-CSF production by autoreactive T cells is required for the activation of microglial cells and the onset of experimental autoimmune encephalomyelitis. *J Immunol* 178, 39-48 (2007).
42. Codarri, L., et al. RORgammat drives production of the cytokine GM-CSF in helper T cells, which is essential for the effector phase of autoimmune neuroinflammation. *Nat Immunol* 12, 560-567 (2011).
43. El-Behi, M., et al. The encephalitogenicity of T(H)17 cells is dependent on IL-1- and IL-23-induced production of the cytokine GM-CSF. *Nat Immunol* 12, 568-575 (2011).
44. Zamanian, J. L., et al. Genomic analysis of reactive astrogliosis. *J Neurosci* 32, 6391-6410 (2012).

45. Jahng, A., et al. Prevention of autoimmunity by targeting a distinct, noninvariant CD1d-reactive T cell population reactive to sulfatide. *J Exp Med* 199, 947-957 (2004).
46. Schwab, J. M., Chiang, N., Arita, M. & Serhan, C. N. Resolvin E1 and protectin D1 activate inflammation-resolution programmes. *Nature* 447, 869-874 (2007).
47. Kanter, J. L., et al. Lipid microarrays identify key mediators of autoimmune brain inflammation. *Nat Med* 12, 138-143 (2006).
48. Quintana, F. J., Yeste, A., Weiner, H. L. & Covacu, R. Lipids and lipid-reactive antibodies as biomarkers for multiple sclerosis. *J Neuroimmunol* 248, 53-57 (2012).
49. Nolte, C., et al. GFAP promoter-controlled EGFP-expressing transgenic mice: a tool to visualize astrocytes and astrogliosis in living brain tissue. *Glia* 33, 72-86 (2001).
50. Cardona, A. E., Huang, D., Sasse, M. E. & Ransohoff, R. M. Isolation of murine microglial cells for RNA analysis or flow cytometry. *Nat Protoc* 1, 1947-1951 (2006).
51. Cahoy, J. D., et al. A transcriptome database for astrocytes, neurons, and oligodendrocytes: a new resource for understanding brain development and function. *J Neurosci* 28, 264-278 (2008).
52. Prinz, M., Priller, J., Sisodia, S. S. & Ransohoff, R. M. Heterogeneity of CNS myeloid cells and their roles in neurodegeneration. *Nat Neurosci* 14, 1227-1235 (2011).
53. Ulitsky, I., et al. Expander: from expression microarrays to networks and functions. *Nat Protoc* 5, 303-322 (2010).
54. Saura, J., Tusell, J. M. & Serratosa, J. High-yield isolation of murine microglia by mild trypsinization. *Glia* 44, 183-189 (2003).
55. Kunis, G., et al. IFN-gamma-dependent activation of the brain's choroid plexus for CNS immune surveillance and repair. *Brain* 136, 3427-3440 (2013).
56. Menheniott, T. R., Charalambous, M. & Ward, A. Derivation of primary choroid plexus epithelial cells from the mouse. *Methods in molecular biology* 633, 207-220 (2010).
57. Jack, C. S., et al. TLR signaling tailors innate immune responses in human microglia and astrocytes. *J Immunol* 175, 4320-4330 (2005).
58. Alvarez, I I., et al. The Hedgehog pathway promotes blood-brain barrier integrity and CNS immune quiescence. *Science* 334, 1727-1731 (2011).
59. Nair, A., Frederick, T. J. & Miller, S. D. Astrocytes in multiple sclerosis: a product of their environment. *Cellular and molecular life sciences: CMLS* 65, 2702-2720 (2008).
60. Krausgruber, T., et al. IRF5 promotes inflammatory macrophage polarization and TH1-TH17 responses. *Nat Immunol* 12, 231-238 (2011).
61. Sica, A. & Mantovani, A. Macrophage plasticity and polarization: in vivo veritas. *J Clin Invest* 122, 787-795 (2012).
62. Martinez, F. O., Sica, A., Mantovani, A. & Locati, M. Macrophage activation and polarization. *Frontiers in bioscience: a journal and virtual library* 13, 453-461 (2008).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating progressive multiple sclerosis (MS) in a subject, the method comprising administering to the subject a therapeutically effective amount of an inhibitor of lactosylceramide (LacCer) synthesis, wherein the inhibitor of LacCer synthesis is an inhibitor of B4GALT6 or of glucosylceramide (GlcCer) synthesis.

2. A method of treating progressive multiple sclerosis (MS) in a subject, the method comprising administering to the subject a therapeutically effective amount of an inhibitor of LacCer synthesis, wherein the inhibitor of LacCer synthesis is an inhibitor of glucosylceramide (GlcCer) synthesis.

3. The method of claim 2, wherein the inhibitor of GlcCer synthesis is selected from the group consisting of 1-(3',4'-ethylenedioxy)phenyl-2-nonanoylamino-3-pyrrolidino-1-propanol; 1-(3',4'-ethylenedioxy)phenyl-2-octanoylamino-3-pyrrolidino-1-propanol; D-threo-(1R,2R)-phenyl-2-decanoylamino-3-morpholino-1-propanol (PDMP) and analogs thereof including D-PDMP; PPMP (DL-threo-1-Phenyl-2-palmitoylamino-3-morpholino-1-propanol), D-threo-EtDO-P4; ((1R, 2R)-nonanoic acid[2-(2',3'-dihydro-benzo [1,4] dioxin-6'-yl)-2-hydroxy-1-pyrrolidin-1-ylmethyl-ethyl]-amide-L-tartaric acid salt; CCG0203586 (1-hydroxy-3-(pyrrolidin-1-yl)acetamide); Genz-112638 (eliglustat); Genz-529468; deoxynojiromycin-based GlcCer inhibitors; GZ-161; Genz-682452; EXEL-0346; OGT2378; and Genz-123346.

4. The method of claim 3, wherein the deoxynojiromycin-based GlcCer inhibitor is N-(5'-adamantane-1'-yl-methoxy)-pentyl-1-deoxynojirimycin (AMP-DNM), N-butyl-deoxynojirimycin (miglustat) or a long-chain N-alkyl derivative of 1,5-dideoxy-1,5-imino-D-glucitol having from nine to about 20 carbon atoms in the alkyl chain.

5. The method of claim 4, wherein the N-alkyl substituent is selected from the group consisting of nonyl, decyl, undecyl, dodecyl, tetradecyl, hexadecyl, cis-11-hexadecenyl, octadecyl, cis-13-octadecenyl, and eicosyl.

6. The method of claim 1, wherein the inhibitor of LacCer synthesis is an inhibitor of B4GALT6 selected from the group consisting of a small molecule, an inhibitory nucleic acid targeting B4GALT6, or an inhibitory antibody that binds specifically to B4GALT6 and inhibits LacCer synthesis.

7. The method of claim 6, wherein the inhibitory nucleic acid targeting B4GALT6 is selected from the group consisting of antisense, siRNA, shRNA, and miRNA.

8. The method of claim 1, comprising administering an inhibitor of B4GALT6 and an inhibitor of GlcCer synthesis.

9. The method of claim 1, comprising selecting the subject on the basis that the subject has progressive MS.

10. The method of claim 1, further comprising administering an activator of glucocerebrosidase.

11. The method of claim 10, wherein the activator of glucocerebrosidase is Saposin C or an active fragment thereof; NCGC00182186 (5-cyclopropylidene-7-(difluoromethyl)-N-(2-phenylsulfanylphenyl)-1H-pyrazolo[1,5-a]pyrimidine-3-carboxamide); NCGC00182510 ([2-(tert-butylamino)-2-oxoethyl] 2-[2-(4-bromoanilino)-2-oxoethoxy]benzoate) or phosphatidylserine.

12. The method of claim 1, wherein the compound is administered orally, nasally, intravenously, or intrathecally.

13. The method of claim 1, wherein the subject has SPMS and/or is selected on the basis that they have SPMS.

14. The method of claim 1, wherein the progressive multiple sclerosis (MS) is primary progressive multiple sclerosis (PPMS) or secondary progressive multiple sclerosis (SPMS).

15. A method of treating progressive multiple sclerosis (MS) in a subject, the method comprising administering to the subject a therapeutically effective amount of N-butyl-deoxynojirimycin (miglustat).

16. The method of claim 15, wherein the progressive multiple sclerosis (MS) is primary progressive multiple sclerosis (PPMS) or secondary progressive multiple sclerosis (SPMS).

* * * * *

UNITED STATES PATENT AND TRADEMARK OFFICE
CERTIFICATE OF CORRECTION

PATENT NO. : 9,927,437 B2
APPLICATION NO. : 15/103632
DATED : March 27, 2018
INVENTOR(S) : Francisco J. Quintana et al.

It is certified that error appears in the above-identified patent and that said Letters Patent is hereby corrected as shown below:

On the Title Page

In Column 1 (Inventors), Line 6, delete "Fivataim (IL)" and insert -- Givatayim (IL) --;

In Column 2 (Other Publications), Line 32, delete "153-469." and insert -- 153-169. --;

In the Claims

In Column 49, Line 35, in Claim 3, delete "((1R, 2R)-nonanoic" and insert -- (1R,2R)-nonanoic --;

In Column 49, Line 39, in Claim 3, delete "deoxynojiromycin-" and insert -- deoxynojirimycin- --;

In Column 49, Line 42, in Claim 4, delete "deoxynojiromycin-" and insert -- deoxynojirimycin- --.

Signed and Sealed this
Twenty-ninth Day of January, 2019

Andrei Iancu
*Director of the United States Patent and Trademark Office*

SEQUENCE LISTING

```
<160> NUMBER OF SEQ ID NOS: 16

<210> SEQ ID NO 1
<211> LENGTH: 80
<212> TYPE: PRT
<213> ORGANISM: Homo sapien

<400> SEQUENCE: 1

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro Lys Ser Leu Ser Glu Glu Cys Gln
        35                  40                  45

Glu Val Val Asp Thr Tyr Gly Ser Ser Ile Leu Ser Ile Leu Leu Glu
    50                  55                  60

Glu Val Ser Pro Glu Leu Val Cys Ser Met Leu His Leu Cys Ser Gly
65                  70                  75                  80

<210> SEQ ID NO 2
<211> LENGTH: 48
<212> TYPE: DNA
<213> ORGANISM: Artificial Sequence
<220> FEATURE:
<223> OTHER INFORMATION: synthetically generated shRNA

<400> SEQUENCE: 2
gcagcctgaa tgactcagat tctcgagaat ctgagtcatt caggctgc                48
```

```
<210> SEQ ID NO 3
<211> LENGTH: 47
<212> TYPE: DNA
<213> ORGANISM: Artificial Sequence
<220> FEATURE:
<223> OTHER INFORMATION: synthetically generated shRNA

<400> SEQUENCE: 3
cgatggactg aacaatttat tctcgagaat aaattgttca gtccacg        47

<210> SEQ ID NO 4
<211> LENGTH: 48
<212> TYPE: DNA
<213> ORGANISM: Artificial Sequence
<220> FEATURE:
<223> OTHER INFORMATION: synthetically generated shRNA

<400> SEQUENCE: 4
gcgcgatagc gctaataatt tctcgagaaa ttattagcgc tatcgcgc       48

<210> SEQ ID NO 5
<211> LENGTH: 23
<212> TYPE: DNA
<213> ORGANISM: Artificial Sequence
<220> FEATURE:
<223> OTHER INFORMATION: synthetically generated primer

<400> SEQUENCE: 5
cagctaaata tctctcccga agg                                  23

<210> SEQ ID NO 6
<211> LENGTH: 20
<212> TYPE: DNA
<213> ORGANISM: Artificial Sequence
<220> FEATURE:
<223> OTHER INFORMATION: synthetically generated primer

<400> SEQUENCE: 6
catagatgcc cacagctcat                                      20

<210> SEQ ID NO 7
<211> LENGTH: 21
<212> TYPE: DNA
<213> ORGANISM: Artificial Sequence
<220> FEATURE:
<223> OTHER INFORMATION: synthetically generated primer

<400> SEQUENCE: 7
ctgccaattc ttccctcttt c                                    21

<210> SEQ ID NO 8
<211> LENGTH: 21
<212> TYPE: DNA
<213> ORGANISM: Artificial Sequence
<220> FEATURE:
<223> OTHER INFORMATION: synthetically generated primer

<400> SEQUENCE: 8
gtgggttgga atttggtatt t                                    21

<210> SEQ ID NO 9
<211> LENGTH: 21
<212> TYPE: DNA
<213> ORGANISM: Artificial Sequence
<220> FEATURE:
```

<223> OTHER INFORMATION: synthetically generated primer

<400> SEQUENCE: 9
gaccagatgg gtggagtgac c                                              21

<210> SEQ ID NO 10
<211> LENGTH: 20
<212> TYPE: DNA
<213> ORGANISM: Artificial Sequence
<220> FEATURE:
<223> OTHER INFORMATION: synthetically generated primer

<400> SEQUENCE: 10
agccacacgc ttctggttcc                                                20

<210> SEQ ID NO 11
<211> LENGTH: 21
<212> TYPE: DNA
<213> ORGANISM: Artificial Sequence
<220> FEATURE:
<223> OTHER INFORMATION: synthetically generated primer

<400> SEQUENCE: 11
gctttcgagg gtcagataac a                                              21

<210> SEQ ID NO 12
<211> LENGTH: 18
<212> TYPE: DNA
<213> ORGANISM: Artificial Sequence
<220> FEATURE:
<223> OTHER INFORMATION: synthetically generated primer

<400> SEQUENCE: 12
cacacgcttg ggctaaga                                                  18

<210> SEQ ID NO 13
<211> LENGTH: 22
<212> TYPE: DNA
<213> ORGANISM: Artificial Sequence
<220> FEATURE:
<223> OTHER INFORMATION: synthetically generated primer

<400> SEQUENCE: 13
cacagactag gagtgtccat ca                                             22

<210> SEQ ID NO 14
<211> LENGTH: 20
<212> TYPE: DNA
<213> ORGANISM: Artificial Sequence
<220> FEATURE:
<223> OTHER INFORMATION: synthetically generated primer

<400> SEQUENCE: 14
gcagcagcca tcaggtattt                                                20

<210> SEQ ID NO 15
<211> LENGTH: 20
<212> TYPE: DNA
<213> ORGANISM: Artificial Sequence
<220> FEATURE:
<223> OTHER INFORMATION: synthetically generated primer

<400> SEQUENCE: 15
accatgcgaa gatgagtgga                                                20

```
<210> SEQ ID NO 16
<211> LENGTH: 20
<212> TYPE: DNA
<213> ORGANISM: Artificial Sequence
<220> FEATURE:
<223> OTHER INFORMATION: synthetically generated primer

<400> SEQUENCE: 16
accatgcgaa gatgagtgga                                              20
```